US008633170B2

(12) United States Patent
Cheung

(10) Patent No.: US 8,633,170 B2
(45) Date of Patent: Jan. 21, 2014

(54) THERAPY-ENHANCING GLUCAN

(75) Inventor: Nai-Kong V. Cheung, New York, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 83 days.

(21) Appl. No.: 12/854,603

(22) Filed: Aug. 11, 2010

(65) Prior Publication Data
US 2011/0195071 A1 Aug. 11, 2011

Related U.S. Application Data

(63) Continuation of application No. 12/036,462, filed on Feb. 25, 2008, now abandoned, which is a continuation of application No. 11/218,044, filed on Aug. 31, 2005, now Pat. No. 7,462,607, which is a continuation of application No. 10/621,027, filed on Jul. 16, 2003, now Pat. No. 7,507,724, which is a continuation-in-part of application No. PCT/US02/01276, filed on Jan. 15, 2002.

(60) Provisional application No. 60/261,911, filed on Jan. 16, 2001.

(51) Int. Cl.
C08B 37/00 (2006.01)
A61K 31/716 (2006.01)

(52) U.S. Cl.
CPC ........... A61K 31/716 (2013.01); C08B 37/0024 (2013.01)
USPC ....................................... 514/54; 536/123.12

(58) Field of Classification Search
None
See application file for complete search history.

(56) References Cited

U.S. PATENT DOCUMENTS

| 3,975,553 A | 8/1976 | Griffon |
| 3,987,166 A | 10/1976 | Komatsu et al. |
| 4,251,519 A | 2/1981 | Robbins et al. |
| 4,343,784 A | 8/1982 | Massot et al. |
| 4,454,289 A | 6/1984 | Nakajima et al. |
| 4,705,780 A | 11/1987 | Massot et al. |
| 4,761,402 A | 8/1988 | Williams et al. |
| 4,818,752 A | 4/1989 | Williams et al. |
| 4,833,131 A | 5/1989 | Williams et al. |
| 4,900,722 A | 2/1990 | Williams et al. |
| 4,926,094 A | 5/1990 | Bondeson et al. |
| 4,992,540 A | 2/1991 | Jamas et al. |
| 5,032,401 A | 7/1991 | Jamas et al. |
| 5,037,972 A | 8/1991 | Jamas et al. |
| 5,130,127 A | 7/1992 | Herlyn |
| 5,189,028 A | 2/1993 | Nikl et al. |
| 5,322,841 A | 6/1994 | Jamas et al. |
| 5,504,079 A | 4/1996 | Jamas et al. |
| 5,532,223 A | 7/1996 | Jamas et al. |
| 5,576,015 A | 11/1996 | Donzis |
| 5,607,677 A | 3/1997 | Jamas et al. |
| 5,610,280 A * | 3/1997 | Brandt et al. ............... 530/387.5 |
| 5,622,939 A | 4/1997 | Jamas et al. |
| 5,622,940 A | 4/1997 | Ostroff et al. |
| 5,696,079 A | 12/1997 | Lane et al. |
| 5,702,719 A | 12/1997 | Donzis |
| 5,726,023 A | 3/1998 | Cheever et al. |
| 5,736,137 A * | 4/1998 | Anderson et al. .......... 424/133.1 |
| 5,741,495 A | 4/1998 | Jamas et al. |
| 5,783,569 A | 7/1998 | Jamas et al. |
| 5,804,199 A | 9/1998 | Aasjord et al. |
| 5,811,542 A | 9/1998 | Jamas et al. |
| 5,817,643 A | 10/1998 | Jamas et al. |
| 5,849,720 A | 12/1998 | Jamas et al. |
| 5,935,821 A * | 8/1999 | Chatterjee et al. ........... 435/69.6 |
| 5,980,918 A | 11/1999 | Klein |
| 6,020,324 A | 2/2000 | Jamas et al. |
| 6,117,850 A | 9/2000 | Patchen et al. |
| 6,143,731 A | 11/2000 | Jamas et al. |
| 6,143,883 A | 11/2000 | Lehmann et al. |
| 6,217,866 B1 * | 4/2001 | Schlessinger et al. ..... 424/143.1 |
| 6,573,245 B1 | 6/2003 | Marciani |
| 6,664,370 B2 | 12/2003 | Cheever et al. |

(Continued)

FOREIGN PATENT DOCUMENTS

| CA | 2434938 | 1/2002 |
| DE | 30 19 614 A1 | 12/1981 |

(Continued)

OTHER PUBLICATIONS

Supplementary Partial European Search Report, Feb. 5. 2008, for Sloan-Kettering Institute for Cancer Research, European Application No. EP 02 70 7502, filed Aug. 4, 2003.

(Continued)

Primary Examiner — Eric S Olson
(74) Attorney, Agent, or Firm — Law Offices of Albert Wai-Kit Chan, PLLC

(57) ABSTRACT

This invention provides a composition comprising an effective amount of glucan capable of enhancing efficacy of antibodies. This invention further provides the above compositions and a pharmaceutically acceptable carrier. This invention also provides a method for treating a subject with cancer comprising administrating the above-described composition to the subject. This invention provides a composition comprising effective amount of glucan capable of enhancing efficacy of vaccines. This invention also provides a method of treating a subject comprising administrating the above pharmaceutical composition to the subject. This invention provides a composition comprising effective amount of glucan capable of enhancing efficacy of natural antibodies. This invention provides a composition comprising effective amount of glucan capable of enhancing host immunity. This invention also provides a composition comprising effective amount of glucan capable of enhancing the action of an agent in preventing tissue rejection.

23 Claims, 36 Drawing Sheets

(56) References Cited

U.S. PATENT DOCUMENTS

Figure 1:
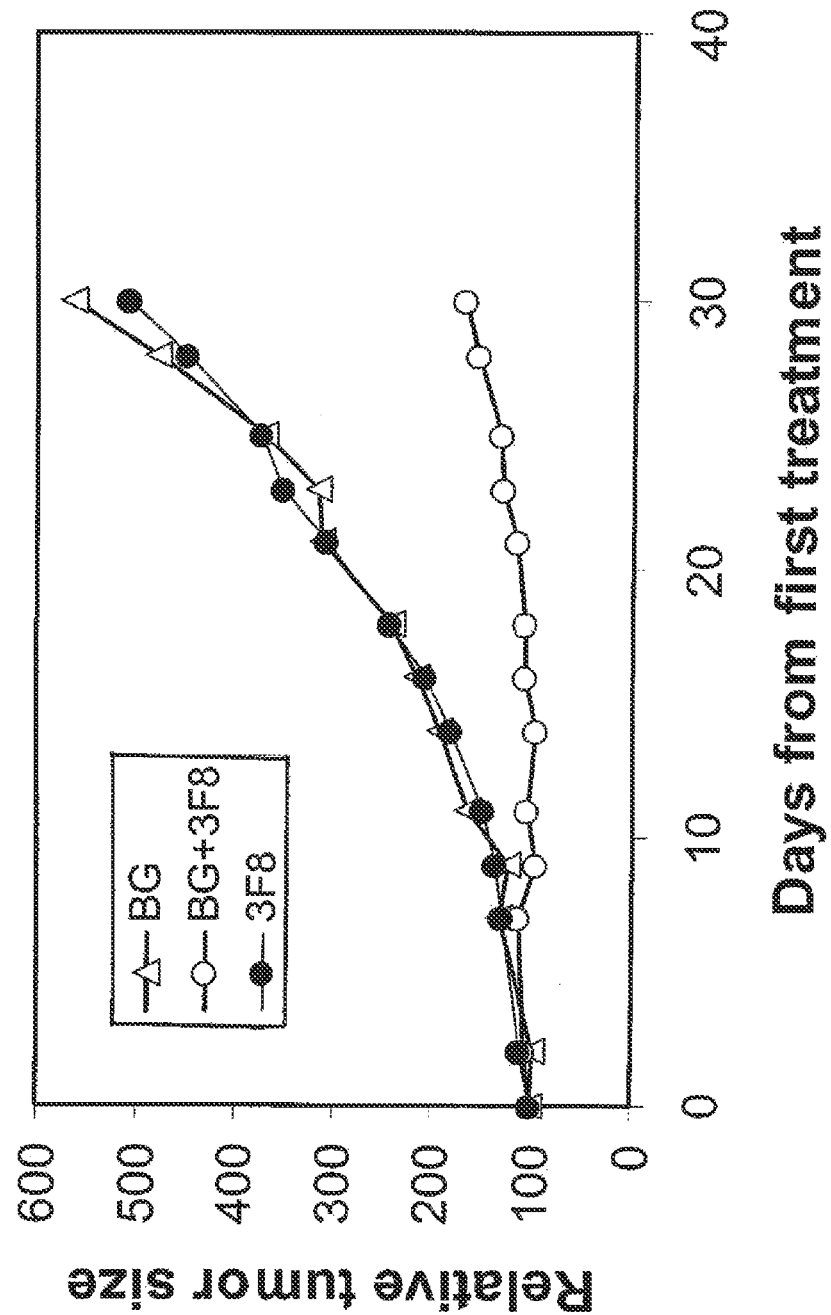

| | | | |
|---|---|---|---|
| 7,030,101 | B2 | 4/2006 | Pavliak et al. |
| 7,070,778 | B2 | 7/2006 | Yvin et al. |
| 7,462,607 | B2 * | 12/2008 | Cheung .................. 514/54 |
| 7,507,724 | B2 * | 3/2009 | Cheung .................. 514/54 |
| 7,704,973 | B2 * | 4/2010 | Cheung .................. 514/54 |
| 2002/0044919 | A1 | 4/2002 | Yu |
| 2002/0119928 | A1 | 8/2002 | McAnalley |
| 2002/0160014 | A1 | 10/2002 | Rodriguez et al. |
| 2003/0180254 | A1 | 9/2003 | Lane et al. |
| 2004/0109857 | A1 | 6/2004 | Chu et al. |
| 2004/0116379 | A1 | 6/2004 | Cheung |
| 2004/0142000 | A1 | 7/2004 | Suga et al. |
| 2004/0248772 | A1 | 12/2004 | Yagita |
| 2004/0266726 | A1 | 12/2004 | Yagita |
| 2005/0118187 | A1 | 6/2005 | Yu |
| 2005/0208079 | A1 | 9/2005 | Cassone et al. |
| 2006/0009419 | A1 | 1/2006 | Ross et al. |
| 2006/0020128 | A1 | 1/2006 | Cheung |
| 2006/0160766 | A1 | 7/2006 | Cheung |
| 2006/0165700 | A1 | 7/2006 | Ostroff et al. |
| 2006/0188506 | A1 | 8/2006 | Cheung |
| 2006/0263355 | A1 | 11/2006 | Quan et al. |
| 2007/0020232 | A1 | 1/2007 | Rossignol et al. |
| 2007/0059310 | A1 | 3/2007 | Karel |
| 2007/0134259 | A1 | 6/2007 | Bundle et al. |
| 2009/0053221 | A1 * | 2/2009 | Cheung et al. ............. 424/133.1 |
| 2010/0216743 | A1 * | 8/2010 | Cheung .................. 514/54 |

FOREIGN PATENT DOCUMENTS

| | | |
|---|---|---|
| EP | 0194851 A2 | 9/1986 |
| EP | 0463540 A1 | 2/1992 |
| EP | 0759089 | 8/2002 |
| JP | 62252730 A2 | 11/1987 |
| JP | 63-500805 | 3/1988 |
| JP | 62252730 | 12/1988 |
| WO | WO 91/03248 | 3/1991 |
| WO | WO 95/30022 | 11/1995 |
| WO | 97/35619 | 10/1997 |
| WO | WO 98/39013 | 9/1998 |
| WO | WO 99/52548 | 10/1999 |
| WO | WO 00/15238 | 3/2000 |
| WO | 01/56601 | 8/2001 |
| WO | WO 01/62283 | 8/2001 |
| WO | WO 01/68105 | 11/2001 |
| WO | WO 01/80807 | 11/2001 |
| WO | WO 02/058711 | 8/2002 |
| WO | WO 03/004507 | 1/2003 |
| WO | WO 03/054077 | 7/2003 |
| WO | WO 2004/014320 | 2/2004 |
| WO | WO 2004/021994 | 3/2004 |
| WO | WO 2004/030613 | 3/2004 |
| WO | WO 2005/018544 | 3/2005 |
| WO | WO 2005/027936 | 3/2005 |
| WO | WO 2005/027938 | 3/2005 |
| WO | WO 2005/049044 | 6/2005 |
| WO | WO 2006/085895 | 8/2006 |
| WO | WO 2006/119395 | 11/2006 |
| WO | WO 2007/084661 | 8/2007 |

OTHER PUBLICATIONS

PCT International Search Report, Sep. 26, 2007, for Sloan-Kettering Institute for Cancer Research, Int'l Application No. PCT/US07/01427, Filed Jan. 18, 2007.
PCT Written Opinion of the International Searching Authority, Sep. 26, 2007, for Sloan-Kettering Institute for Cancer Research, Int'l Application No. PCT/US07/01427, Filed Jan. 18, 2007.
Chinese Office Action, May 9, 2008, for Sloan-KKettering Institute for Cancer Research, Chinese Application No. 200480020356.6, Filed Jan. 16 2006, corresponding to PCT/US04/23099.
U.S. Office Action, Feb. 22, 2008, for Nai-Kong V. Cheung, U.S. Appl. No. 10/565,484, filed Jan. 17, 2006.
U.S. Office Action, Aug. 7, 2007, for Nai-Kong V. Cheung, U.S. Appl. No. 11/218,044, filed Aug. 31, 2005.
U.S. Office Action, Aug. 7, 2007, for Nai-Kong V. Cheung, U.S. Appl. No. 10/621,027, filed Jul. 16, 2003.
U.S. Office Action, Jan. 4, 2007, for Nai-Kong V. Cheung, U.S. Appl. No. 10/621,027, filed Jul. 16, 2003.
U.S. Office Action, Nov. 22, 2006, for Nai-Kong V. Cheung, U.S. Appl. No. 11/218,044, filed Aug. 31, 2005.
U.S. Office Action, Mar. 10, 2006, for Nai-Kong V. Cheung, U.S. Appl. No. 11/218,044, filed Aug. 31, 2005.
U.S. Office Action, Mar. 6 2006, for Nai-Kong V. Cheung, U.S. Appl. No. 10/621,027, filed Jul. 16, 2003.
U.S. Office Action, Jul. 13, 2005, for Nai-Kong V. Cheung, U.S. Appl. No. 10/621,027, filed Jul. 16, 2003.
U.S. Office Action, Dec. 17, 2004, for Nai-Kong V. Cheung, U.S. Appl. No. 10/621,027, filed Jul. 16, 2003.
Beta Glucan Health Center webpage, Nov. 10, 2000, "PLEURAN—Beta-1,3/1-6-Glucan," http://www.glucan.com/therapy/therapy.com.
1999 The Merck Manual of Diagnosis and Therapy, 397-398, 948-949, 1916, 1979-1981.
Adachi et al., 1990, "Macrophage Activation in Vitro by Chemically Cross-Linked (1-3)-β-D-Glucans", Chem. Pharm. Bull., 38(4):988-992.
Bergman et al., 1999, "Treatment of Neoplastic Meningeal Xenografts by Intraventricular Administration of an Antigangiioside Monoclonal Antibody, 3F8," Int. J. Cancer, 82.538-548.
Bluhm et al.; 1977, "The triple helical structure of lentinan, a linear β-D(1→3)-D-Gglucan", Can J Chem, 55:293-299.
Bogwald et al., 1982, "The Cytoxic Effect of Mouse Macrophages Stimulated in Vitro by a β-1,3-D-Glucan from Yeast Cell Walls", Scandinavian Journal of Immunology, 15:297-304.
Bohn, J.A., and BeMiller, J.N., 1995, "(1→3)β-Glucants as biological response modifiers: a review of structure-functional activity relationship," Carbohydrate Polymers, 28:3-14.
Bowers et al., 1989, "Glucan Enhances Survival in an Intraabdominal Infection Model", Journal of Surgical Research, vol. 47(2):183-188.
Capurro et al., 1998, "FC-2.15, a monoclonal antibody active against human breast cancer, specifically recognizes Lewisx hapten," Cancer Immunol. Immunother., 45:334-339.
Cheung, N.-K. V., et al., 2002, "Quantitation of GD2 Synthase mRNA by Real-Time Reverse Transcription-Polymerase Chain Reaction—Utility in Bone Marrow Purging of Neuroblastoma by Anti-GD2 Antibody 3F8," Cancer, 94:3042-3048.
Cheung, N.-K. V., et al., 1985, "Monoclonal Antibodies to a Glycolipid Antigen on Human Neuroblastoma Cells," Canc. Res, 45:2642-2649.
Chihara et al., 1970, "Fractionation and purification of the polysaccharides with Marked Antitumor Activity, Especially Lentinan, from Lentinus edodes (Berk.) Sing. (an Edible Mushroom)", Cancer Res, 30:2776-2781.
Chihara et al., 1981; "The antitumor polysaccharide Lentinan: an overview", Manipulation of Host Defence Mechanisms, 1-16.
Chihara et al., 1982, "Current Status and Perspectives of Immunomodulators of Microbial Origin", International Journal of Tissue Reactions, 4:207-225.
Damge et al., 1996, "Intestinal absorption of PLAGA microspheres in the rat," J. Anat., 189:491-501.
D'Amico et al., 2000 "Molecular Biologic Substaging of Stage I Lung Cancer According to Gender and Histology," Ann. Thorac. Surg., 69:882-886.
David et al., 1996, "Growth arrest of solid human neuroblastoma xenografts in nude rats by natural IgM from healthy humans," Nature Medicine, 2:686-689.
Di Luzio et al., 1985, "Glucans as Immunomodualators", Advances in Immunopharmacology, Permagon Press, NY, 369-375.
Di Luzio et al., 1980, "Comparative Evaluation of the Tumor Inhibitory and Antibacterial Activity of Solubilized and Particulate Glucan", Recent Results in Cancer Research, 75.165-172.
Di Luzio, Nicholas R., 1985, "Update on the Immunomodulating Activities of Glucans", Springer Seminars in Immunopathology, 8:387-400.

(56) References Cited

OTHER PUBLICATIONS

Di Luzio, Nicholas R., 2063, "Immunopharmacology of glucan: a broad spectrum enhance of host defense mechanisms", T.I.P.S., 344-347.

Engler et al., 2001, "A Novel Metastatic Animal Model Reflecting the Clinical Appearance of Human Neuroblastoma: Growth Arrest of Orthotopic Tumors by Natural, Cytotoxic Human Immunoglobulin M Antibodies," Cancer Research 61:2968-2973.

Florence A., 1997, "The oral absorption of micro- and nanoparticulates: Neither exceptional nor unusual," Pharmaceutical Research, 14(3):259-266.

Furue et al., 1985, "Clinical evaluation of schizophyllan (SPG)in advanced gastric cancer (the second report): a randomized controlled study," Gan to Kagaku Ryoho, 12: 1272-1277.

Hamuro et al., 1971, "The significance of the higher structure of the polysaccharides lentinan and pachymaran with regard to their antitumour activity", Chem. Biol. Interactions, 3:69-71.

Hamuro et al., 1978, "Solid phase activation of alternative pathway of complement by β-1,3-gulcans and its possible role for tumor regressing activity", Immunology, 34:695-705.

Harada et al., 1997, "Oral Administration of PSK can Improve the Impaired Anti-Tumor CD4+ T-Cell Response in Gut-Associated Lymphoid Tissue (GALT) of Specific-Pathogen-Free Mice," Int. J. Cancer, 70:362-372.

Hellstrom, I. et al., 1986, "Antitumor effects of L6, and IgG2a antibody that reacts with most human carcinomas," Proc. Natl. Acad. Sci. USA, 83:7059-7063.

Herre et al., 2004, "Dectin-1 and its role in the recognition of β-glucans by macrophages," Mol. Immunol. 40(12):869-876.

Herrera et al., 2000, "Immunotoxins against CD19 and CD22 are effective in killing precursor-B acute lymphoblastic leukemia cells in vitro," Leukemia, 14:853-858.

Jamas et al., 1990, "Spectral Analysis of Glucan Produced by Wild-Type and Mutant *Saccharomyces cerevisiae*," Carbohydrate Polymers, 13:207-219.

Jani et al., 1990, "Nanoparticle uptake by the rat gastrointestinal mucosa: quantitation and particle size dependency," J. Pharm. Pharmacol. 42:821-826.

Kernodle et al., 1998, "Prophylactic Anti-Infective Activity of Poly-[1-6]-β-D-Glucopyranosyl-1[1-3]-β-D-Glucopyranose Glucan in a Guinea Pig Model of Staphylococcal Wound Infection," Antimicrobial Agents and Chemotherapy, 42(3):545-549.

Kim. Y.-S., et al., 2000, "Gram-negative Bacterial-binding Protein, a Pattern Recognition Receptor for Lipopolysaccharide and β-1,3-Glucan That Mediates the Signaling for the Induction of Innate Immune Genes in *Drosophila melanogaster* Cells," J. Biol. Chem. 275(42):32721-32727.

Kirby et al., 1981, "Oat-bran intake selectively lowers serum low-density lipoprotein cholesterol concentrations of hypercholesterolemic men", American Journal of Clinical Nutrition, 34:824-829.

Kotera, Y., et al., Jun. 1, 1994, "Humoral Immunity against a Tandem Repeat Epitope of Human Mucin MUC-1 in Sera from Breast, Pancreatic, and Colon Cancer Patients," Cancer Res., 54:2856-2860.

Maeda et al., 1971, "Lentinan, a new immune-accelerator of cell-mediated responses", Nature, 229:634.

Maloney et al., 1997, "IDEC-C2B8 (Rituximab)Anti-CD20 Monoclonal Antibody Therapy in Patients With Relapsed Low-Grade Non-Hodgkin's Lymphoma," Blood, 99(6):2188-2195.

Matzinger, P., 1994 "Tolerance, Danger, and the Extended Family," Annu. Rev. Immunol. 12:991-1045.

Mayell M. 2001 "Maitake Extracts and Their Therapeutic Potential—A Review," Altern. Med. Rev., 6(1):48-60.

Mendelsohn et al., 1988, "Monoclonal Antibodies Against the Receptor for Epidermal Growth Factor as Potential Anticancer Agents," Cellular and Molecular Biology of Tumors and Potential Clinical Applications, 307-312.

Mendelsohn J., 1997, "Epidermal Growth Factor Receptor Inhibition by a Monoclonal Antibody as Anticancer Therapy," Clin. Cancer Res. 3:2703-2707.

Nakao et al., 1983, "Clinical evaluation of schizophyllan (SPG) in advanced gastric cancer-a randomized comparative study by an envelope method," Gan To Kagaku Ryoho, 10: 1146-1159.

Nakazato et al., 1994, "Efficacy of immunotherapy as adjuvant treatment after curative resection of gastric cancer" The Lancet, 343:1122-1126.

Hiroaki Nanba and Kieko Kubo, 1997, "Effect of Maitake D-Fraction on Cancer Prevention," Annal. N.Y. Acad. Sci. 833:204-207.

Nicolosi et al., 1999, "Plasma lipid changes after supplementation with β-glucan fiber from yeast," Am. J. Clin. Nutr., 70:208-212.

Ohno et al., 2000, "Antitumor 1,3-β-Glucan from Cultured Fruit Body of *Sparassis crispa*," Biol. Pharm. Bull., 23(7):866-872.

Ollert et al., 1996, "Normal human serum contains a natural IgM antibody cytotoxic for human neuroblastoma cells," Proc. Natl. Acad. Sci. USA, 93:4498-4503.

Ollert et al., 1997, "Mechanisms of in vivo antineuroblastoma activity of human natural IgM," European Journal of Cancer, 33(12);1942-1948.

Onizuka et al., 1999, "Tumor Rejected by in Vivo Administration of Anti-CD25 (Interleukin-2 Receptor β) Monoclonal Antibody," Cancer Research, 59:3128-3133.

Oxford Textbook of Oncology, 1995, "Chemotherapy: General Aspects", Peckham, Pinedo and Veronesi, ed., vol. 1, 447-453.

Patchen et al., 1984, "Soluble Polyglycans Enhance Recovery from Cobalt-60-Induced Hemopoietic Injury", Journal of Biological Response Modifiers, 3:627-633.

Peat et al., 1958, "Polysaccharides of Baker's Yeast. Part II. Yeast Glucan", Journal Chem. Soc. Part 1, 3862-3868.

Rai, K.R. and Gupta, N., 2000, "Monoclonal Antibodies in Chronic Lymphocytic Leukemia," Rev. Clin. Exp. Hematol., 4.2:134-144.

Ren et al., 1997, "Mechanisms of Anti-Lung Cancer Activity for Monoclonol Antibody to Epidermal Growth Factor Receptor," Disi Junyi Daxue Xuebao, 18(6):560-562 (abstract only).

Robbins et al., 1977, "Cholesterol Lowering Effect of Dietary Yeast and Yeast Fractions", Journal of Food Science, 42 (3):694-698.

Saito et al., 1977, "A C-N.M.R.-spectral study of a gel forming, branched (1→3)-β-D-Glucan, (Lentinan) from Lentinus edodes, and its acid-degraded fractions. Structure, and Dependence of Confirmation on the Molecular Weight", Carbohydrate Research. 58:293-305.

Sasaki et al., 1976, "Antitumor Activity of Degraded Products of Lentinan: it's Correlation with Molecular Weight", Gann, 67:191-195.

Seljelid et al., 1977, "Glycan Stimulation of Macrophages in Vitro", Experimental Cell Research, 131:121-129.

Seljelid et al., 1986, "A water soluble aminated β-1,3-D-glucose derivative caused regression of solid tumors in mice", Bioscience Reports 6:845-852.

Singh et al., 1974, "Scleroglucan, an antitimor polysachharide from Sclerotium glucanicum", Carbohydrate Research, 37:245-247.

Slovin, S F. et. al., 1999, "Carbohydrate vaccines in cancer Immunogenicity of a fully synthetic globo H hexasaccharide conjugate in man," Proc. Natl. Acad. Sci. USA, 96:5710-5715.

Soiffer et al., 1997, "Administration of R24 Monoclonal Antibody and Low-Dose Interleukin 2 for Malignant Melanoma," Clinical Cancer Research, 3:17-24.

Torsu et al., 1990 "Significant prolongation of disease-free period gained by or polysaccharide K (PSK) administration after curative surgical operation of colorectal cancer," Cancer Immunology Immunotherapy, 31 (5):261-268.

Williams et al., 1991, "Development, physicochemical characterization and preclinical efficacy evaluation of a water soluble glucan sulfate derived from *Saccharomyces cerevisiae*," Immunopharmacology 22:139-155.

Zimmerman, J.W., et al., 1998, "A Novel Cabohydrate-Glycosphingolipid Interaction between a β-(1-3)-Glucan Immnomodulator, PGG-Glucan, and Lactosyceramide of Human Leukocytes," J. Biol. Chem., 273(34):22014-22020.

PCT International Preliminary Examination Report, Mar. 27, 2003, Sloan-Kettering Institute for Cancer Research, Int'l. Application No. PCT/US02/01276, Filed Jan. 15, 2002.

PCT International Search Report, Feb. 28, 2005, Sloan-Kettering Institute for Cancer Research, Int'l Application No. PCT/US04/23099, Filed Jul. 16, 2004.

(56) References Cited

OTHER PUBLICATIONS

PCT International Search Report, Apr. 14, 2005, Sloan-Kettering Institute for Cancer Research, Int'l Application No. PCT/US04/23099, Filed Jul. 16, 2004.
PCT Written Opinion of the International Searching Authority, Apr. 14, 2005, Sloan-Kettering Institute for Cancer Research, Int'l Application No. PCT/US04/23099, Filed Jul. 16, 2004.
PCT International Search Report, Jun. 5, 2012, Sloan-Kettering Institute for Cancer Research, Int'l Application No. PCT/US02/01276, Filed Jan. 15, 2002.
PCT Written Opinion, Nov. 25, 2002, Sloan-Kettering Institute Cancer Research, et al. Int'l Application No. PCT/US02/01276, Filed Jan. 15, 2002.
PCT International Preliminary Report on Patentability, Jan. 26, 2006, Sloan-Kettering Institute for Cancer Research, et al., Int'l Application No. PCT/US2004/023099, Filed Jul. 16, 2004.
PCT Corrected Written Opinion of the International Searching Authority, Aug. 10, 2005, Sloan-Kettering Institute for Cancer Research, et al, Int'l Application No. PCT/US04/23099, Filed Jul. 16, 2004.
PCT Corrected International Search Report, Aug. 10, 2005, Sloan-Kettering Institute for Cancer Research, et al, Int'l Application No. PCT/US2004/23099, Filed Jul. 16, 2004.
Search Report prepared by the Norwegian Patent Oifice, dated May 4, 2005.
Allendorf et al., 2004, "Macrophages shuttle orally administered β-glucan to potentiate the CR3-dependent tumoricidal effects of monoclonal antibodies in mouse tumor models", FASEB Journal, vol. 17, No. 7, C128.
Arturson, G. et al., 1966, "Intravascular Persistence and Renal Clearance of Dextran of Different Molecular Sizes in Normal Children", Arch. Dis. Childh., vol. 41, 168-172.
Arturson, G. and Wallenius, G., 1964, "The Renal Clearance of Dextran of Different Molecular Sizes in Normal Humans", Scandinaz J Clin & Lab Investigation, vol. 1, 81-86.
Babineau, T. et al., 1994, "A Phase II Multicenter, Double-blind, Randomized, Placebo-Controlled Study of Three Dosages of an Immunomodulator (PGG-Glucan) in High-Risk Surgical Patients", Arch. Surg., vol. 129, 1204-1210.
Babineau, T. et al., 1994, "Randomized Phase I/II Trial of a Macrophage-Specific Immunomodulator (PGG-Glucan) in High-Risk Surgical Patients", Annals of Surgery, vol. 220, No. 5, 601-609.
Cheung, N. and Modak, S., 2002, "Oral (1→3),(1→4)-β-D-Glucan Synergized with Antiganglioside GD2 Monoclonal Antibody 3F8 in the Therapy of Neuroblastoma", Clinical Cancer Research, vol. 8, 1217-1223.
Cheung, N.K. et al., 2002, "Orally administered β-glucans enhance anti-tumor effects of monoclonal antibodies", Cancer Immunol Immunother. 51(10):557-564.
Chihara, G. et al., 1987, "Antitumor and Metastasis-Inhibitory Activities of Lentinan as an Immunomodulator: An Overview", Cancer Detection and Prevention Supplement vol. 1, 423-443.
Dellinger, E. et al., 1999, "Effect of PGG-glucan on the Rate of Serious Postoperative Infection or Death Observed After High Risk Gastrointestinal Operations", Arch. Surg., vol. 134, 977-983.
Hanaue, H. et al., 1989, "Basic Studies on Oral Administration of Lentinan (I)", J. Jpn. Soc. Cancer Ther., vol. 8, 1566-1571.
Hanaue, H. et al., 1989, "Effects of oral lentinan on T-cell Subsets in Peripheral Venous Blood", Clin. Ther. 11:614-622.
Hayakawa, K. et al., 1993, "Effect of Krestin (PSK) as Adjuvant Treatment on the Prognosis after Radical Radiotherapy in Patients with Non-small Cell Lung Cancer", Anticancer Res. 13:1815-1820.
Hong et al., "Mechanism by Which Orally Administered β-1,3-Glucans Enhance the Tumoricidal Activity of Antitumor Monoclonal Antibodies in Murine Tumor Models", The Journal of Immunology, vol. 173, No. 5, pp. 797-806 (2004).
Hotta, H. et al., 1993, "Augmentation of protective immune responses against Sendai virus infection by fungal polysaccharide schizophyllan", Int. J. Immunopharmacol. 15:55-60.

Morinaga, H. et al., 1994, "An in vivo study of hepatic and splenic interleukin-1β mRNA expression following oral PSK or LEM Administration", Gann 85:1298-1303.
Nanba, H. et al., 1995, "Activity o Maitake D-faction to Inhiblt Carcinogensis and Metastasis", Ann N. Y. Acad. Sci. 768:243-245.
Nanba, H, and H. Kuroda, 1987, "Antitumor Mechanisms of Orally Administered Shiitake Fruit Bodies", Chem. Pharm. Bull. (Tokyo) 35:2459-2464.
Nanba, H. and H. Kuroda, 1988, "Potentiation of Host-Mediated Antitumor Activity by Orally Administered Mushroom (*Agaricus bispora*) Fruit Bodies", Chem. Pharm. Bill. (Tokyo) 36:1437-1444.
Hishida, I. et al., 1988, "Antitumor Activity Exhibited by Orally Administered Extract from Fruit Body of *Grifola frondosa* (Maitake)", Chem. Pharm. Bull (Tokyo) 313:1819-1827.
Iino, Y. et al., 1995, "Immunochemotherapies verus Chemotherapy as Adjuvant Treatment after Curative Resection of Operable Breast Cancer", Anticancer Res. 15:2907-2912.
Kidd, P., 2000, "The Use of Mushroom Glucans and Proteoglycans in Cancer Treatment", Alternative Medicine Review, vol. 5, No. 1, 4-27.
Mayer, L. and Shao, L., 2004, "Therapeutic Potential of Oral Tolerance", Nature Reviews Immunology, vol. 4, 407-419.
Mehvar, R., 2003, "Recent Trends in the Use of Polysaccharides for Improved Delivery of Therapeutic of Agents: Pharmacokinetic and Pharmacodynamic Perspectives", Current Pharmaceutical Biotechnology, vol. 4, 283-302.
Nanba, H. et al., 1987, "Antitumor action of shiitake (*Lentinus edodes*) fruit bodies orally administered to mice", Chem. Pharm. Bull. (Tokyo) 35:2453-2458.
Ohmori, T. et al., 1988. "Dissociation of a Glucan Fraction (CO-1) from Protein-bound Polysaccharide of Cordyceps ophioglossides and Analysis of its Antitumor Effect", Chem. Pharm. Bull. (Tokyo) 36:4512-4518.
Ostroff et al., 2003, "Immune-Enhancing Effects of Oral Yeast β 1,3/1,6 Glucans", American Chemical Society, vol. 225, No. 1-2, pp. AGFD 8.
Papila et al., 2004. "The Effect of Oral β-glucan in Addition to Systemic Chemotherapy on the Leukocyte Values and Oral Mucositis in the Patients with Head-neck Tumors", International Review of Allergology & Clinical Immunology, vol. 10, No. 2, 59-61.
Ross, et al., 1999, "Therapeutic intervention with complement and β-glucan in cancer", Immunopharmacology 42, 61-74.
Sakurai, T. et al., 1992, "Enhancement of Murine Alveolar Macrophage Functions by Orally Administered β-glucan", Int. J. Immunopharmacol. 14:821-830.
Shimazu, H. et al., 1980, "Intravenous chronic toxicity of lentinan in rats: 6-month treatment and 3-month recovery (author transl.)", National Library of Medicine (PubMed), J Toxicol Sci., 33-57.
Sortwell, R. et al., 1981, "Chronic Intravenous Administration of Lentinan to the Rhesus Monkey", Toxicology Letters, vol. 9, 81-85.
Suzuki, et al., 1990, "Effect of orally administered β-glucan on macrophage fuction in mice", Int. J. Immunopharmacology 12:6, 675-684.
Suzuki, M. et al., 1994, "Antitumor and Immunological Activity of Lentinan in Comparison with LPS", International Society for Immunopharmacology, pp. 463-468.
Suzuki, I. et al., 1989, "Immunomodulation by Orally Administered β-glucan in Mice", Int. J. Immunopharmacol 11:761-769.
Suzuki, I. et al., 1991 "Inhibition of Experimental Pulmonary Metastasis of Lewis Lung Carcinoma by Orally Administered β-glucan in Mice", Chem. Pharm. Bull. (Tokyo) 39:1606-1608.
Tsukagoshi, S. et al., 1984, "Krestin (PSK)", Cancer Treat. Rev. 11:131-155.
Vetvicka, et al. 2002, "Pilot Study: Orally-administrered Yeast Beta 1-3-glucan Prophylactically protects against anthrax infection and cancer in mice", Journ. Ameri. Nutraceutical Assoc., vol. 5:2.
Vetvicka, V. et al., 1996, "Soluble β-Glucan Polysaccharide Binding to the Lectin Site of Neutrophil or Natural Killer Cell Complement Receptor Type3(CD11b/CD18) Generates a Primed State of the Receptor Capable of Mediating Cytotoxicity of iC3b-Opsonized Target Cells", J. Clin. Invest., 98:50-61.
Xia, Y. et al., 1999, "The β-Glucan-Binding Lectin Site of Mouse CR3 (CD11b/CD18) and Its Function in Generating a Primed State of

(56) References Cited

OTHER PUBLICATIONS the Receptor That Mediates Cytotoxic Activation in Response to IC3b-Opsonized Target Cells", J. Immunology, 162:2281-2290.
Yan, J. et al., 1999, "β-Glucan, a "Specific" Biologic Response Modifier That Uses Antibodies to Target Tumors for Cytotoxic Recognition by Leukocyte Complement recpetor Type 3 (CD11b/CD18)". The Journal of Immunology, 163:3045-3052.
Basic and Clinical Pharmacology, 1998, 7th edition, Bertram G. Katzung, pp. 881-884.
U.S. Office Action, Mar. 5. 2008, for Nai-Kong V. Cheung, U.S. Appl. No. 11/334,763, filed Jan. 17, 2006.
U.S. Office Action, Dec. 17, 2008, for Nai-Kong V. Cheung, U.S. Appl. No, 10/565,484, filed Jan. 17, 2006.
Chinese Office Action, Oct. 31, 2008, for Sloan-Kettering Institute for Cancer Research, Chinese Application No. 200480020356.6, Filed Jan. 16, 2006, correspoding to PCT/US04/23099.
Australian Office Action, Dec. 4, 2008, for Sloan-Kettering Institute for Cancer Research, Australian Application No. 2008207369, Filed Aug. 18, 2008, continuation-in-part of PCT/US07/01427.
Chan et al., 2007 "Response of human dendritic cells to different immunomodulatory polysaccharides derived from mushroom and barley", International Immunology, 19(7): 891-899.
Cheung et al., 1994, "Antibody response to murine anti-GD2 monoclonal antibodies: correlation with patient survival", Cancer research, 54(8):2228-2233.
Cheung et al., 2006. "FCGR2A polymorphism is correlated with clinical outcome after immunotherapy of neuroblastoma with anti-GD2 antibody and granulocyte macrophage colony-stimulating factor", J. Clinical Oncology, 24(18): 2885-2890.
Dhodapkar et al., 2002, "Antitumor monoclonal antibodies enhance cross-presentation ofoCellular antigens and the generation of myeloma-specific killer T cells by dendritic cells", J. Experimental Medicine, 195(1): 125-133.
Diaz De Stahl et al., 2003, "A role for complement in feedback enhancement of antibody responses by IgG3", J. Experimental Medicine, 197(9): 1183-1190.
Dillman, R.O., 2001, "Monoclonal antibodies in the treatment of malignancy: basic concepts and recent developments", Cancer Investigation, 19(8): 833-841.
Hong et al., 2003, "Beta-glucan functions as an adjuvant for monoclonal antibody immunotherapy by recruiting tumoricidal granulocytes as killer cells", Cancer research, 63(24): 9023-9031.
Iannello et al., 2005, "Role of antibody-dependent cell-mediated cytotoxicity in the efficacy of therapeutic anti-cancer monoclonal antibodies", Cancer Metastasis Reviews, 24(4); 487-499.
Imai et al., 2005, "Complement-mediated mechanisms in anti-GD2 monoclonal antibody therapy of murine metastatic cancer", Cancer Research, 65(22): 10562-10568.
Kushner et al., 2001, "Phase II trial of the anti-G(D2) monoclonal antibody 3F8 and granulocyle-macrophage colony-stimulating factor for neuroblastoma", J. Clin. Oncol. 19(22):4189-94.
Yoshitomi et al., 2005, "A role for fungal (beta)-glucans and their receptor Dectin-1 in the induction of autoimmune arthritis in genetically susceptible mice", J. Experimental Medicine, 201(6):949-960.
Zhang et al., 1998, "Antibodies against GD2 ganglioside can eradicate syngeneic cancer micromelastases", Cancer Research, 58(13): 2844-2849.
Supplementary European Search Report, Dec. 11, 2009, for Sloan-Kettering Institute for Cancer Research, European Application No. EP 04786081.
Canadian Office Action, Dec. 6, 2010, for Sloan-Kettering Institute for Cancer Research, Canadian Application No. 2,434,938, Filed Jul. 15, 2003, National State of PCT/US02/01276, Filed Jan. 15, 2002.
Canadian Office Action, May 31, 2010, for Sloan-Kettering Institute for Cancer Research, Canadian Application No. 2,536,632, Filed Jan. 13, 2006, National State of PCT/US04/23099, Filed Jul. 16, 2004.
Canadian Office Acton, Jan. 25, 2010, for Sloan-Kettering Institute for Cancer Research, Canadian Application No. 2,434,933, Filed Jul. 15, 2003, National Stage of PCT/US02/01276, Filed Jan. 15, 2002.
Canadian Office Action, Oct. 29, 2009, for Sloan-Kettering Institute for Cancer Research, Canadian Application No. 2,536,632, Filed Jan. 13, 2006, National Stage of PCT/US04/23099, Filed Jul. 16, 2004.
Canadian Office Action, Mar. 26, 2009, for Sloan-Kettering Institute for Cancer Research, Canadian Application No. 2,434,938, Filed Jul. 15, 2003, Nationai Stage of PCT/US02/01276.
Chinese Rejection Decision, Jan. 29, 2010, for Sloan-Kettering Institute for Cancer Research, Chinese Application No. 200480020356.6, Filed Jan. 16, 2006, National Stage of PCT/US04/23099, Filed Jul. 16, 2004 (with English translation).
Chinese Office Action, Jul. 24, 2009, for Sloan-Kettering Institute for Cancer Research, Chinese Application No. 200480020356.6, Filed Jan. 16, 2006, National Stage of PCT/US04/23099.
Chinese Office Action, Feb. 27, 2009, for Sloan-Kettering Institute for Cancer Research, Chinese Application No. 200480020356.6, Filed Jan. 16, 2006, National Stage of PCT/US04/23099.
European Office Action, Jan. 26, 2011 for Sloan-Kettering Institute for Cancer Research, European Application No. 02 707 502.7, Filed Aug. 4, 2003, National Stage of PCT/US02/01276, Filed Jan. 15, 2002.
European Office Action, Apr. 6, 2010, for Sloan-Kettering Institute for Cancer Research, European Application No. 04786081.2, Filed Apr. 18, 2006, National Stage of PCT/US04/23099, Filed Jul. 16, 2004.
European Office Action, Oct. 21, 2009, for Sloan-Kettering Institute for Cancer Research, European Application No. 02 707 502.7, Filed Aug. 4, 2003, National Stage of PCT/US02/01276, Filed Jan. 15, 2002.
European Office Action, Mar. 30, 2009, for Sloan-Kettering Institute for Cancer Research, European Application No. 02 707 502.7, Filed Aug. 4, 2003, National Stage of PCT/US02/01276.
Indian First Examination Report, Feb. 12, 2009, for Sloan-Kettering Institute for Cancer Research, Indian Application No. 186/MUMNP/2006, Filed Feb. 15, 2006, corresponding to PCT/US04/23099.
Japanese Office Action, Jan. 7 2011, for Sloan-Kettering Institute for Cancer Research, Japanese Application No. 2006-520398, Filed Jan. 16, 2006, national stage of Int'l App'l No. PCT/US04/23099, Filed Jul. 16, 2004.
Mexican Office Action, Mar. 25, 2010, for Sloan-Kettering Institute for Cancer Research, Mexican Application No. PA/a/2006/000615, Filed Jan. 16, 2006, National Stage of PCT/US04/23099, Filed Jul. 16, 2004, (with English translation).
Mexican Office Action, Sep. 18, 2009, for Sloan-Kettering Institute for Cancer Research, Mexican Application No. Pa/a/2006/000615, Filed Jan. 16, 2006, National Stage of PCT/US04/23099, Filed Jul. 16, 2004. (with English translation).
Mexican Office Action, May 29, 2009, for Sloan-Kettering Institute for Cancer Research, Mexican Application No. PA/a/2006/000615, Filed Jul. 16, 2004, National Stage of PCT/US04/23099.
U.S. Office Action, May 27, 2010, for Rolf Einar Engstad, U.S. Appl. No. 12/161,285, filed Jul. 17, 2008.
U.S. Office Action, Nov. 10, 2009, for Nai-Kong V Cheung, U.S. Appl. No. 12/161,285, filed Jul. 17, 2008.
U.S. Advisory Action, Aug. 6, 2009, for Nai-Kong V. Cheung, U.S. Appl. No. 12/036,462, filed Feb. 25, 2008.
U.S. Advisory Action, Jul. 10, 2009, for Nai-Kong V. Cheung, U.S. Appl. No. 12/036,462, filed Feb. 25, 2008.
U.S. Office Action, Jun. 16, 2009, for Nai-Kong V. Cheung, U.S. Appl. No. 10/565,484, filed Jan. 17, 2006.
U.S. Office Action, Apr. 17, 2009, for Nai-Kong V. Cheung, U.S. Appl. No. 12/036,462, filed Feb. 25, 2008.
U.S. Office Action, Oct. 24, 2008, for Nei-Kong V. Cheu Ng, U.S. Appl. No. 12/036,462, filed Feb. 25, 2008.
U.S. Office Action, Aug. 11 2008, for Nai-Kong V. Cheung, U.S. Appl. No. 10/565,464, filed Jan. 17, 2006.
Andoh, T., 1992, "Effects of Pervenous Administration of Lentinan and Concomitant Perendoscopic Localized Injection on Gastric Carcinoma in Elderly Patients", Nichidai Igaku Zasshi, 51(6):587-596, (abstract only).
Hamuro, Junji, 2005, "Anticancer immunotherapy with perorally effective Lentinan", Cancer & Chemotherapy, 32(8):1209-1215. (abstract only).

(56) References Cited

OTHER PUBLICATIONS

Herlyn et al., 1985, Stimulation of monoclonal antibody-dependent rnacrophage-mediated cytotoxicity against human tumors by lentinan, International Journal of Immunopharmacology, 7(3):332. (abstract only).
Kaneko et al., 1989, Activity of Lentinan against Cancer and AIDS, International Journal of Immunotherapy, 5(4):203-123.
Lehne et al., 2005, "Oral administration of a new soluble branched β-1,3-D-glucan is well tolerated and can lead to increased salivary concentration of immunoglobulin A in healthy volunteers", Clinical and Experimental Immunology, 143:65-69.
Pelley, R.P. and Strickland, F.M., 2000, "Plants, polysaccharides, and the treatment and prevention of neoplasia", Critical Reviews in Oncogenesis, 11(3-4):189-225.
Penna eta al., 1996, "Pulmonary Metastases Neutralization and Tumor Rejection by In Vivo Administration of Beta Glucan and Bispecific Antibody", International Journal of Cancer, 65:377-382.
Sano et al., 2002, "Antitumor Effects Induced by the Combination of TNP-470 as an Angiogenesis Inhibitor and Lentinan as a Biological Response Modifier in a Rabbit Spontaneous Liver Metastasis Model", Surgery Today. 32:503-509.
Shio et al., 1977, "A study of the condition of additive use of immunotherapeutic agent, Lentinan, and chemotherapeutic agent, cyclophosphamide", Journal of Japan Society for Cancer Therapy, 15:436. (abstract only).
Takita et al., 1998, "Successful treatment of hepatic metastasis of gastric cancer with 5'-DFUR and Lentinan", Cancer & Chemotherapy, 25(1):129-133. (abstract only).
Allendorf et al., 2005, "C5a-Mediated Leukotriene B4-Amplified Neutrophil Chemotaxis is Essential in Tumor Immunotherapy Facilitated by Anti-Tumor Monoclonal Antibody and β-Glucan", Journal of Immunology, 174:7050-7056.
Gelderman et al., 2004, "Complement function in mAb-mediated cancer immunotherapy", TRENDS in Immunology, 25(3):158-164.
Li et al., 2007, "Combined Yeast β-Glucan and Antitumor Monoclonal Antibody Thearpy Requires C5a-Mediated Neutrophil Chemotaxis via Regulation of Decay-Accelerating Factor CD55", Cancer Research, 67:7421-7430.
Yan et al., 2005, "Yeast whole glucan particle β-glucan in conjuction with antitumor monoclonal antibodies to treat cancer", Expert Opinion on Biological Therapy, 5(5):691-702.
Japanese Office Action, May 6, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.
Korean Office Action, Apr. 12, 2011, for Sloan-Kettering Institute for Cancer Research, Korean Application No. 10-2006-7000839, Filed Jan. 13, 2006, National Stage of Int'l App'l No. PCT/US04/23099, Filed Jul. 16, 2004.
Canadian Office Action, Jan. 27, 2012, for Sloan-Kettering Institute for Cancer Research, Canadian Application No. 2,637,205, Filed Oct. 28, 2008, National Stage of PCT/US07/001427, Filed Jan. 17, 2007.
Chinese Office Action, Nov. 2, 2011, for Sloan-Kettering Institute for Cancer Research, Chinese Application No. 2007800075400, Filed Sep. 2, 2008, National Stage of Int'l App'l No. PCT/US07/01427, Filed Jan. 17, 2007.
Japanese Office Action, Aug. 26, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.
U.S. Office Action, Sep. 27, 2011, for Rolf Einar Engstad, U.S. Appl. No. 12/161,285, filed Jul. 17, 2008.
U.S. Office Action, Sep. 27, 2011, for Nai-Kong V. Cheung and Rolf Einar Engstad, U.S. Appl. No. 12/212,352, filed Sep. 17, 2008.
European Office Action, May 3, 2012, for Sloan-Kettering Institute for Cancer Research, European Application No. 07 71 8218, National Stage of PCT/US04/23099, Filed Jul. 16, 2004.
European Office Action, Apr. 5, 2012, for Sloan-Kettering Institute for Cancer Research, European Application No. 04 78 6081, Filed Jul. 16, 2008, National Stage of PCT/US07/01427, Filed Jan. 17, 2007.
Japanese Office Action, Jul. 13, 2012, for Sloan-Kettering Institute for Cancer Research, Japanese Application No. 2008-551413, Filed Jul. 16, 2008, National stage of Int'l App'l No. PCT/US07/01427, Filed Jan. 17, 2007.
U.S. Office Action, Mar. 13, 2012, for Rolf Einar Engstad and Nai-Kong V. Cheung, U.S. Appl. No. 12/161,285, filed Jul. 17, 2008.
U.S. Office Action, Mar. 7, 2012, for Nai-Kong V. Cheung and Rolf Einar Engstad, U.S. Appl. No. 12/212,352, filed Sep. 17, 2008.
U.S. Office Action, Jul. 27, 2012, for Nai-Kong V. Cheung, U.S. Appl. No. 12/212,352, filed Sep. 17, 2008.
U.S. Office Action, Jul. 18, 2012, for Nai-Kong V. Cheung, U.S. Appl. No. 12/814,174, filed Jun. 11, 2010.
U.S. Office Action, May 29, 2012, for Nai-Kong V. Cheung, U.S. Appl. No. 12/767,237, filed Apr. 26, 2012.
Ara et al., 2001, "Zymosan enhances the immune response to DNA vaccine for human immunodeficiency virus type-1 through the activation of complement system", Immunology, 103: 98-105.
Azuma, Ichiro, 1987, "Development of Immunostimulants in Japan", Immunostimulants: Now and Tomorrow, 41-56.
Gawronski et al., 1999, "Microfibrillar Structure of PCG-Glucan in Aqueous Solution as Triple-Helix Aggregates by Small Angle X-Ray Scattering", Biopolymers, 50: 569-578.
Hamaza et al., 2009, "Efficacy of Orally Administered Superfine Dispersed Lentian (β-1,3-Glucan) for the Treatment of Advanced Colorectal Cancer", Anticancer Research, 29: 261.
Hsu, Frank and Komarovskaya, Marina, 2002, "CTLA4 Blockade Maximizes Antitumor T-Cell Activation by Dendritic Cells Presenting Idiotype Protein or Opsonized Anti-CD20 Antibody-Coated Lymphoma Cells", Journal of Immunology, 25(6): 455-468.
Jamas et al., 1991, "PGG-Glucans", Polymeric Drugs and Drug Delivery Systems, American Chemcal Society Symposium Series,, 5: 44-51.
Komatsu et al., 1975, "Influence of Schizophyllan, Streptomycin and Rifampicin on Histopathological changes in mice infected in Tubercle Bacilli", Japanese Journal of Antibiotics, XXVII(4):549-557. (English abstract included).
Onrust et al., 1999, "Rituximab", Drugs, 58(1):79-88 (abstract only).
Song et al., 1979, "Yeast glucan and immunotherapy of infectious diseases", In: Lyosomes in Applied Biology, Dingle et al., Amsterdam, chapter 18, 533-545.
European Office Action, Aug. 17, 2012, for Sloan-Kettering Institute for Cancer Research, European Application No. 02 707 502.7, National Stage of PCT/US02/01276, Filed Jan. 15, 2002.
U.S. Office Action, Dec. 10, 2012, for Nai-Kong V. Cheung, U.S. Appl. No. 12/814,174, filed Jun. 11, 2010.
U.S. Advisory Action, Feb. 22, 2013, for Nai-Kong V. Cheung, U.S. Appl. No. 12/814,174, filed Jun. 11, 2010.
U.S. Advisory Action, Mar. 21, 2013, for Nai-Kong V. Cheung, U.S. Appl. No. 12/814,174, filed Jun. 11, 2010.
U.S. Office Action, Nov. 6, 2012, for Nai-Kong V. Cheung, U.S. Appl. No. 12/767,237, filed Apr. 26, 2012.
U.S. Office Action, Jul. 15, 2013, for Nai-Kong V. Cheung, U.S. Appl. No. 13/859,096, filed Apr. 9, 2013.

\* cited by examiner

Figure: 19

THERAPY-ENHANCING GLUCAN

This application is a continuation of U.S. application Ser. No. 12/036,462, now abandoned, filed Feb. 25, 2008, which is a continuation of U.S. application Ser. No. 11/218,044, now U.S. Pat. No. 7,462,607, filed Aug. 31, 2005, which is a continuation of U.S. application Ser. No. 10/621,027, now U.S. Pat. No. 7,507,724, filed Jul. 16, 2003, which is a continuation in part of PCT application PCT/US02/01276, filed Jan. 15, 2002, which claims benefit of provisional application 60/261,911, filed Jan. 16, 2001

Throughout this application, various references are cited. Disclosures of these publications in their entireties are hereby incorporated by reference into this application to more fully describe the state of the art to which this invention pertains.

BACKGROUND OF THE INVENTION

Monoclonal antibodies (MoAb) selective for tumors have therapeutic potential.[1,2] he introduction of hybridoma technology by Kohler and Milstein in 1975[3] and the advances in molecular biologic techniques have greatly expanded the potential of MoAb in human cancers. Anti-CEA antibody in colorectal cancer,[4] anti-CD20 antibodies in lymphoma,[5] anti-HER2 antibodies in breast cancer,[6] anti-tenascin antibodies in glial brain tumors,[7] MoAb M195 against CD33 in acute leukemia[8] and anti-TAG-72 antibodies in colon cancer[9] have shown efficacy in clinical trials. Our laboratory has developed the MoAb 3F8 which targets the ganglioside GD2 overexpressed on neuroblastoma. 3F8 has been shown to have a high specificity and sensitivity in the radioimmunodetection of minimal residual disease (MRD) in patients with NB,[10] and a significant impact when used as adjuvant therapy.[11]

The immune basis of clinical tumor response to MoAb is at least two fold, direct cytotoxicity and induced immunity. Antibody dependent cell-mediated cytotoxicity (ADCC) and complement-mediated cytotoxicity (CMC) are responsible for the direct killing of tumor cells. On the other hand, through tumor opsonization[12] or idiotype network,[13] tumor-specific immunity is induced. With this paradigm, how the body eliminates microbial pathogens remains highly relevant in our strategic approach to cancer therapy. Since the first description of innate immunity and acquired immunity model, several components have emerged center stage.[14] Antibodies, complement, phagocytes, and "danger" receptors are core elements of innate immunity while antigen-presenting cells, T and B lymphocytes constitute essential players in acquired immunity. Despite the availability of tumor-selective monoclonal antibodies and the ample supply of phagocytes/natural killers, shrinkage of established tumors following antibody treatment alone, and the acquisition of specific immunity, are not common in both preclinical models and cancer patients. The absence of a danger signal and the diminution of complement action by complement resistance proteins on tumor cells may explain the inefficiency of antibody mediated clinical responses.[15] LPS and beta-glucan, being cell wall components of bacteria and fungus, respectively, are potent danger signals to the immune systems in all life-forms, from Drosophila to man.[16] While LPS is too toxic for human use, β-glucan is a relatively benign structural component extractable from cereals, mushrooms, seaweed and yeasts.[17] They are made up of 1,3-β-D-glucopyranosyl residues along which are randomly dispersed single β-D-glucopyranosyl units attached by 1,6-linkages, giving a comb-like structure. The 1,3-β-backbone and the 1,6-linked branches were thought to be important for their immune effects. Lentinan (from *Lentinus edodes, Basidiomycete* family) with 1,6 branches at mean of 3 main chain units, is licensed Japan for cancer treatment. Schizophyllan (from *Schizophyllum commune, Basidiomycete* family) and β-glucan from Baker's yeast (*Saccharomyces cerevisiae*) have also similar structures. From seaweed, Laminarin (1,3 β-D-glucan with 1,6-β side chain branching on every 10 glucose subunit along the polymer backbone) has been extracted. Because of its smaller size and water solubility, it was thought to have potential biologic utility. On the other hand β-glucan from barley, oat or wheat have mixed 1,3-β and 1,4-β-linkage in the backbone, but no 1,6-β branches, and generally higher molecular weights and viscosities. In addition, they have not yet been tested for their in vivo immunomodulatory effects in cancer models.

This invention discloses that oral beta-glucans derived from barley or oats can greatly enhance the anti-tumor activity of anti-tumor monoclonal antibodies in xenograft models. Given the low toxicity of oral β-glucan, their role in cancer therapy deserves careful study.

SUMMARY OF THE INVENTION

This invention provides a composition comprising an effective amount of glucan capable of enhancing efficacy of antibodies. In an embodiment, the antibody is a monoclonal antibody. In a further embodiment, the antibody is an antibody against cancer.

The cancer is recognized by antibodies, and which includes but not limited to neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer colon cancer, liver cancer, stomach cancer, and other gastrointestinal cancers.

This invention further provides the above compositions and a pharmaceutically acceptable carrier, thereby forming pharmaceutical compositions.

This invention also provides a method for treating a subject with cancer comprising administrating the above-described composition to the subject.

This invention provides a composition comprising effective amount of glucan capable of enhancing efficacy of vaccines. In an embodiment, the vaccine is against cancer. This invention also provides the above compositions and a pharmaceutically acceptable carrier, thereby forming a pharmaceutical composition.

This invention also provides a method of treating a subject comprising administrating the above pharmaceutical composition to the subject. In an embodiment, the subject is a human subject. In an embodiment, the vaccine is against infectious agents. The infectious agents include but are not limited to bacteria, viruses, fungi, or parasites.

This invention provides a composition comprising effective amount of glucan capable of enhancing efficacy of natural antibodies. In an embodiment, the antibodies are against cancer. In another embodiment, the antibodies are against infectious agents. The infectious agents include but are not limited to bacteria, viruses, fungi, or parasites.

This invention provides a composition comprising effective amount of glucan capable of enhancing host immunity. In another embodiment, the immunity is against cancer or infectious agents.

This invention also provides a composition comprising effective amount of glucan capable of enhancing the action of an agent in preventing tissue rejection. In another embodiment, the tissue is transplanted tissue or transplanted organ. In another embodiment, the tissue is the host as in graft-versus-host reactions.

This invention also provides the above compositions, wherein the glucan are. 1,3-1,4 mixed linkage, without 1,6 branches.

The invention further provides the above compositions, wherein the glucan is of high molecular weight. In an embodiment, the molecular weight of the glucan ranges from 250,000 to 450,000 daltons. This invention provides the above compositions, wherein the glucan is derived from barley, oat, wheat or moss.

This invention provides the above compositions, wherein the glucan is stable to heat treatment. In an embodiment, the composition is stable after boiling for 3 hours.

This invention provides the above compositions, wherein oral route is adopted when taken into a subject. In an embodiment, the effective dose is about >=25 mg/kg/day, five days a week for a total of 2-4 weeks.

DETAILED DESCRIPTION OF THE FIGURES

First Series Of Experiments

FIG. 1. Synergistic effect of MoAb and β-glucan in LAN-1 Two million LAN-1 neuroblastoma cells were xenografted subcutaneously in Balb/c athymic mice. Treatment started in groups of 5 mice each, 2 weeks after tumor implantation when visible tumors reached 0.7-0.8 cm diameter. 3F8 group (solid circles) was treated with 200 ug of intravenous 3F8 injected through the retroorbital plexus twice weekly (M and Th). 3F8+BG group (open circle) was treated with 200 ug i.v. 3F8 twice weekly plus oral Barley β-glucan (BG medium viscosity) 400 ug daily by gavage for a total of 21 days. BG group (open triangle) received β-glucan alone, 400 ug po daily for 21 days. Tumor size was measured from the first day of treatment, and the product of the largest diameters expressed as percent of that on day 0 of treatment. While BG alone and 3F8 alone showed no anti-tumor effect, the BG+3F8 group showed highly significant tumor shrinkage and suppression ($p<0.001$).

Figure 2:
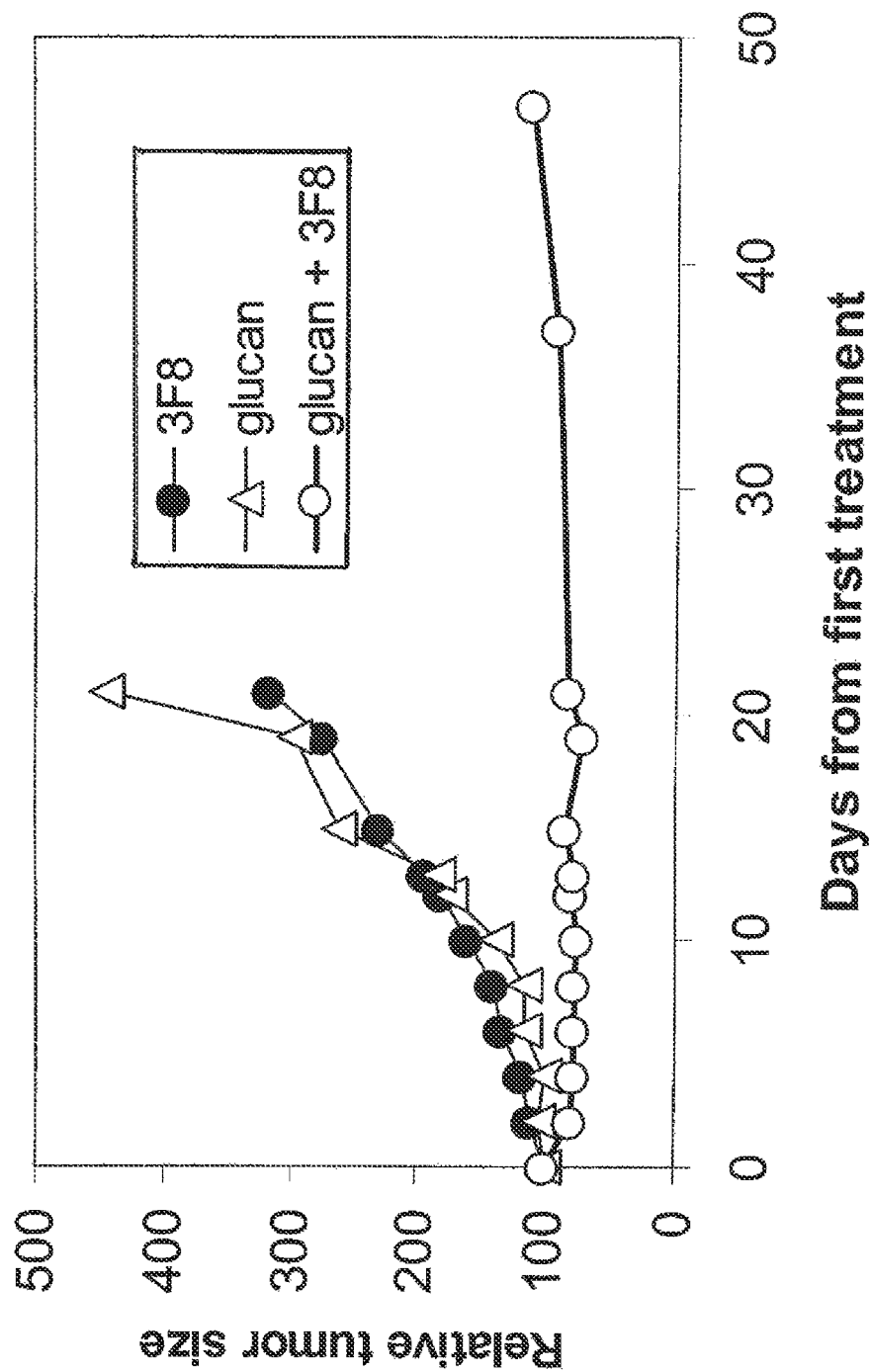

FIG. 2. Synergistic effect of MoAb and β-glucan in NMB-7 Experiment in FIG. 1 was repeated with the neuroblastoma cell line NMB7, a slower growing line. Again BG alone (open triangle) and 3F8 alone (solid circles) showed no anti-tumor effect, the BG+3F8 group (open circle) showed highly significant tumor shrinkage and suppression ($p<0.001$). Y-axis is relative tumor size in percent and X-axis the number of days from first treatment.

Figure 3:
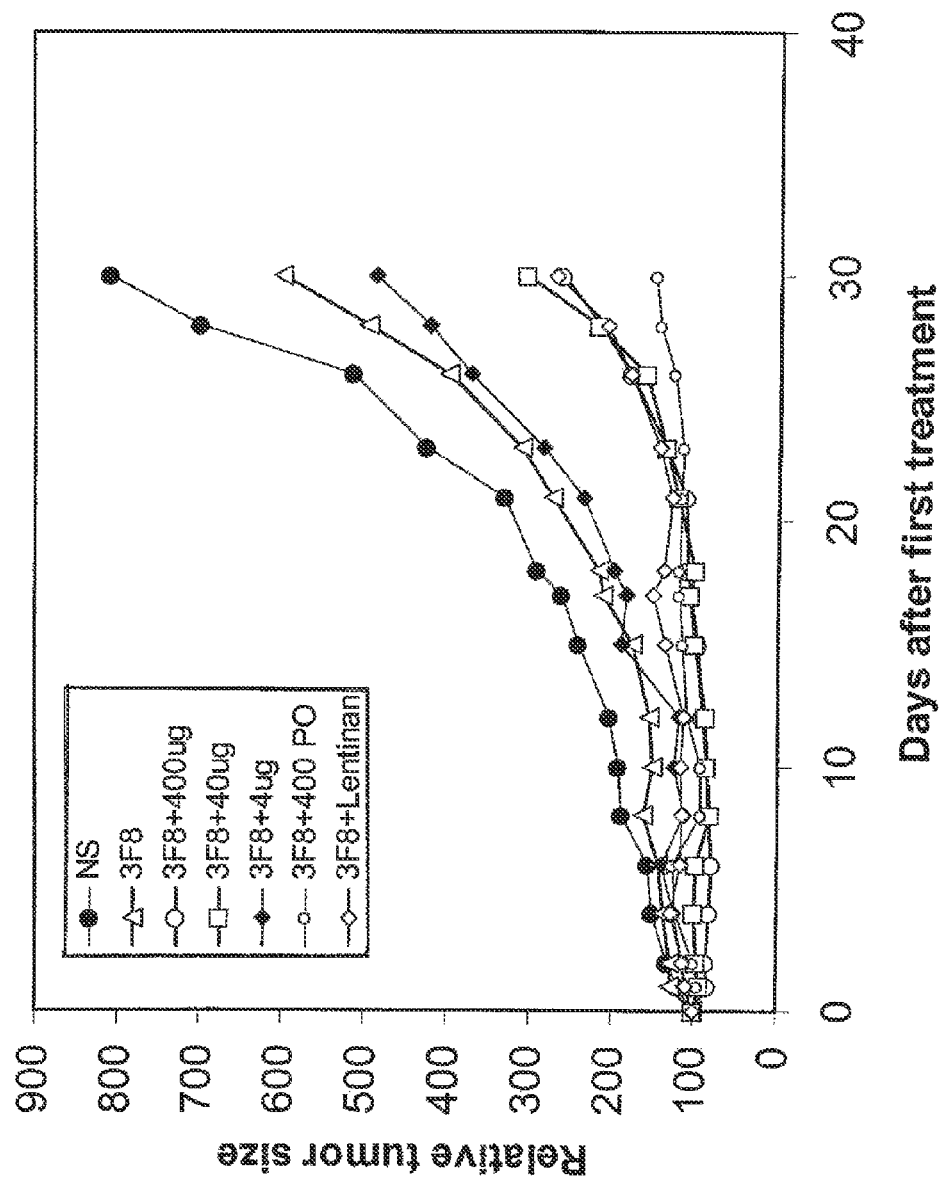

FIG. 3. Dose response of intraperitoneal (ip) β-glucan Two million NMB-7 xenografted nude mice were treated at the time of visible tumors with 3F8 alone, normal saline control, or 3F8 plus increasing doses of intraperitoneal BG (4 ug [solid diamond], 40 ug [open square], 400 ug [large open circle]) or 400 ug of po BG [small open circle], or 400 ug of ip Lentinan [open diamond]. Highly significant tumor shrinkage and suppression was shown in the combination groups except at 4 ug of BG dose. Oral BG appeared to be more effective than ip BG.

Figure 4:
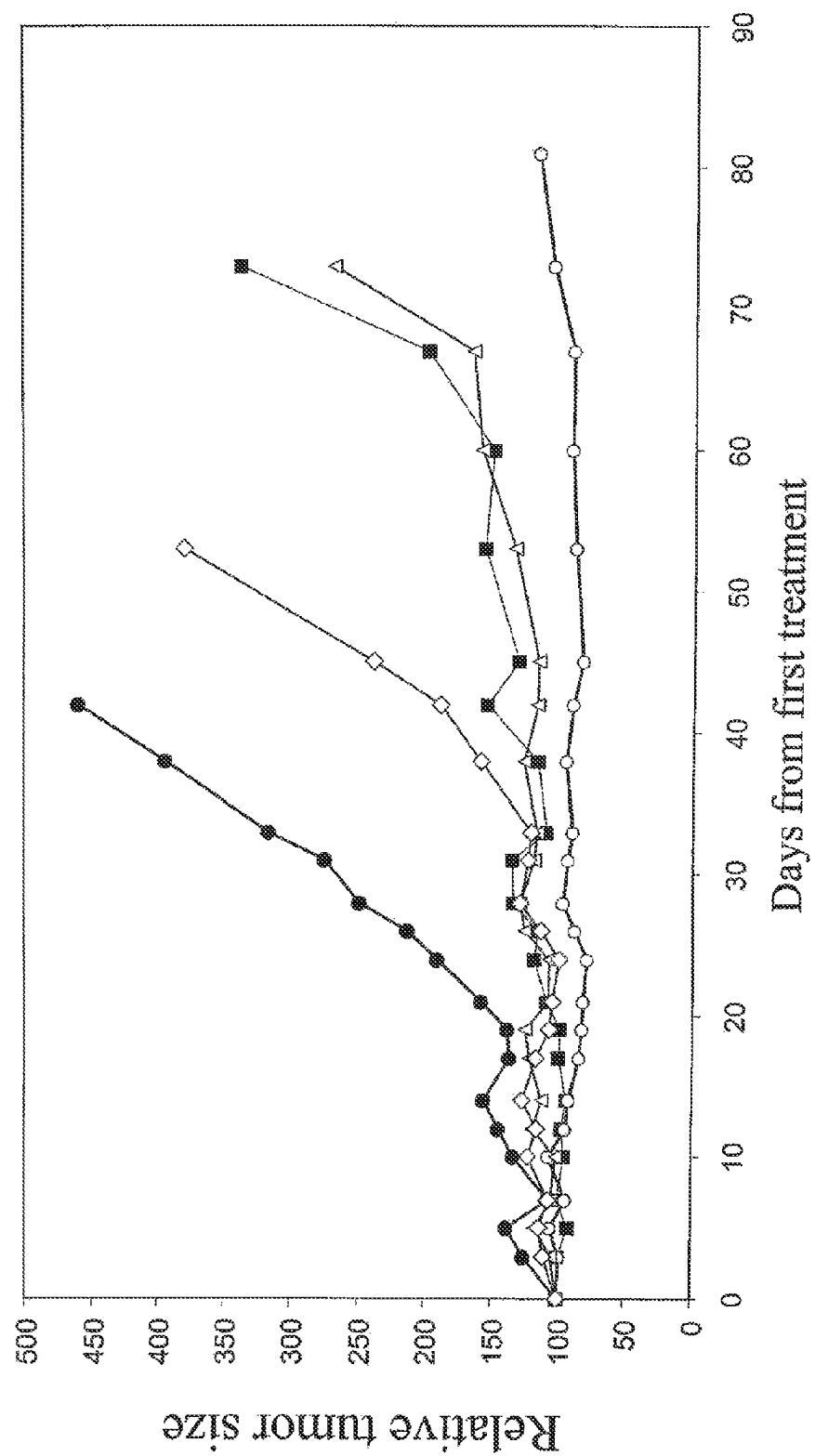

FIG. 4. Dose response of oral β-glucan NMB-7 xenografted in nude mice were treated as in FIG. 3 except that dose response of oral β-glucan (4 ug [open diamond], 40 ug [open triangle], 400 ug [open circle]) was compared to 400 ug of ip BG [solid square]. Control group received saline [solid circle]. 400 ug po was again highly significant in eradicating or suppressing tumor growth. 400 ip appeared to be as effective as 40 ug po. 4 ug was the least effective.

Figure 5:
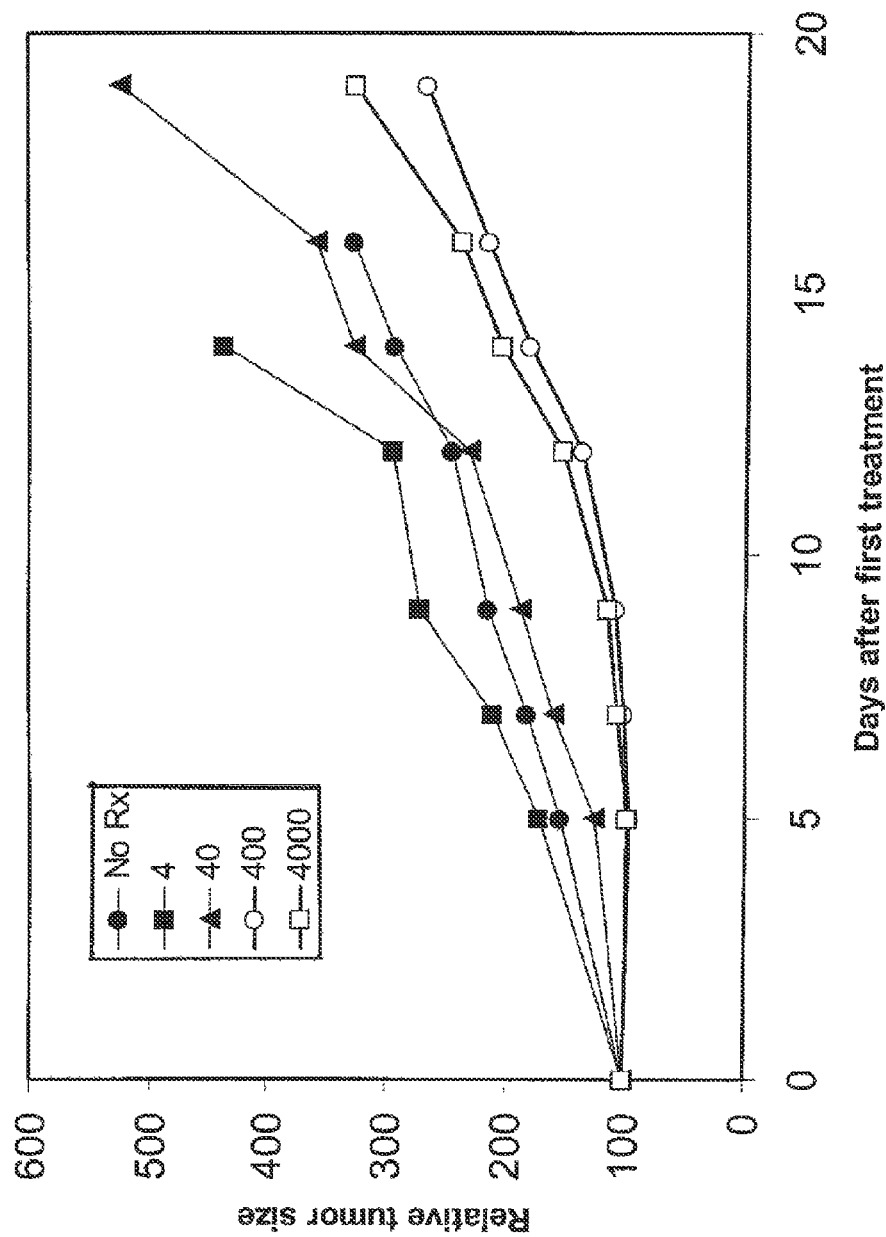

FIG. 5. Dose response of oral β-glucan in LAN-1 Five million LAN-1 cells were planted subcutaneously. Tumor growth was more rapid compared to 2 million NMB-7 cells. Again 4 ug [solid squares], 40 ug [solid triangle] were no different from controls. Only 400 ug po [open circle] and 4000 ug po [open square] showed significant tumor eradication or suppression.

Figure 6:
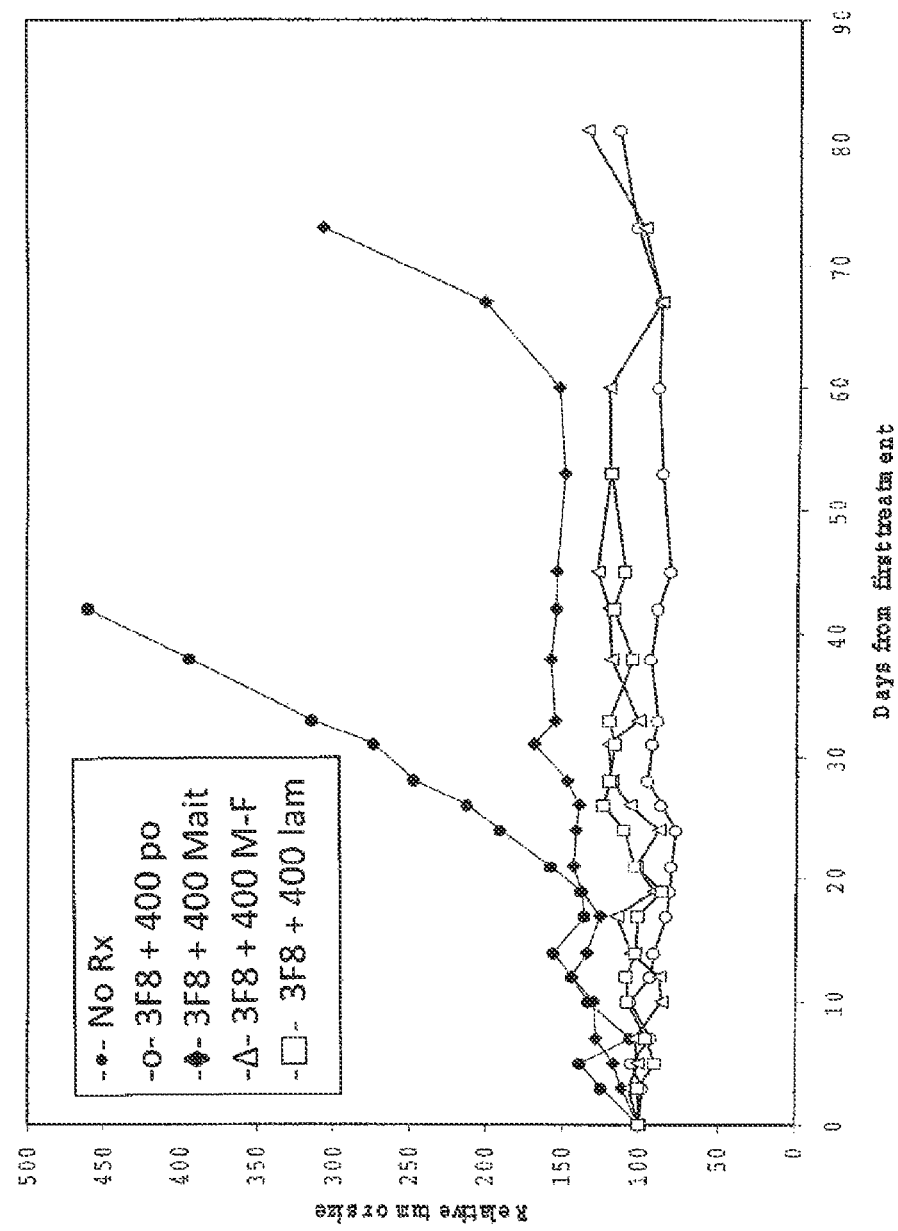

FIG. 6. Comparison of various β-glucans β-glucan [400 ug po qd] derived from barley [7 days/wk open circle, M-F/week open triangle], Maitake mushrooms [solid triangles], laminarin [open squares] were compared in their synergism with antibody 3F8 against NMB-7 subcutaneous xenografts.

Figure 7:
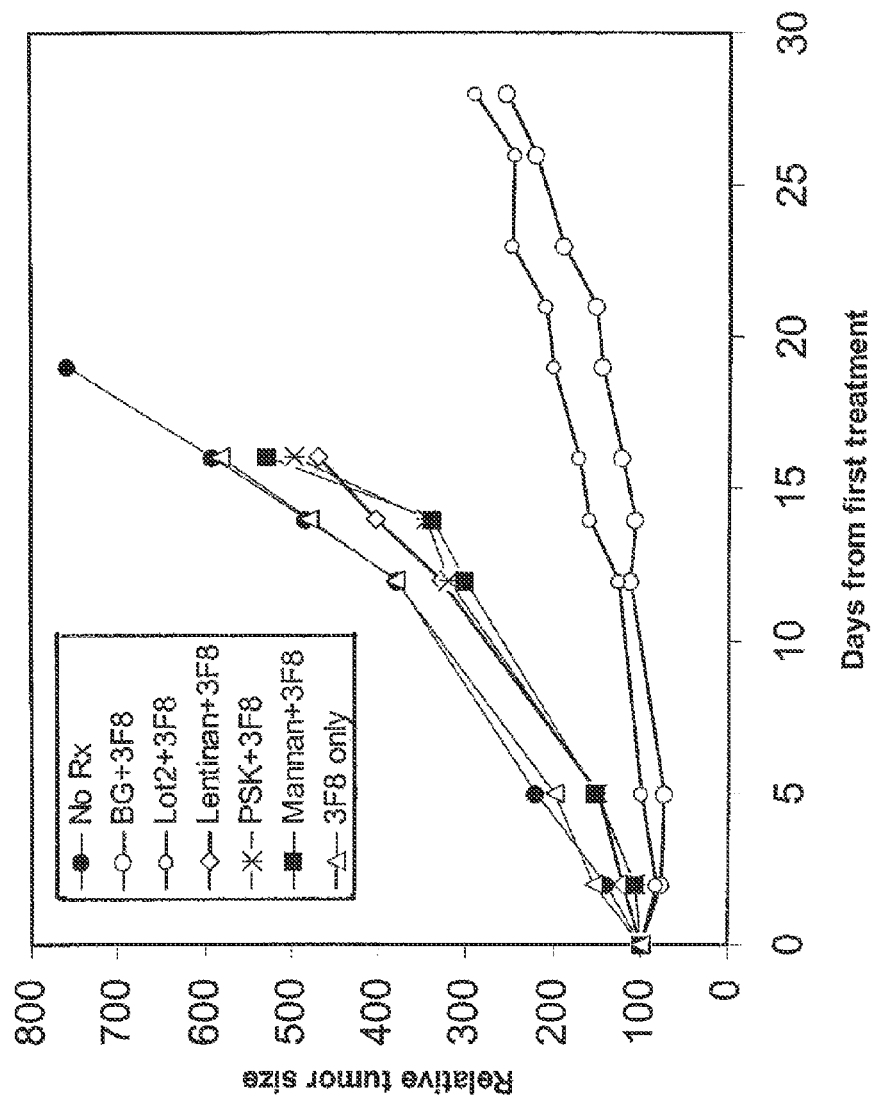

FIG. 7. More comparison of various β-glucans β-glucans (400 ug po qd) from different barley lots [large open circle, small open circle], lentinan [open diamond], PSK [cross] were compared to mannan [solid square], 3F8 only [open triangle] or no treatment [solid circle]. Only BG from barley showed syngergistic anti-tumor effect with antibody 3F8 against LAN-1 xenografts.

Figure 8:
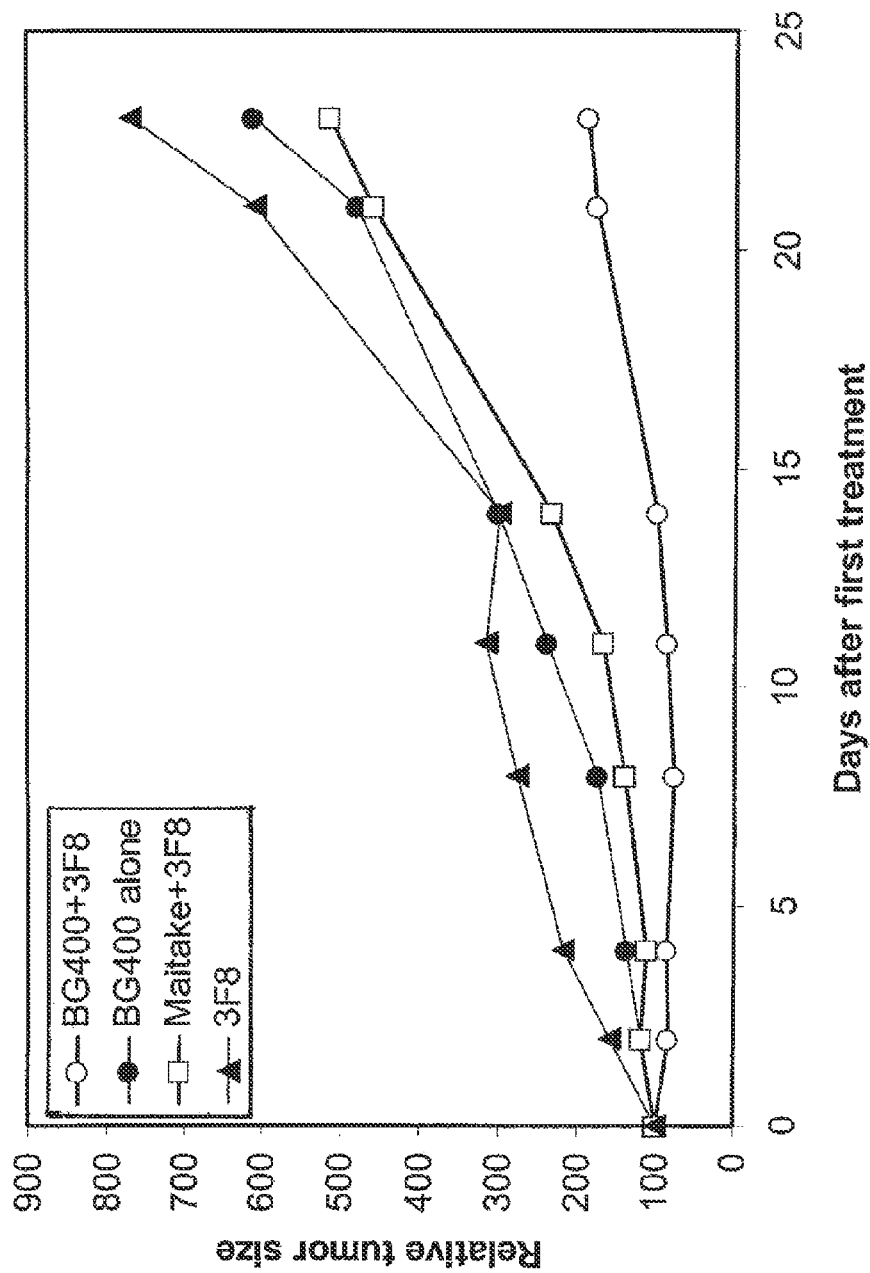

FIG. 8. D-fraction Maitake Mushroom β-glucan [open square] had no anti-tumor effect when compared to barley β-glucan alone [solid circle], 3F8 alone [open triangle], in contrast to barley β-glucan plus 3F8 [open circle] which was highly effective.

Figure 9:
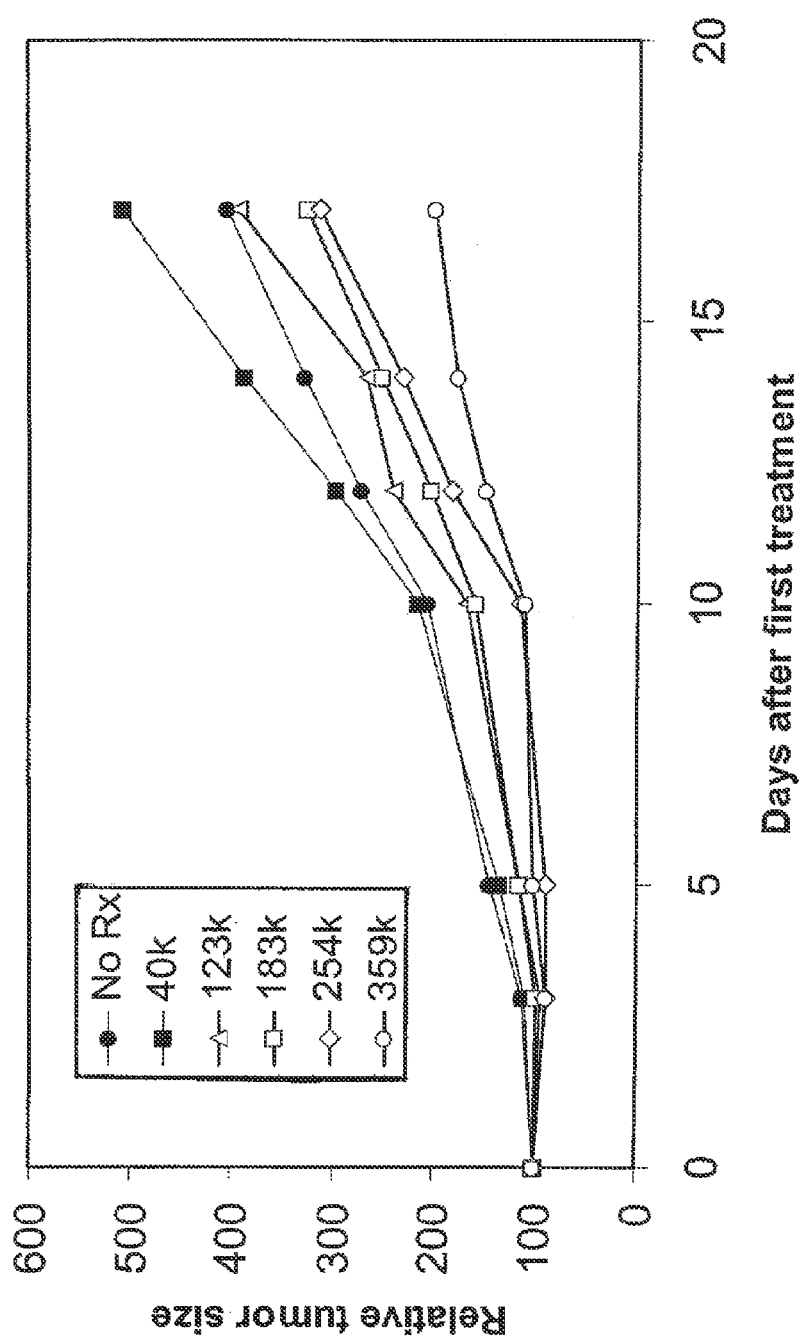

FIG. 9. Barley β-glucan of large molecular weight is more effective β-glucan of 40K [solid square], 123K [open triangle], 183K [open square], 254K [open diamond], and 359K [open circle] were tested at 40 ug po daily dose in combination with 3F8 against LAN-1 subcutaneous xenografts. The larger the size of the β-glucan, the more effective the synergistic effect.

Figure 10:
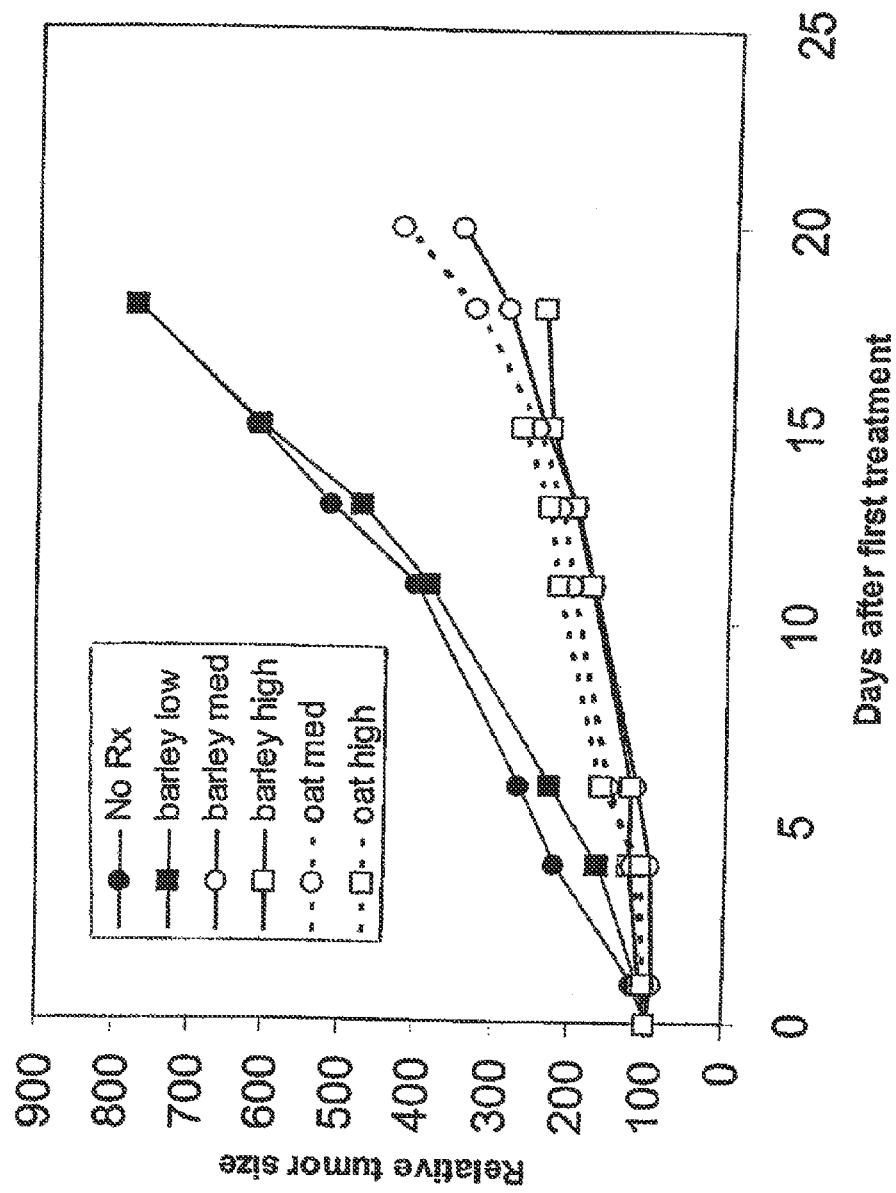

FIG. 10. β-glucans of low molecular weight and low viscosity was ineffective β-glucans of various viscosities [40 ug po qd] derived from barley and oats were tested in combination with 3F8 against LAN-1 subcutaneous xenografts. Barley medium viscosity [large open circle], barley high viscosity [open square], oat medium viscosity [small open circle, dotted line], and oat high viscosity [open square, dotted line] were all effective in shrinking and suppressing tumor growth, in contrast to low viscosity barley β-glucan [solid square].

Figure 11:
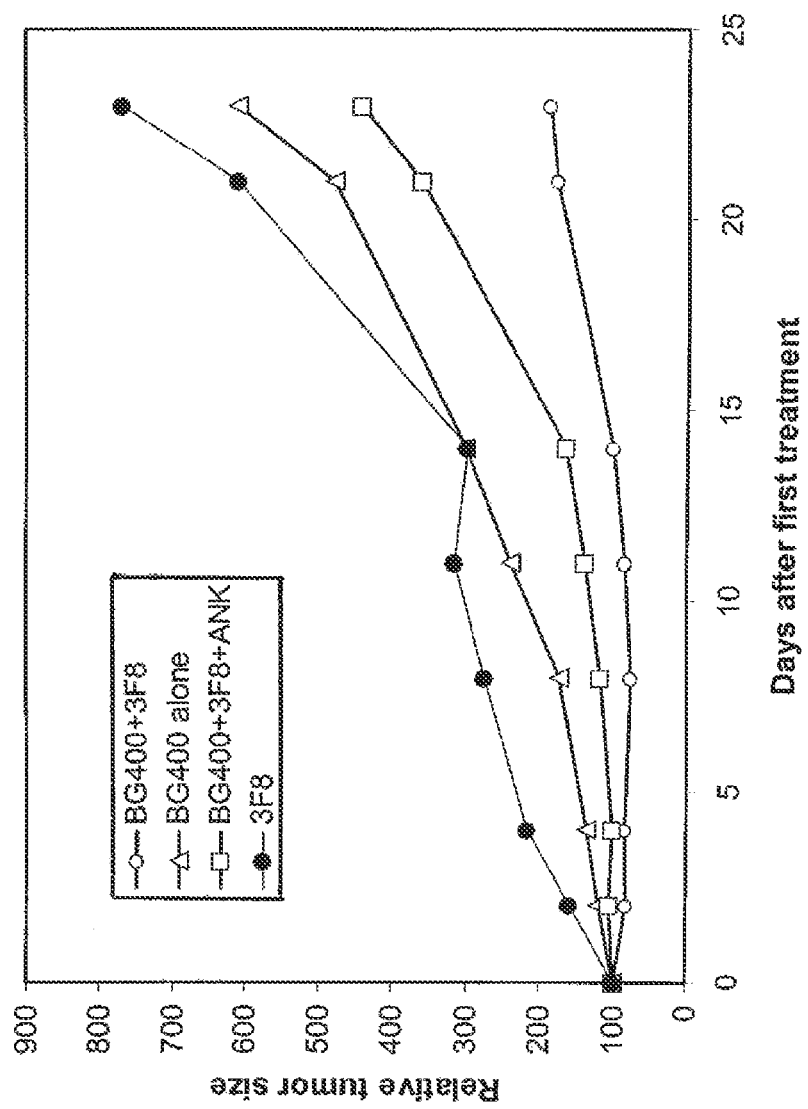

FIG. 11. Removal of NK cells by anti-Asialo GM1 antiserum in LAN-1 xenograft decreased but did not eliminate the anti-tumor effect of barley β-glucan plus 3F8.

Figure 12:
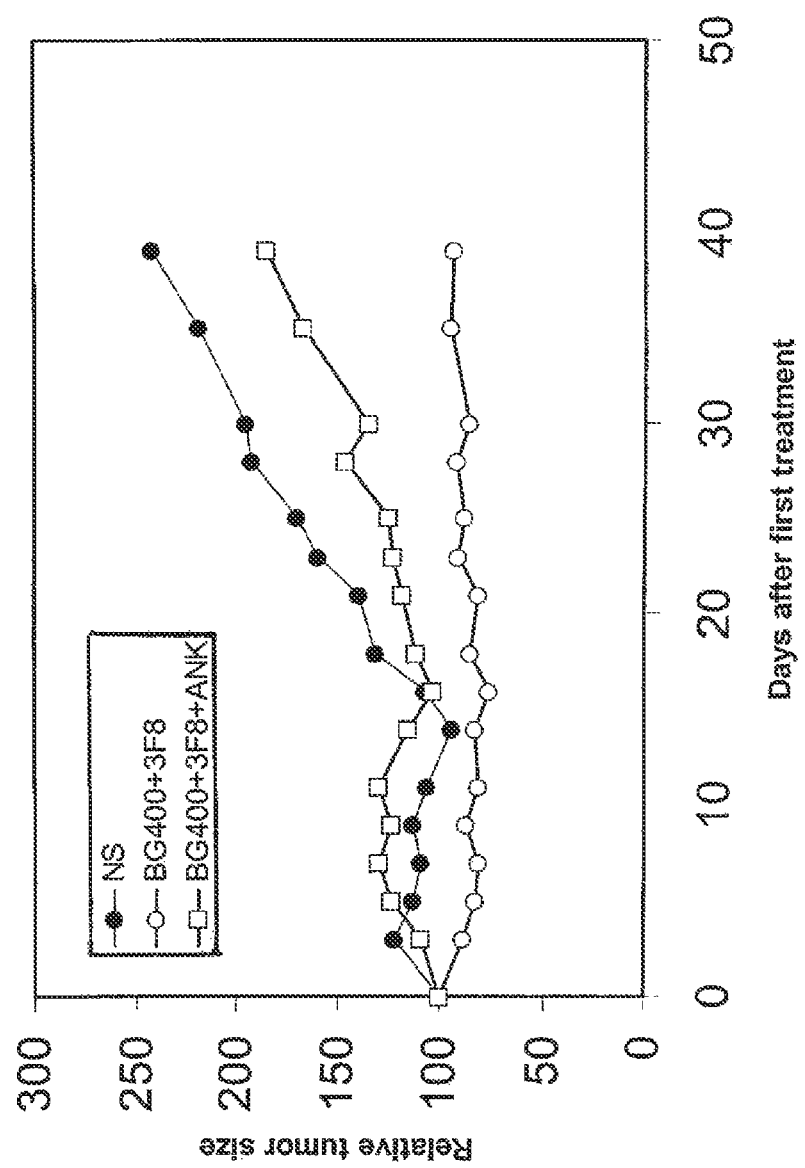

FIG. 12. Removal of NK cells by anti-Asialo GM1 antiserum in NMB-7 xenograft again decreased but did not eliminate the anti-tumor effect of barley β-glucan plus 3F8.

Figure 13:
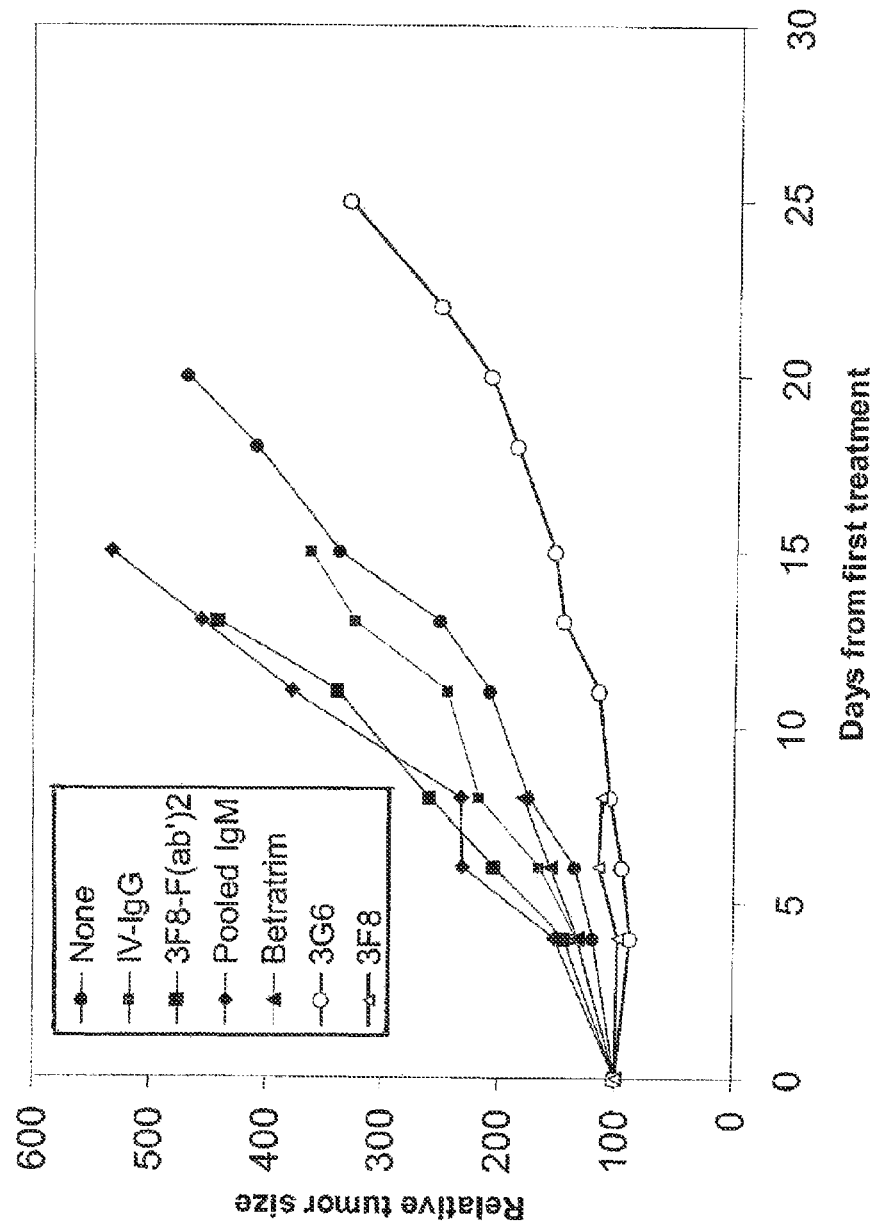

FIG. 13. 3F8-F(ab')2 fragment [solid square], nonspecific human IgG [small solid square] or IgM [solid diamond] have no anti-tumor effect while 3G6 (IgM anti-GD2, open circle) was almost as effective as 3F8 (IgG3 anti-GD2, open triangle).

Figure 14:
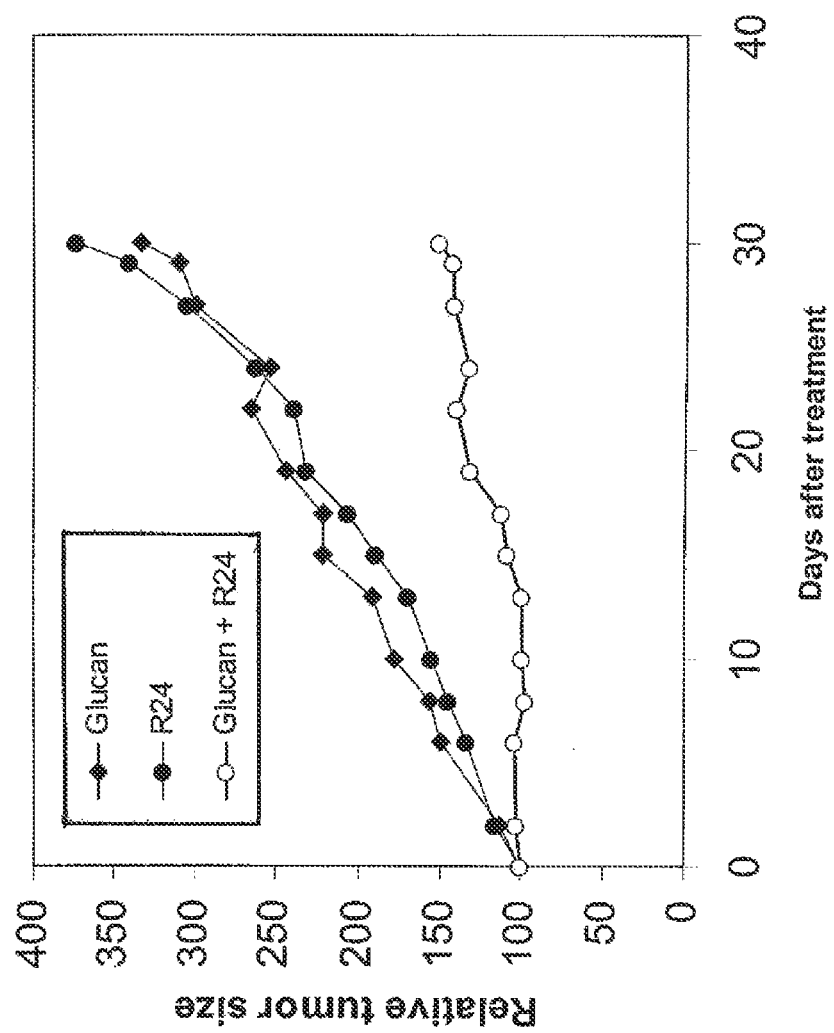

FIG. 14. Barley β-glucan synergizes with R24 anti-GD3 antibody in SKMe128 melanoma xenografts in nude mice In contrast to β-glucan control [solid diamond], and R24 control [solid circle], the combination of R24 and β-glucan [open circle] significantly suppressed tumor growth.

Figure 15:
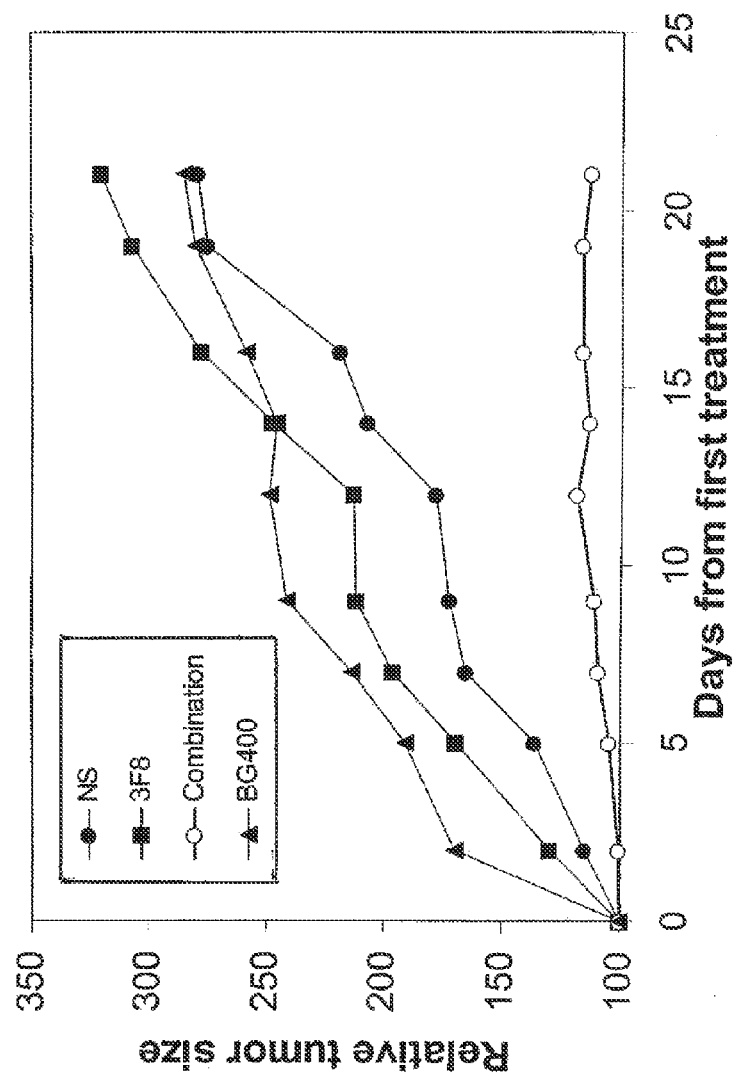

FIG. 15. Barley β-glucan synergizes with 3F8 anti-GD2 antibody against B16D14 murine melanoma in C57Bl/6 mice In contrast to saline control [solid circle], β-glucan control [solid triangle], and 3F8 control [solid square], the combination of 3F8 and β-glucan [open circle] significantly suppressed tumor growth.

Figure 16:
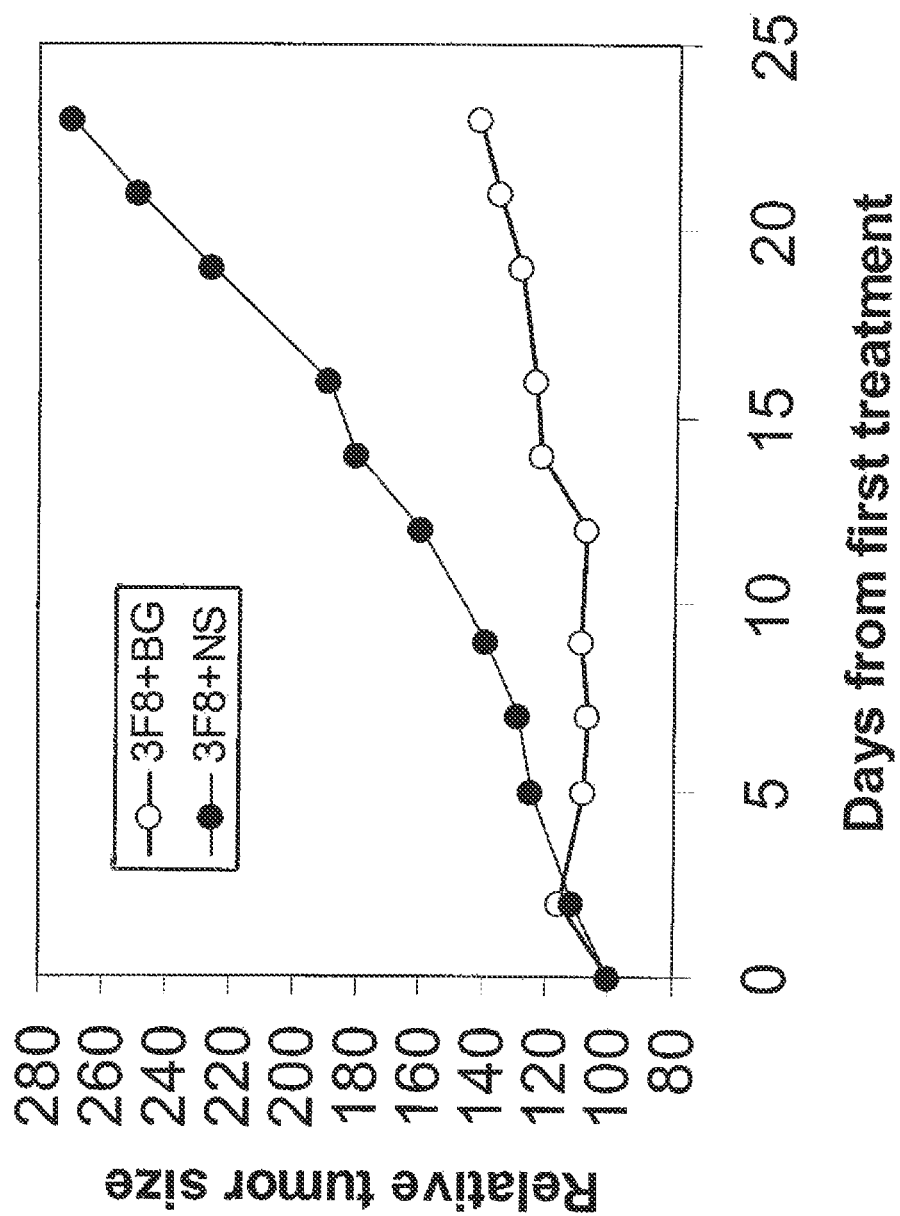

FIG. 16. Barley β-glucan synergizes with 3F8 anti-GD2 antibody against B16D14-KbKd murine melanoma in C57Bl/6 mice In contrast to 3F8 control [solid circle], the combination of 3F8 and β-glucan [open circle] significantly suppressed tumor growth.

Figure 17:
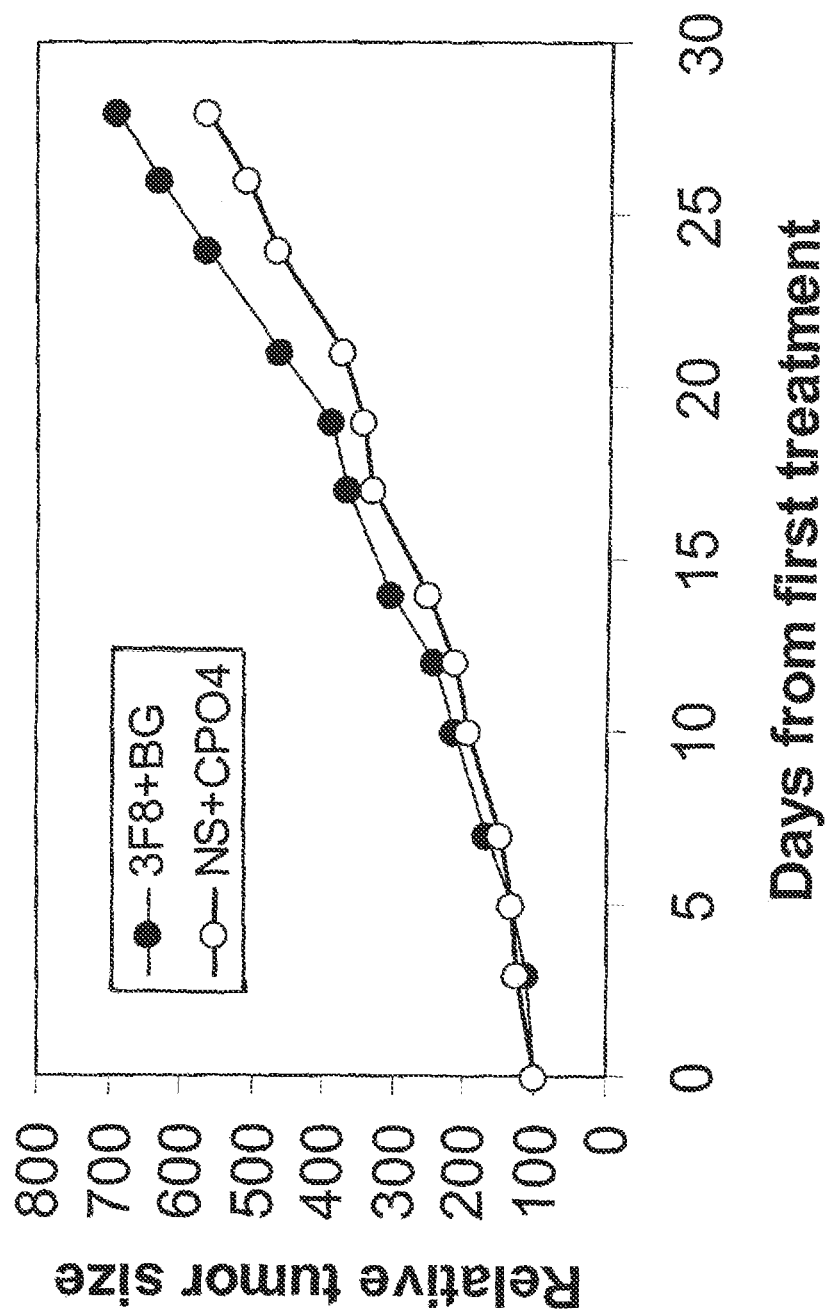

FIG. 17. Barley β-glucan plus 3F8 did not affect GD2-negative B16 melanoma in C57Bl/6 mice The combination of 3F8 and β-glucan [solid circle] did not significantly suppress tumor growth when compared to controls [open circle].

Figure 18:
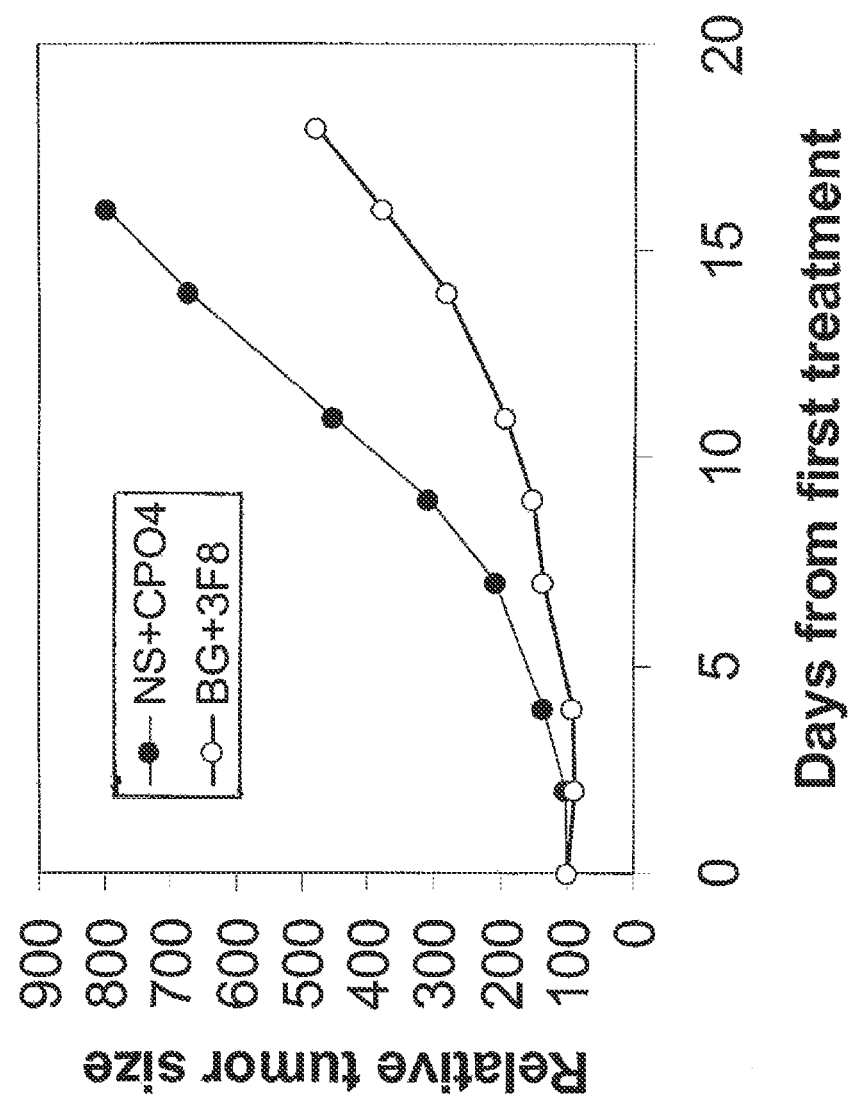

FIG. 18. Barley β-glucan synergizes with 3F8 anti-GD2 antibody against E14 murine lymphoma in C57Bl/6 mice In contrast to control [solid circle], the combination of 3F8 and β-glucan [open circle] significantly suppressed tumor growth.

Figure 19:
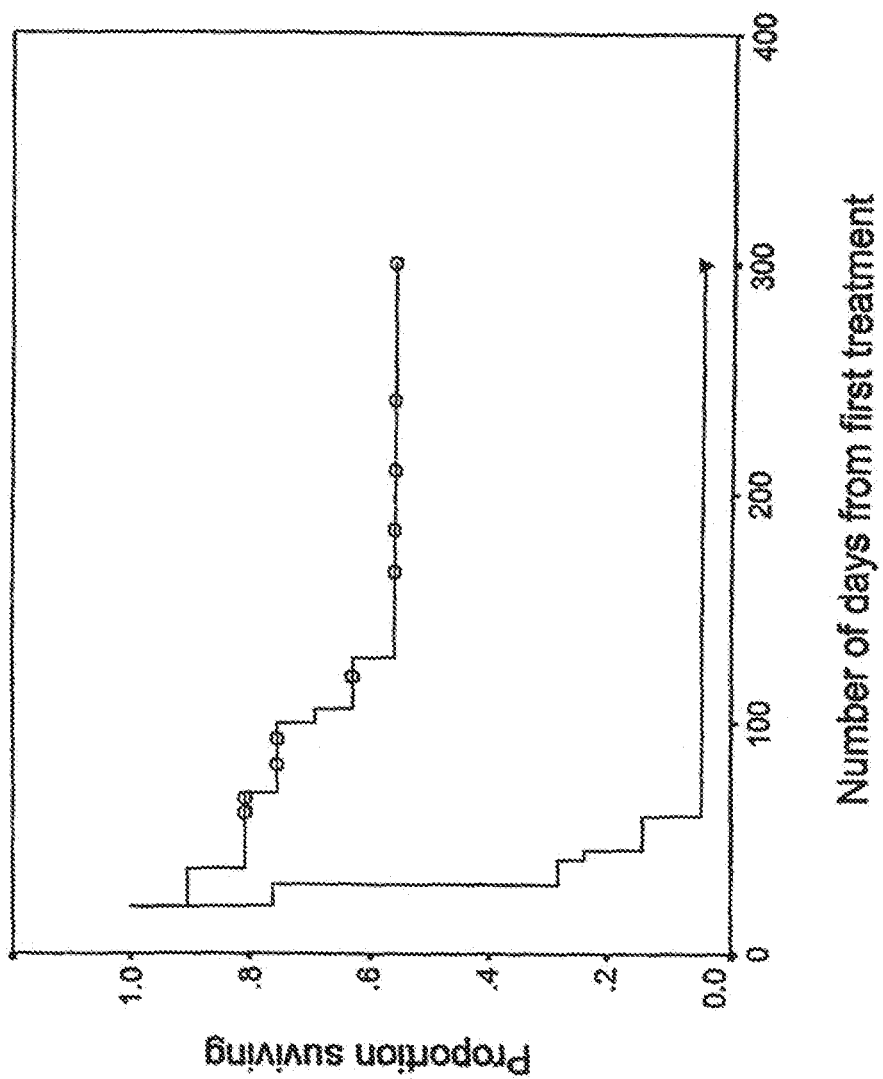

FIG. 19. BARLEY Glucan synergizes with 3F8 in prolonging survival from NMB7 neuroblastoma. Nude mice (n=21) with established neuroblastoma NMB7 xenografts treated with 3F8 and barley β-glucan (open circles) had significantly longer median survival>300 days compared to 30 days in the control mice (solid triangle) treated with saline alone, 3F8 alone, or β-glucan alone ($p<0.001$). Long-term survival was 56% in the treatment group and 5% in the control group.

Figure 20:
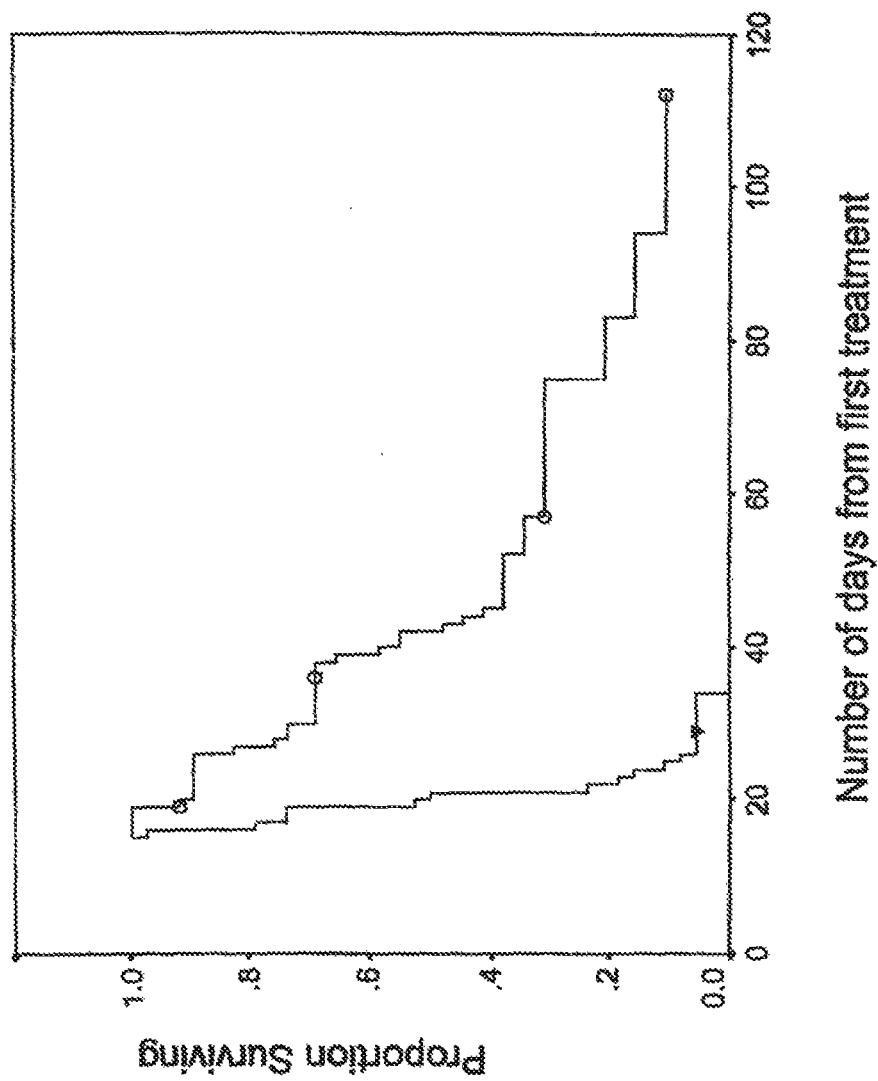

FIG. 20. BARLEY glucan synergizes with 3F8 in prolonging survival from LAN-1 neuroblastoma. In nude mice bearing established LAN1 xenografts median survival increased from 20 days in the control group (n=38, solid triangles) to 42 days in the 3F8 plus glucan group (n=48, open circles, $p<0.001$).

Second Series of Experiments

Figure 21A:
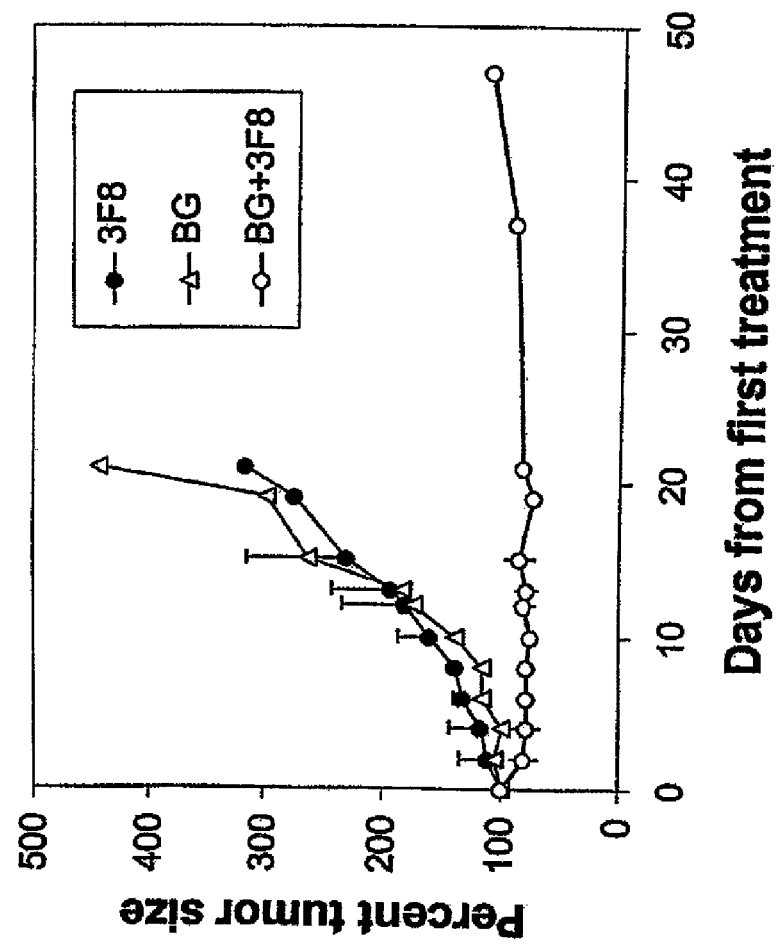
Figure 21B:
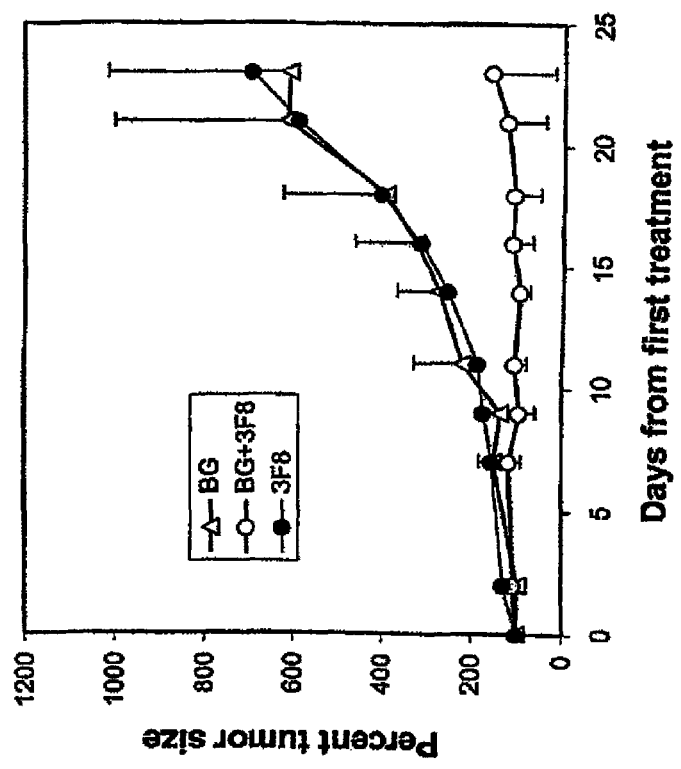
Figure 21C:
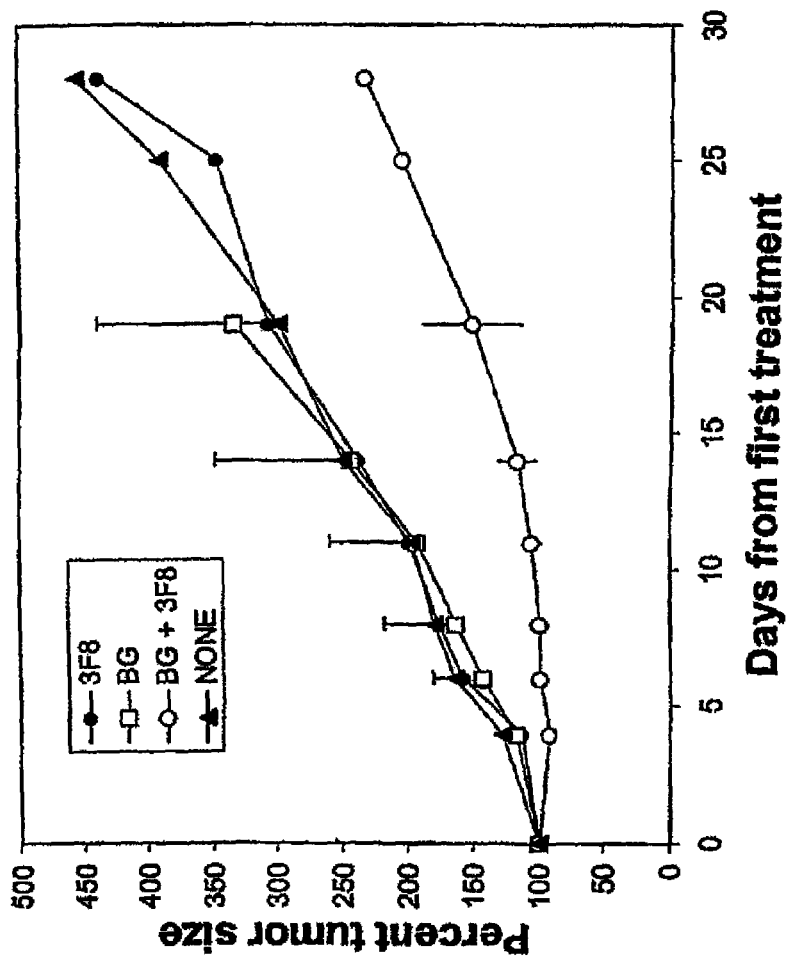

FIG. 21. Synergistic effect of MoAb and β-glucan in neuroblastoma xenografts. Two million neuroblastoma cells (21A: LAN-1, 21B: NMB7, 21C:SK-N-ER) were xenografted subcutaneously in athymic Balb/c mice. Treatment started in groups of 5 mice each, 2 weeks after tumor implantation when visible tumors reached 0.7-0.8 cm diameter. 3F8 group (solid circles) was treated with 200 ug of intravenous 3F8 injected through the retroorbital plexus twice weekly (M and Th). 3F8+BG group (open circle) was treated with 200 ug i.v.3F8 twice weekly plus oral β-glucan (BG) 400 ug daily by gavage for a total of 21-29 days. BG group (open triangle) received 400 ug oral β-glucan alone. Tumor size was measured from the first day of treatment, and the product of the largest diameters expressed as percent of the size on day 0 of treatment. Vertical bars represent standard errors, which were similar for the glucan and the 3F8 alone groups. While BG alone and 3F8 alone showed no anti-tumor effect, the BG+3F8 group showed highly significant tumor shrinkage and suppression ($p<0.01$).

Figure 22:
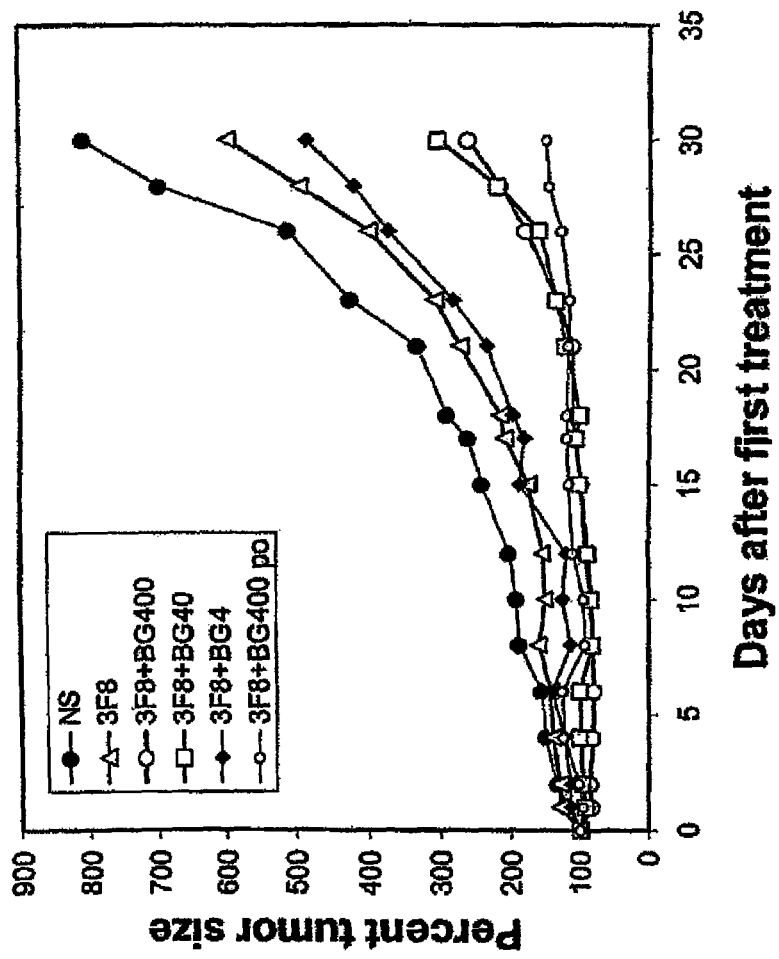

FIG. 22. Dose response of intraperitoneal (ip) β-glucan. Two million NMB7 xenografted athymic nude mice were treated at the time of visible tumors with 3F8 alone, normal saline control, or 3F8 plus increasing doses of intraperitoneal BG (4 ug [solid diamond], 40 ug [open square], 400 ug [large open circle]) or 400 ug of po BG [small open circle]. Highly significant tumor shrinkage and suppression was shown in the combination groups except at 4 ug of BG dose. Oral BG appeared to be more effective than ip BG.

Figure 23:
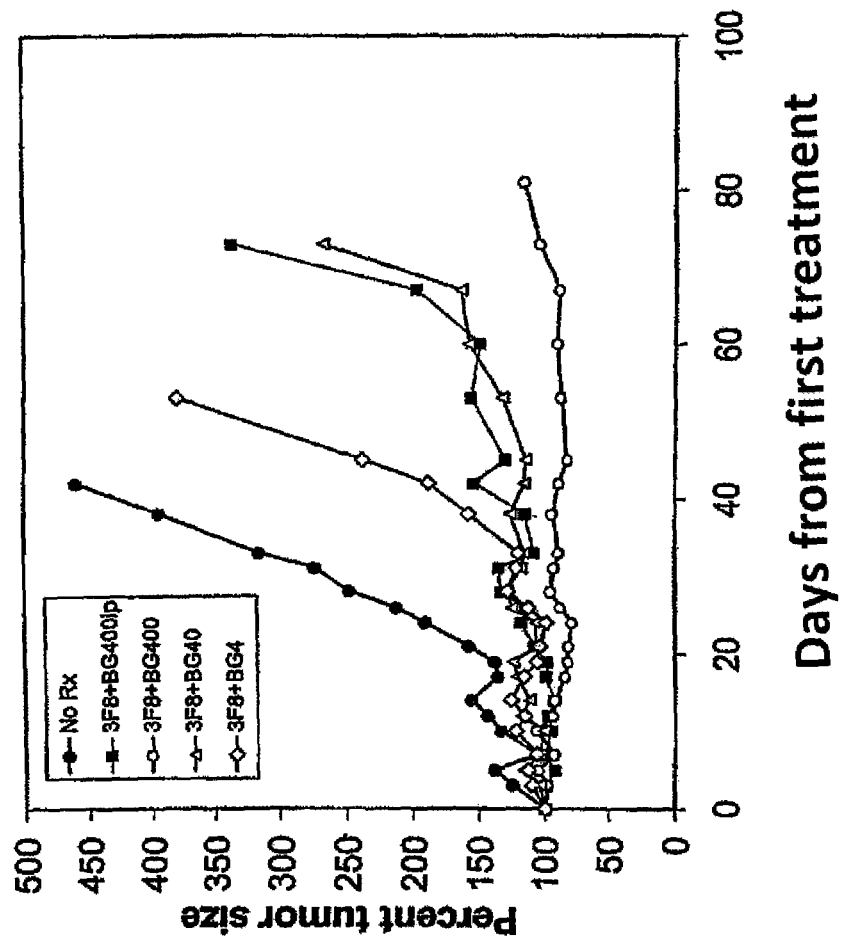

FIG. 23. Dose response of oral β-glucan. NMB7 xenografted in nude mice were treated as in FIG. 23 except that dose response of oral β-glucan (4 ug [open diamond], 40 ug [open triangle], 400 ug [open circle]) was compared to 400 ug of ip BG [solid square]. Control group received saline [solid circle]. 400 ug po was again highly significant in eradicating or suppressing tumor growth. 400 ip appeared to be as effective as 40 ug po. 4 ug was the least effective.

Figure 24:
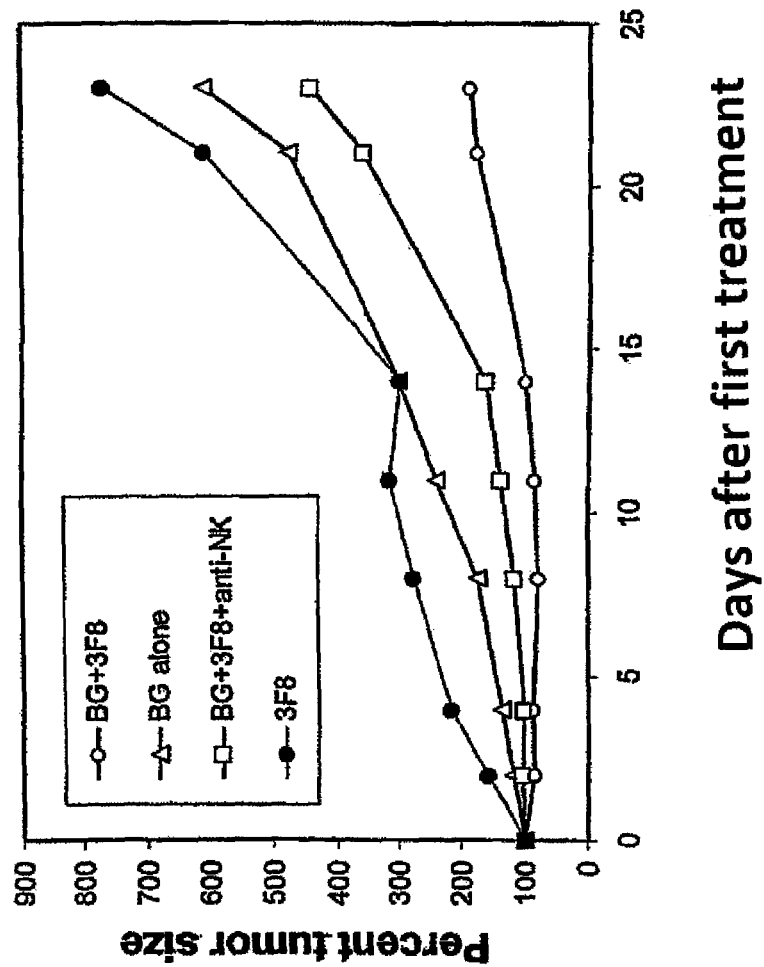

FIG. 24. Removal of NK cells by anti-Asialo GM1 antiserum on β-glucan effect in LAN-1 xenografts decreased but did not eliminate the anti-tumor effect of β-glucan plus 3F8.

Figure 25:
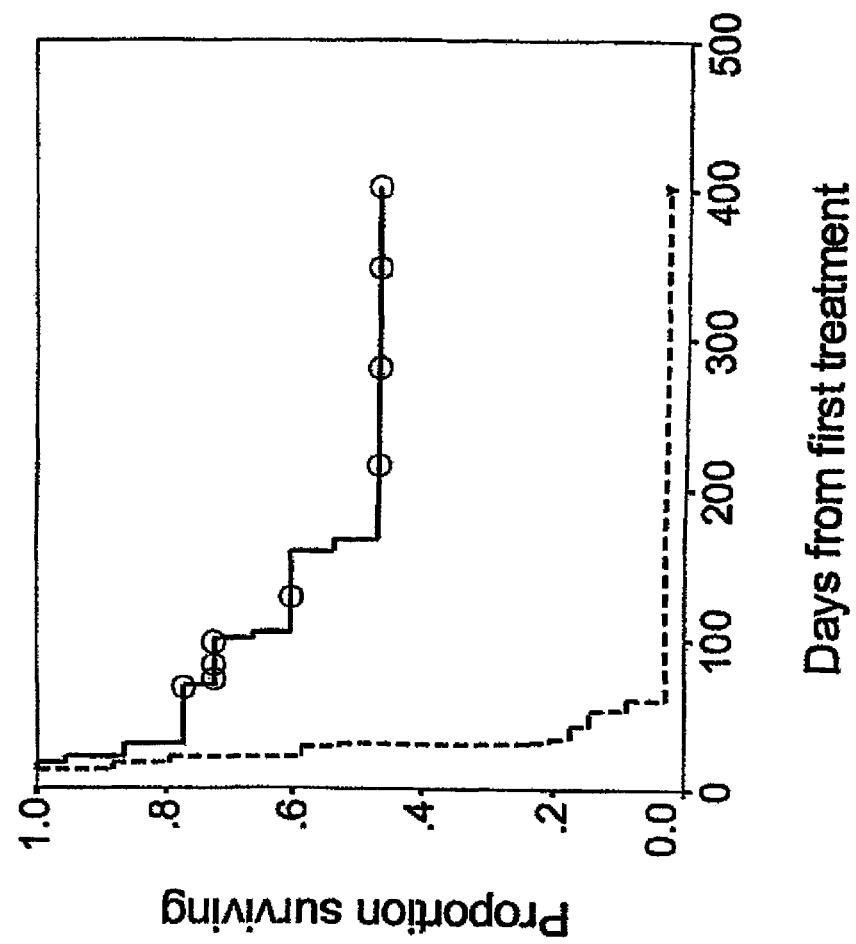

FIG. 25. Barley β-glucan synergized with 3F8 in prolonging survival from NMB7 neuroblastoma. Nude mice (n=22) with established neuroblastoma NMB7 xenografts treated with 3F8 and barley β-glucan (solid line) had significantly longer median survival (median 166 days) compared to control mice (n=34, broken line, median 30 days) treated with saline alone (n=10), 3F8 alone (n=8), or β-glucan alone (n=16) ($p<0.001$). Long-term survival was 47% in the treatment group and 3% in the control group.

Figure 26:
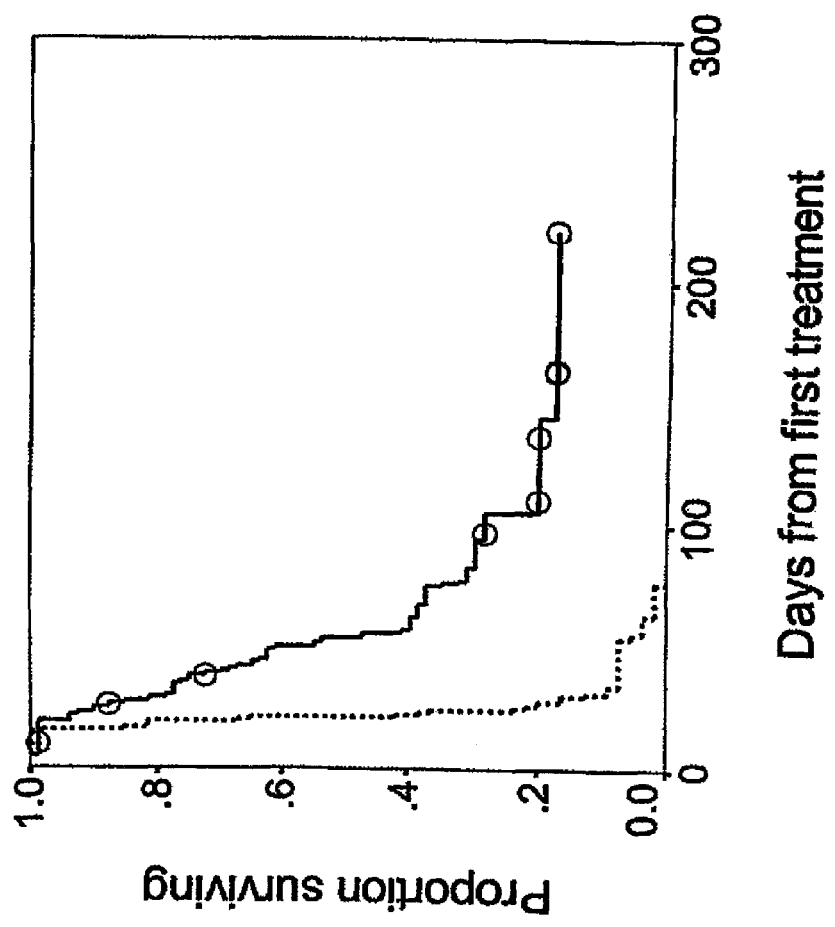

FIG. 26. Barley β-glucan synergized with 3F8 in prolonging survival from LAN-1 neuroblastoma. In nude mice bearing established LAN-1 xenografts, median survival increased from 21 days in the control group (n=55, broken line) to 54 days in the 3F8 plus glucan group (n=82, solid line, $p<0.001$).

Third Series of Experiments

Figure 27:
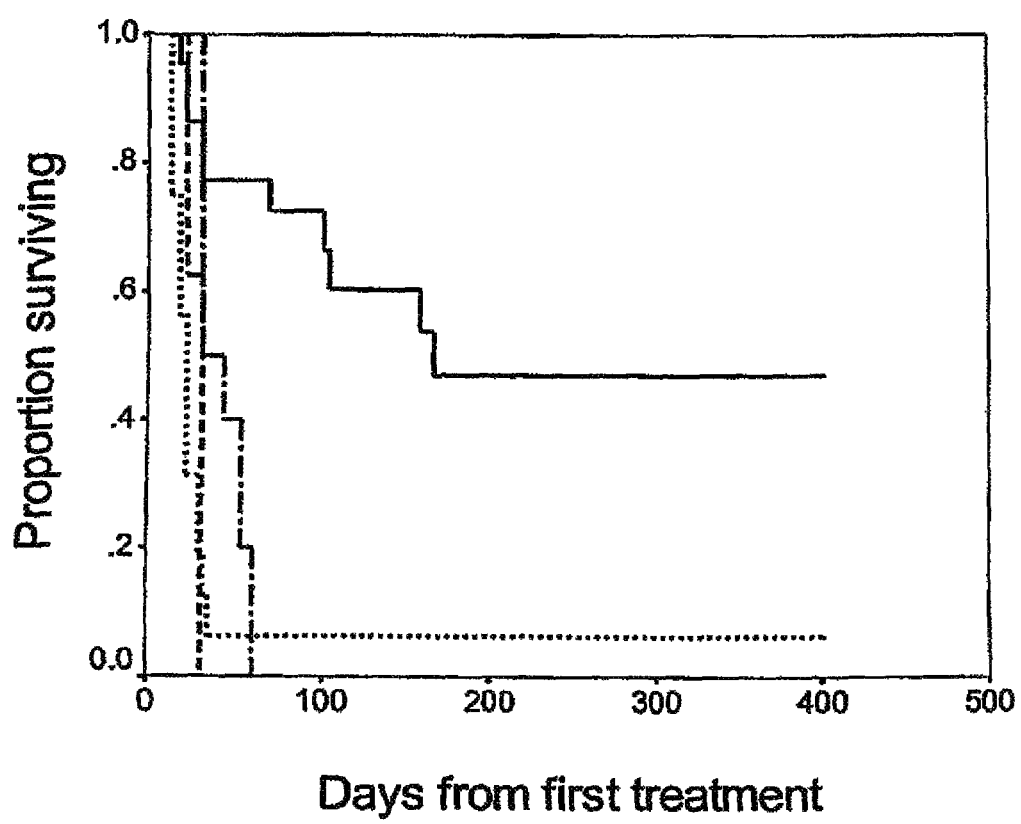

FIG. 27. Oral β-glucan syngergizes with 3F8 in prolonging survival from neuroblastoma. Nude mice (n=22, solid line) with established NMB7 xenografts (0.7-0.8 cm diameter tumor at the beginning of treatment) were treated with 3F8 (200 ug twice a week iv) and 400 ug of β-glucan po daily for a total of 3 weeks. Control mice received either saline alone (n=10, broken line), 3F8 alone (n=8, dashed line), or β-glucan (n=16, dotted line) alone. Median survival was 30 days in control groups and 166 days in the treatment (3F8 plus β-glucan, n=22) group ($p<0.001$). Ten (45%) in the combination group survived long term with a median follow-up of 248 days. Only one mouse in any of the control groups (<5%) remained alive during the experiment.

Figure 28:
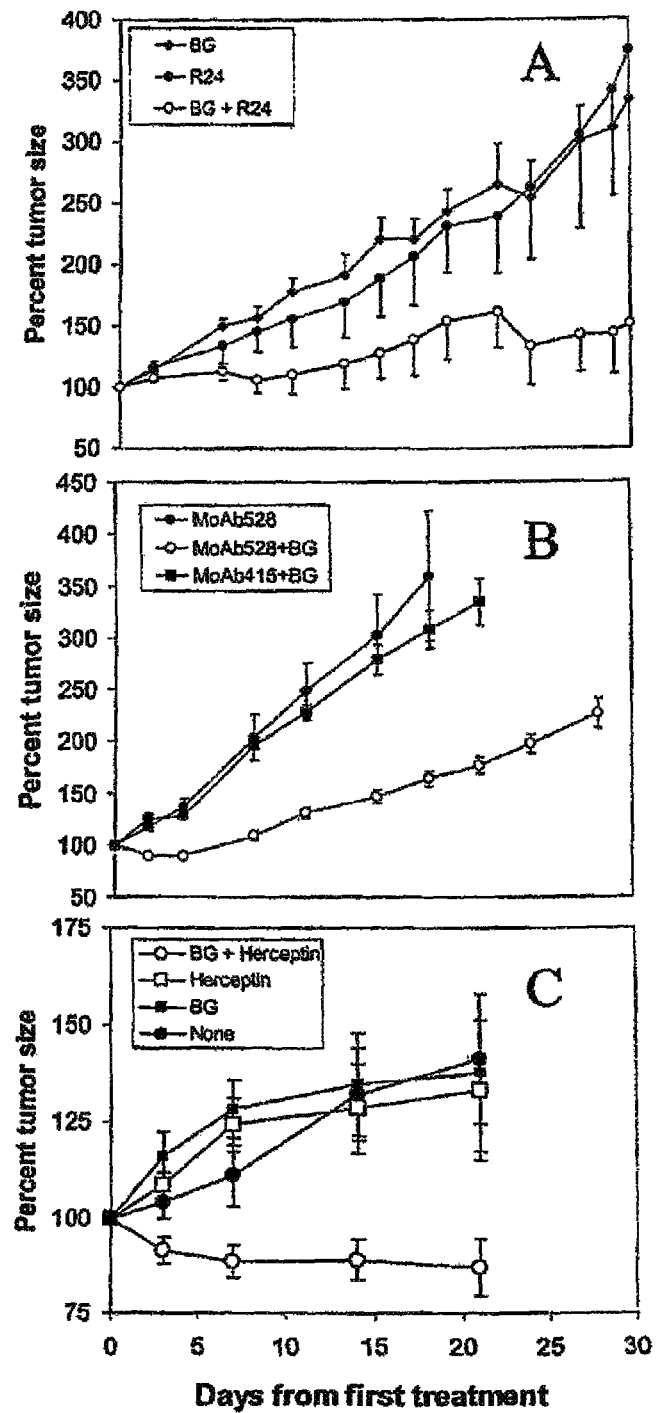

FIG. 28. Syngery of Oral barley β-glucan with (A) R24 (anti-GD3) antibody against SKMe128 melanoma xenografts in nude mice. In contrast to β-glucan control [solid diamonds], and R24 control [solid circles], the combination of R24 and β-glucan [open circles] significantly suppressed tumor growth (tumor growth rate reduced for combination treatment by 1.2%, 95% CI −0.1%, 2.5%, p=0.06) (B) 528 (anti-EGF-R) MoAb against epidermoid carcinoma A431 xenografts in nude mice. In contrast to β-glucan+455 (IgG1 noncomplement fixing) control [solid sqaures], and 528 MoAb alone [solid circles], the combination of 528 MoAb and β-glucan [open circles] significantly suppressed tumor growth (tumor growth rate reduced for combination treatment by 1.4%, 95% CI −0.7%, 3.5%, p=0.17). (C) Herceptin (anti-HER2) antibody against human breast carcinoma BT474 xenografts in nude mice. In contrast to control [n=4, solid circles], Herceptin [n=9, open squares], or β-glucan control [n=7, solid squares], the combination of Herceptin and β-glucan [n=12, open circles] significantly suppressed tumor growth (tumor growth rate reduced for combination treatment by 1.9%, 95% CI 0.7%, 3%, p=0.002).

Fourth Series of Experiments

Figure 29:
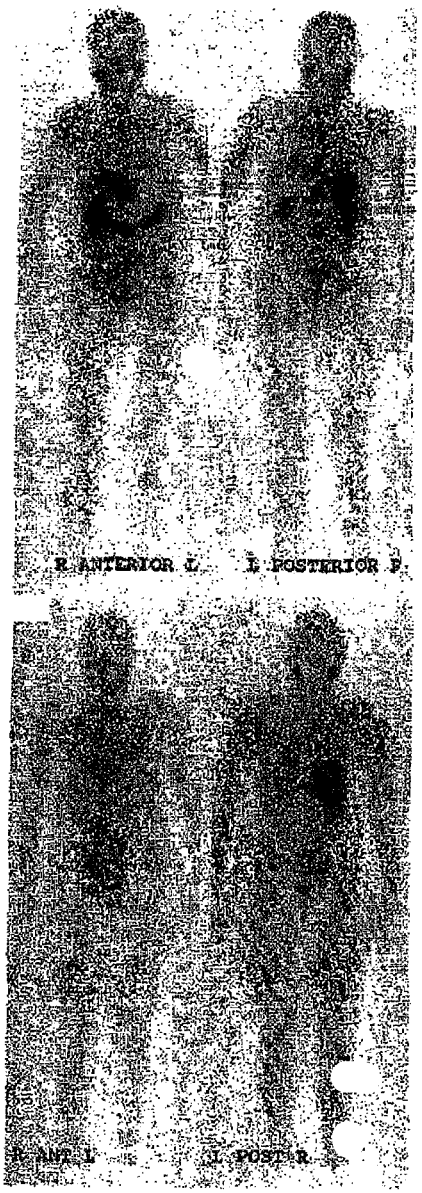

FIG. 29A. Baseline MIBG scan of patient 5. Extensive osseous metastasis can be seen in the femora, fibulae, pelvis, rib, left scapula, right clavicle, humeri, skull and spine. Heart, liver, stomach and colon uptakes are physiologic.

FIG. 29B. MIBG Scan of same patient 2 months later, following a single cycle of therapy. Areas of metastases have significantly improved.

Fifth Series of the Experiment

Figure 30A:
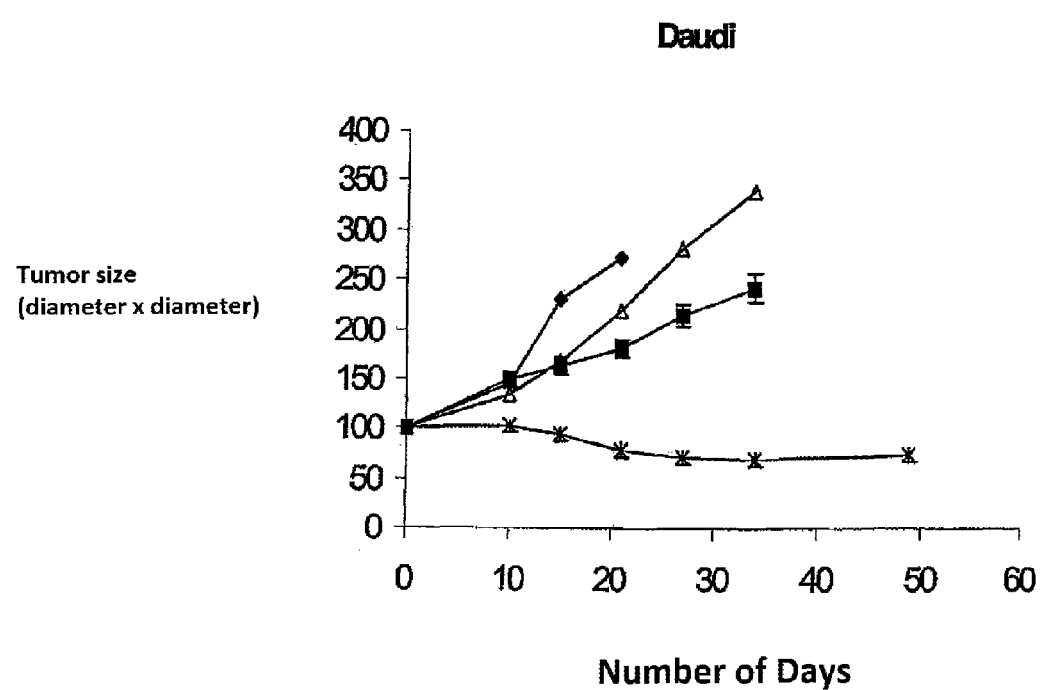
Figure 30B:
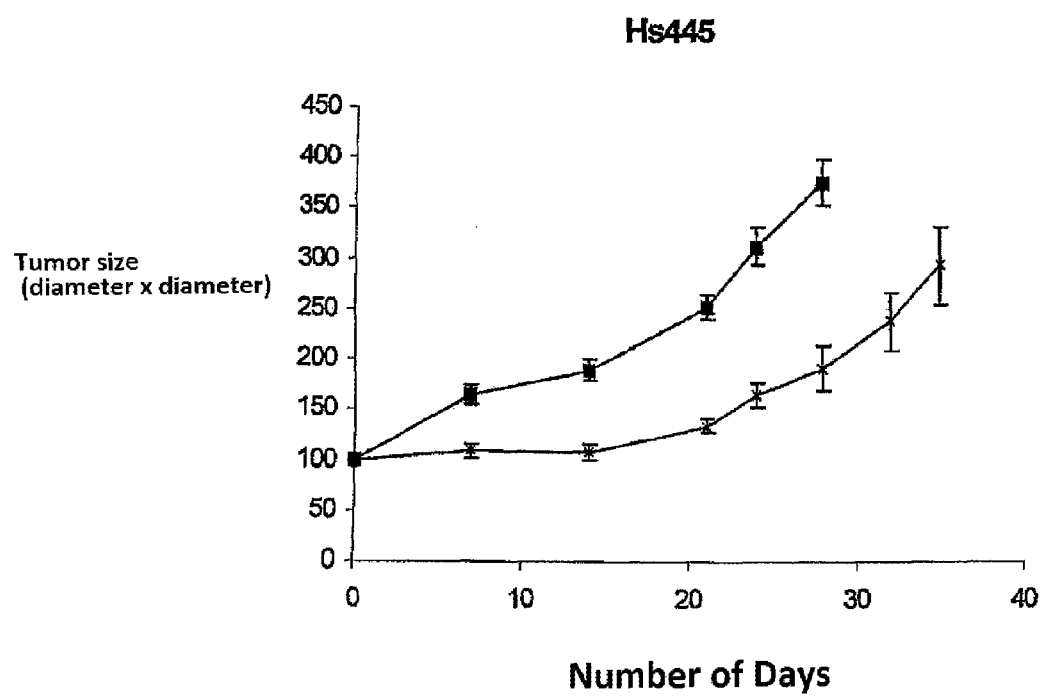
Figure 30C:
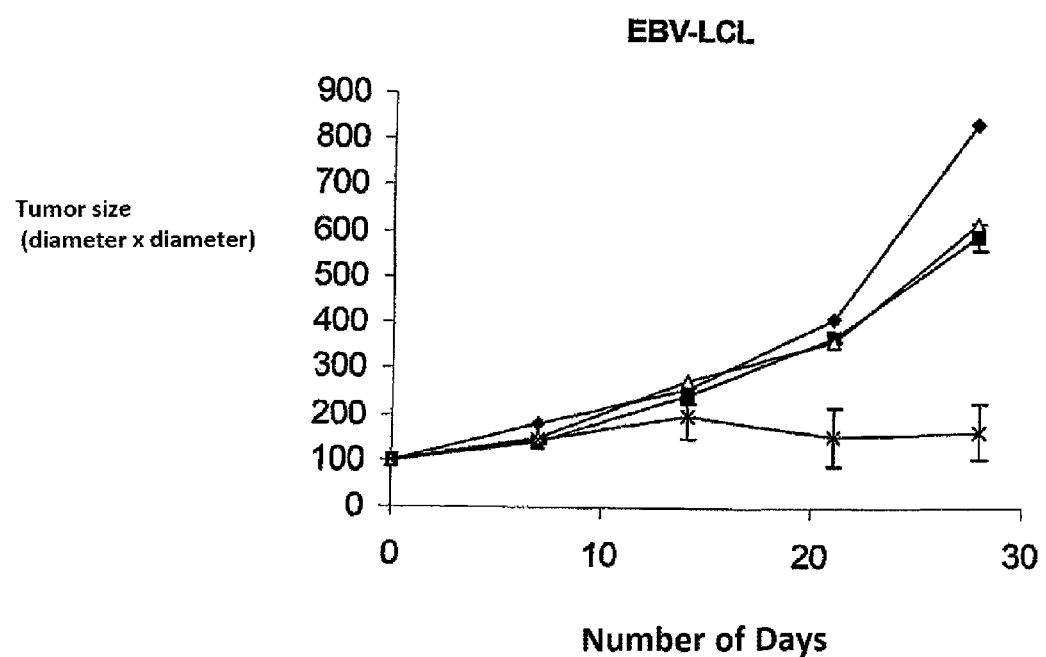

FIG. 30. Subcutaneous xenograft growth in SCID mice. SCID mice with established subcutaneous Daudi (n=9) (FIG. 30A), Hs445 (n=5)(FIG. 30B), EBV-derived LCL (n=9) (FIG. 30C) and RPMI 6666 (n=10; data not shown) xenografts were treated either with 200 ug intravenous rituximab twice weekly for 8 doses (■),400 ug (1→3), (1→4)-D-β-glucan administered orally via intragastric gavage daily for 29 days (Δ) or a combination of rituximab and (1→3), (1→4)-D-β-glucan (×), or left untreated (♦). Percentage tumor growth is plotted on y-axis and days after treatment was commenced on x-axis. Error bars represent SEM and have been shown only for rituximab alone and combination groups. For all xenografts, only combination treatment was associated with reduction in tumor growth. The reduction in tumor growth per day in the group receiving β-glucan in addition to rituximab compared to rituximab alone was 2.0% (95% CI 1.3-2.7%; p<0.0005) for Daudi, 0.8% for EBV-derived LCL (95% CI 0.4-1.2%; p<=001), 2.2% for Hs445 (95% C.I. 1.2%-3.2%; p=0.0009), and 1.8% for RPMI6666 (95% CI 1.0-2.7%; p<0.0002; data not shown) xenografts.

Figure 31A:
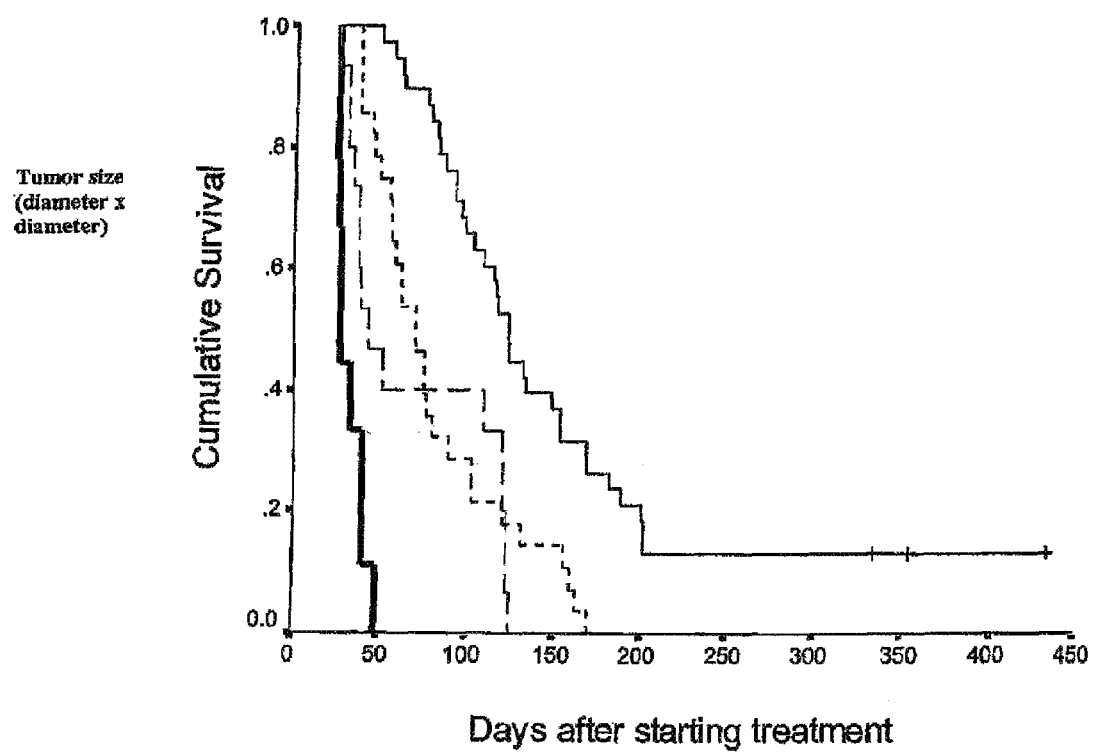
Figure 31B:
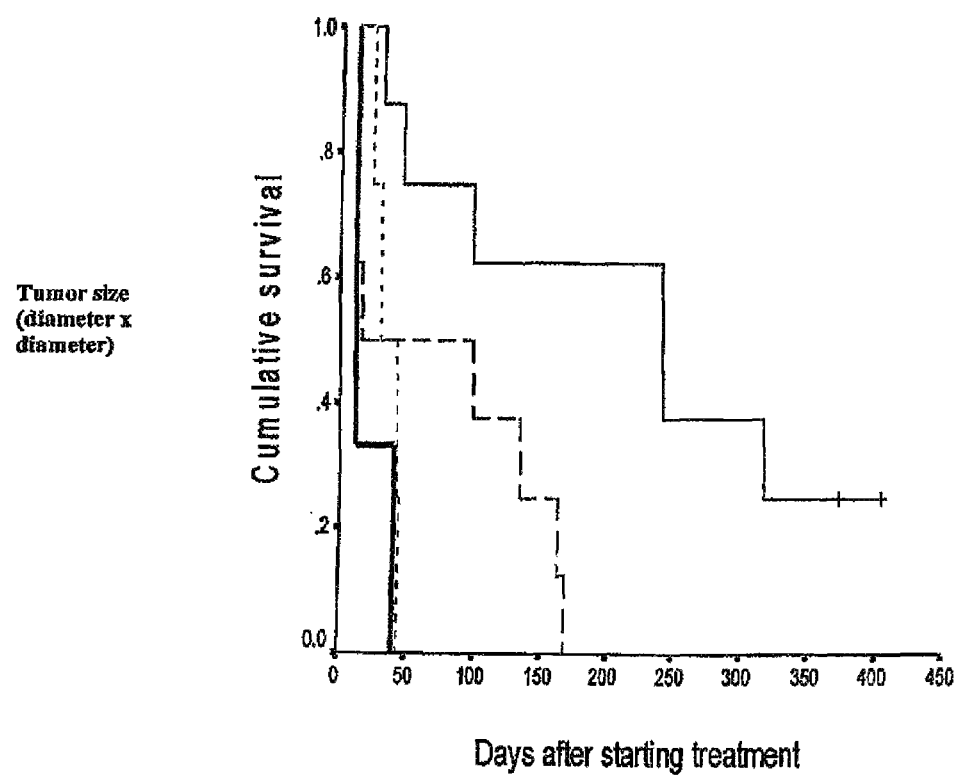

FIG. 31. Survival in SCID mice with disseminated lymphoma xenografts. $5 \times 10^6$ Daudi (FIG. 31A) or Hs445 (FIG. 31B) cells in 100 µl normal saline were injected intravenously (IV) into SCID mice. Mice were treated either with 200 ug intravenous rituximab twice weekly for 8 doses ( - - - ), 400 ug (1→3), (1→4)-D-β-glucan administered orally via intragastric gavage daily for 29 days ( . . . . ) or a combination of rituximab and (1→3), (1→4)-D-β-glucan (-), or left untreated (-) commencing 10 days after tumor implantation. Tumors grew systemically and mice became paralyzed when tumor cells infiltrated the spinal canal, resulting in hind-leg paralysis. Mice were sacrificed at onset of paralysis or when animals lost 10% of their body weight. Kaplan-Maier survival curves for the various groups are shown in FIGS. 31A (Daudi) and 31B (Hs445). Mice treated with a combination of (1→3), (1→4)-D-β-glucan and rituximab had a significantly increased survival when compared to all other treatment groups (p<0.0005 for Daudi and p=0.001 for Hs445) or when compared to rituximab alone (p<0.0005 for Daudi and p=0.01 for Hs445). Median survival for mice with no treatment, rituximab alone, BG, and rituximab+BG groups was 27, 71, 43 and 124 days respectively for Daudi xenografts, and 12, 16, 31 and 243 days respectively for Hs445 xenografts.

DETAILED DESCRIPTION OF THE INVENTION

This invention provides a composition comprising an effective amount of glucan capable of enhancing efficacy of antibodies.

In an embodiment, the antibody is a monoclonal antibody. In a further embodiment, the antibody is an antibody against cancer. In another embodiment, the antibody is a tumor-binding antibody. In a further embodiment, the antibody is capable of activating complement. In a still further embodiment, the antibody is further capable of activating the antibody dependent cell-mediated cytotoxicity.

In an embodiment, the antibody is directed at the epidermal growth factor receptor. In a further embodiment, the antibody is 528 or C225.

In another embodiment, the antibody is directed to a ganglioside. In a further embodiment, the ganglioside is GD3. In a still further embodiment, the antibody is R24.

In a separate embodiment, the ganglioside is GD2. In a further embodiment, the antibody is 3F8.

In an embodiment, the antigen recognized by the antibody is CD20. In a further embodiment, the antibody is Rituximab.

In another embodiment, the antigen is CD25. In a further embodiment, the antibody is Dacluzimab.

In a separate embodiment, the antigen is Her2/neu. In a further embodiment, the antibody is Herceptin.

In another embodiment, the antigen is CD22. In a further embodiment, the antibody is Epratuzumab.

The cancer is recognized by antibodies, and it includes but is not limited to neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma,[40] prostate cancer,[40,41] renal cell carcinoma,[40] transitional cell carcinoma,[40] breast cancer,[42,43] ovarian cancer,[40] lung cancer, colon cancer,[40] liver cancer, stomach cancer, and other gastrointestinal cancers.

This invention further provides the above compositions and a pharmaceutically acceptable carrier, thereby forming pharmaceutical compositions.

This invention also provides a pharmaceutical composition comprising a combination as described above and a pharmaceutically acceptable carrier. For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

This invention also provides a method for treating a subject with cancer comprising administrating the above-described composition to the subject.

This invention provides a composition comprising an effective amount of glucan capable of enhancing efficacy of vaccines. In an embodiment, the vaccine is against cancer.

This invention also provides the above compositions and a pharmaceutically acceptable carrier, thereby forming a pharmaceutical composition.

This invention also provides a method of treating a subject comprising administrating the above pharmaceutical composition to the subject. In an embodiment, the subject is a human subject.

In an embodiment, the vaccine is against infectious agents. The infectious agents include but are not limited to bacteria, viruses, fungi, or parasites.

This invention provides a composition comprising an effective amount of glucan capable of enhancing efficacy of natural antibodies.

In an embodiment, the antibodies are against cancer.

In another embodiment, the antibodies are against infectious agents. The infectious agents include but are not limited to bacteria, viruses, fungi, or parasites.

This invention provides a composition comprising an effective amount of glucan capable of enhancing host immunity. In another embodiment, the immunity is against cancer or infectious agents.

This invention also provides a composition comprising an effective amount of glucan capable of enhancing the action of an agent in preventing tissue rejection.

In an embodiment, the agent is an antibody. In a further embodiment, the antibody modulates T-cell function. In a still further embodiment, the antibody is anti-CD25 or anti-CD3.

In a separate embodiment, the antibody modulates B-cell function. In another embodiment, the antibody is anti-CD20.

In another embodiment, the tissue is transplanted tissue or transplanted organ. In another embodiment, the tissue is the host as in graft-versus-host reactions.

This invention also provides the above compositions, wherein the glucan are 1,3-1,4 mixed linkage, without 1,6 branches.

The invention further provides the above compositions, wherein the glucan is of high molecular weight. In an embodiment, the molecular weight of the glucan ranges from 250,000 to 450,000 daltons.

This invention provides the above compositions, wherein the glucan is derived from barley, oat, wheat, or moss.

This invention provides the above compositions, wherein the glucan is stable to heat treatment. In an embodiment, the composition is stable after boiling for 3 hours.

This invention provides the above compositions, wherein the oral route is adopted when administered a subject. In an embodiment, the effective dose is about >=25 mg/kg/day, five days a week for a total of 2-4 weeks.

This invention provides a composition for oral uptake of substance comprising an appropriate amount of carbohydrates. In an embodiment, the carbohydrate is glucan.

When administered orally, glucan is taken up by macrophages and monocytes which carry these carbohydrates to the marrow and reticuloendothelial system from where they are released, in an appropriately processed form, onto myeloid cells including neutrophils, and onto lymphoid cells including natural killer (NK) cells. This processed glucan binds to CR3 on these neutrophils and NK cells, activating them in tumor cytotoxicity in the presence of tumor-specific antibodies.

Since macrophage and monocytes ingest glucan (whether soluble, gel or particle) from the gut, glucan is a potential conduit for gene therapy. Unlike proteins, DNA or plasmids are relatively heat-stable, and can be easily incorporated into warm soluble barley glucan which gels when cooled to room or body temperature. When mice are fed these DNA-glucan complexes, reporter genes can be detected in peripheral blood monocytes and macrophages within days. More importantly these reporter genes are expressed in these cells, a few days after ingestion of these DNA complexes. These findings have potential biologic implications. Glucan and similar carbohydrates may be conduits for DNA or plasmids to get into the human body. Oral glucan may be a convenient vehicle for correcting genetic defects of macrophages/monocytes, or administering genetic vaccines.

As it can easily be appreciated by an ordinary skilled artisan, other carbohydrates capable of functioning like glucan could be identified and used in a similar fashion. One easy screening for such carbohydrates can be established using glucan as the positive control.

The glucan includes but is not limited to 1,3-1,4 mixed linkage-glucan, and the glucan is of high molecular weight.

The substance which could be delivered orally includes but is not limited to peptides, proteins, RNAs, DNAs, and plasmids. Other small molecules and compounds may be used as well.

This invention further provides a pharmaceutical composition comprising an effective amount of the above composition and a pharmaceutically acceptable carrier.

This invention also provides a method for introducing substance into cells comprising contacting the above compositions with said cells. One can use reporter genes or other markers to assess the efficiency of the said introduction. Reporter genes or markers are well known in the molecular biology field. In addition, this invention provides a method for introducing substance into a subject comprising administering to the subject an effective amount of the above compositions.

This invention provides a method for treating a subject comprising administering to the subject an effective amount of the above composition. In an embodiement, the method further comprises the substance.

This invention provides a method for treating a subject with genetic disorder comprising administering to the subject an effective amount of the above-described composition and a substance capable of correcting said genetic disorder. The substance includes but is not limited to a peptide, protein, RNA, DNA, plasmid and other small molecule and compound.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Experimental Details

Materials and Methods

Cell Lines

Human neuroblastoma cell lines LA-N-1 was provided by Dr. Robert Seeger, Children's Hospital of Los Angeles, Los Angeles, Calif. and NMB7 by Dr. Shuen-Kuei Liao (McMaster University, Ontario, Canada). Neuroblastoma cell lines SKNHM, SKNHB, SKNJD, SKNLP, SKNER, SKNMM, SKNCH and SKNSH were derived from patients with metastatic disease treated at Memorial Sloan-Kettering Cancer Center (MSKCC), New York, N.Y. Other cells lines, Daudi, RMPI 6666, SKMel-28, A431, B16 were derived from American Type Culture Collection (ATCC), Rockville, Md. The cell lines B16, B16D14 were kindly provided by Dr. Kenneth Lloyd of Memorial Sloan-Kettering Cancer Center. Kb transfected (B16D14Kb) and (Kb+Kd) transfected (B16D14KbKd) were kindly provided by Dr. Michel Sadelain, MSKCC. Cell lines were cultured in 10% defined calf serum (Hyclone, Logan, Utah) in RPMI with 2 mM L-glutamine, 100 U/ml of penicillin (Sigma, St. Louis, Mo.), 100 ug/ml of streptomycin (Sigma), 5% $CO_2$ in a 37° C. humidified incubator. Normal human mononuclear cells were prepared from heparinized bone marrow samples by centrifugation across a Ficoll-Hypaque density separation gradient.

Antibodies

Monoclonal antibodies 3F8 (mouse IgG3) and 3G6 (mouse IgM), and 8H9 (mouse IgG1) reactive with neuroblastoma have been previously described. They were produced by as ascites and purified by affinity chromatography: protein A (Pharmacia, Piscataway, N.J.) for 3F8,[18] protein G (Pharmacia) for 8H9,[19] and Clq-sepharose (Pierce Chemicals) for 3G6.[~, 20] These antibodies are >90% pure by SDS-PAGE. F(ab')2 fragments were prepared by pepsin digestion as previously reported.[21] Anti-GD3 antibody (R24) was kindly provided by Dr. Paul Chapman of MSKCC.[22] FLOPC21, an IgG3 myeloma, was purchased from Sigma Chemicals, St. Louis, Mich. TIB114 (N.S.7) a hybridoma secreting an IgG3 control antibody was obtained from ATCC. Rabbit anti-asialo-GM1 antibody (Wako Pure Chemical Industries, Ltd, Osaka, Japan) diluted to 1 mg/ml of protein was administered at 200 ul ip on days 0, 1, 2, 7, 14, 21. Rituximab, anti-CD20 antibody was purchased from Genentech, Inc., CA.

Indirect Immunofluorescence 1 million target cells were washed in PBS and then spun at 180×g for 5 min. The pellets were then reacted with 100 μl of 15 μg/ml 8H9 at 4° C. for 1 hour. After washing the cells with PBS they were allowed to react with 100 μl FITC-conjugated goat F (ab')2 anti- mouse IgG+IgM, (Biosource International, Camarillo, Calif.) at 4° C.[18] Flow cytometric analysis was performed using FACSCalibur Immunocytometer (Becton-Dickinson Immunocytometry Systems, San Jose, Calif.).

Glucan 1,3-1,4-β-glucan derived from barley, 1,3-1,6-β glucan (Laminarin) from seaweed (Laminaria digitata), and mannan were purchased from Sigma Co. 1,3-1,6-β-glucan (Lentinan) was obtained from Drug Synthesis and Chemistry Branch, Developmental Therapeutics Program, Division of Cancer Treatment, National Cancer Institute, Bethesda, Md. Maitake mushroom glucan (containing 1,3-1,6-β-glucan extracted from Grifola frondosa) D-fraction was obtained from Maitake Products Inc., Paramus, N.J. Barley and oats β-glucans of various molecular sizes (measured by high performance size-exclusion chromatography [HPSEC] with multiple angle laser scattering [MALLS] detection) and viscosities (measured in cSt units) were obtained from Megazyme International Ireland Ltd., Bray, County, Ireland. Barley glucan was dissolved by boiling for 10 minutes in normal saline. A stock solution of Lentinan in DMSO (Sigma) was diluted in water before use.

Mice and Treatment

Athymic Balb/c and C57Bl/c mice were purchased from Jackson Laboratories, Bar Harbor, Me., and CB-17 SCID from Taconic. Tumor cells were planted (1-5×10(6) cells) in 100 ul of Madrigel (Sigma Co) subcutaneously. Following implantation, tumor sizes (maximum width and lengths) were measured. Tumor size was calculated as product of the 2 perpendicular diameters. Treatment studies started when tumor diameter reached 0.7 to 0.8 cm, usually by 14-21 days of tumor implantation. Mice received antibody treatment intravenously (by retroorbital injection) twice weekly and glucan by gavage every day for a total 3-4 weeks (21-8 days of glucan and 6-8 doses of antibody). Mice were weighed once a week and tumor size measured twice a week. Mice were sacrificed when tumors reached sizes that interfered with their well-being.

$^{51}$Chromium (51Cr) Release Assay$^{23}$

In brief, $2\times10^3$ of 51Cr-labeled target cells were mixed with effector cells in a final volume of 0.2 ml of medium in 96-well flat-bottomed microtiter plates (Costar, Cambridge, Mass.). The plates were incubated for 4 h at 37° C. in 5% CO2 and then centrifuged. 100 ul of assay supernatant was counted in a gamma counter. Target cell spontaneous chromium release ranged from 10 to 25%.

Results

Barley Glucan Synergizes with anti-GD2 Antibody 3F8 in Eradicating Human Neuroblastoma.

3F8 is a murine IgG3 monoclonal antibody specific for ganglioside GD2. It activates mouse and human complement, and mediates effective ADCC against human neuroblastoma cells in vitro. Barley glucan when administered orally at 400 ug qd had no appreciable effect on tumor growth compared to antibody 3F8 given i.v. alone. However, when barley glucan and 3F8 were used in combination, tumor growth was near totally suppressed. In >40% of mice, NMB7 tumors remained permanently suppressed even when treatment was stopped after 21 days. Similar observations were made with neuroblastoma cell lines derived from different sources: NMB7, LAN-1 (FIGS. 1 and 2) and SK-N-ER (data not shown). Barley glucan was equally effective when administered orally or intraperitoneally. In contrast, for the GD2-negative rhabdomyosarcoma, HTB82, 3F8 plus β-glucan treatment was ineffective (data not shown).

Dose Response Curve for ip Barley Glucan.

When the dose of intraperitoneal barley glucan was decreased 10-fold from 400 ug, it was clear that 4 ug was no longer effective in synergizing with MoAb 3F8 in suppressing NMB7 growth. Interestingly, both ip lentinan and po glucan (at 400 ug po qd) were also effective (FIG. 3).

Oral Barley Glucan is as Effective as ip Glucan

When oral barley glucan was studied in NMB7 tumor (FIG. 4) followed after treatment for 80 days, similar dose response was found, i.e. while 400 ug oral regimen was curative, breakthroughs were seen for the other dose levels, with 4 ug oral dose escaping sooner than 40 ug. Interestingly, 400 ug ip was only as effective as the 40 ug oral group, with late breakthrough tumor growths around the same time, unlike the 400 ug po group, where all tumors remained suppressed despite stopping all therapy after 21 days. Using the LAN1 tumor model, both 4 and 40 ug glucan were ineffective compared to 400 and 4000 ug of glucan per dose (FIG. 5). There was no significant body weight change in the treatment groups (after accounting for tumor growth) irrespective of dose of glucan or combination with antibody 3F8. At necropsy on day 21, there were no appreciable difference in the peripheral blood counts, cholesterol and blood chemistry between mice receiving different glucan doses. There was also no difference in the histologic appearances of organs in mice treated with glucan at any of the dose levels, when compared to control mice that received saline.

By the Oral Route, Only Certain Glucans, and Frequent Dosing were Effective.

For NMB7 tumors (FIG. 6), 400 ug oral maitake was effective in synergizing with antibody 3F8, although late breakthroughs were seen. A 5 day/week po barley glucan regimen was equally as effective as the daily regimen. In contrast, a once a week or twice a week schedule of barley glucan was ineffective (data not shown). For the faster growing LAN1 tumors (FIG. 7) unlike barley glucan (lot #1 and lot #2), po lentinan, PSK or mannan were all ineffective. The effect of Maitake glucan was not significantly different from glucan dose or 3F8 alone (FIG. 8). Glucan from barley was more effective than that from oat despite similarities in their molecular sizes (FIG. 11).

Barley Glucans of Large Molecular Weight is More Effective

In FIG. 9, barley glucans of different molecular sizes (40K, 123K, 183K, 254K, 359K) were tested at an oral dose of 40 ug. Anti-tumor effect improved with increasing molecular weights, such that glucan of 359K size was most effective. Nevertheless, at high doses (e.g. 400 ug) even the less effective sizes, 40K and 128K showed some benefit (092900megazyme.xls from folder megazyme). Glucan derived from oat also showed syngergistic anti-tumor effect when administered in the presence of 3F8. Both molecular size and viscosity appeared to be important for this anti-tumor effect. For example barley glucan (327K, >100 cSt or 250K, 25 cSt) and oat glucan (69 cSt or 20-30 cSt) were highly effective in synergizing with MoAb, whereas barley glucan of 137K and 5.6 cSt was not (FIG. 10).

Role of NK Cells in Glucan Effect.

Removal of NK cells using anti-Asialo GM1 antiserum eliminated a substantial amount, although not completely the anti-tumor activity of glucan (FIGS. 11 and 12). Moreover in beige mice glucan was effective in synergizing with 3F8 (data not shown), suggesting that at least part of the anti-tumor activity was mediated by NK-independent cytotoxicity.

IgG3-F(Ab')2 or IgG1 Antibodies do not have Substantial Anti-Tumor Activity (FIG. 13)

The role of Fc in mediating the anti-tumor effect of glucan was apparent when Fc was removed by pepsin or when IgG1 isotype (data not shown) was used. Neither was able to activate complement or mediate efficient ADCC, and neither has significant anti-tumor effect when administered with 400 ug of oral glucan.

Barley Glucan Synergizes with Other Complement Fixing Antibodies in a Wide Spectrum of Human Tumors.

IgG3 anti-GD3 antibody R24 synergized with po glucan in shrinking melanoma SKMel-28 xenografts (FIG. 14). Rituximab (humanized IgG1 anti-CD20) synergized with po glucan in eradicating EBV-lymphoma, Daudi lymphoma, and Hodgkin's disease. Although anti-EGF-R antibody 428 (mouse IgG2a) was able to suppress epidermal carcinoma[40] A431 tumor growth, 428 plus oral glucan was much more effective in eradicating tumors.

|  | Cell line | Antibody |
|---|---|---|
| Subcutaneous tumor models | | |
| Human xenografts | NMB7 | 3F8 |
|  | LAN-1 | 3F8 |
|  | SK-N-ER | 3F8 |
|  | SK-N- | 3F8 |
|  | SKMel-28 | R24 |
|  | EBV-lymphoma | Rituximab |
|  | Daudi lymphoma | Rituximab |
|  | Hodgkin's disease | Rituximab |
|  | Epidermal Carcinoma 528 | |
| Syngeneic tumors | EL4 | 3F8 |
|  | B16D14 | 3F8 |
|  | B16D14-Kb | 3F8 |
|  | B16D14-Kb-Kd | 3F8 |
| Metastatic tumor models | | |
| Human xenografts | Daudi | 3F8 |
| Syngeneic tumors | EL4 | 3F8 |

Glucan Synergizes with 3F8 in C57Bl/6 Mice Against Syngeneic Tumors.

While our early experiments were focused on human xenografts in athymic or SCID mice, similar synergism was observed in immunologically intact mice grafted with GD2-positive B16 melanomas (B16D14 [FIG. 15], B16D14Kb, or B16D14KbKd [FIG. 16]) or GD2-positive EL4 lymphoma [FIG. 18]. Neither barley glucan nor 3F8 by itself showed anti-tumor effect. In contrast the combination of glucan and 3F8 was able to suppress almost entirely tumor growth in C57Bl/6 mice. In control B16 tumors which were GD2-negative, glucan plus 3F8 had no anti-tumor effect. We conclude that the glucan effect observed was not restricted to immune deficient animals. In addition, it requires tumor-specific antibodies, i.e. effective only if tumor cells carried the target antigen.

Glucan Synergizes with 3F8 in C57Bl/6 Mice Against Metastatic Tumors.

When EL4 lymphoma cells were injected iv, mice developed widespread tumors in their lungs, livers and at the site of injection and rapidly succumbed. Control animals were dead by 14 days following EL4 injection, while the group treated withi.v.3F8 plus 400 ug glucan po (treatment initiated 5 days following EL4 injection) had significantly longer survival.

Barley Glucan Syngergizes with 3F8 in Prolonging Survival

Nude mice (n=21) with established neuroblastoma NMB7 xenografts (0.7-0.8 cm diameter tumor at the beginning of treatment) were treated with 3F8 (200 ug twice a week iv) and 400 ug of barley β-glucan po daily for a total of 3 weeks. Control mice (n=21) received either saline alone, 3F8 alone, or β-glucan alone. Median survival was 30 days in control and >300 days in the treatment (3F8 plus β-glucan) group (p<0.001). Long-term survival was 56% in the treatment group and 5% in the control group (FIG. 19). In nude mice bearing established LAN1 xenografts (also 0.7-0.8 cm diameter tumor at the beginning of treatment) median survival increased from 20 days in the control group (n=38) to 42 days in the 3F8 plus glucan group (n=48) (p<0.001, FIG. 20).

Discussion

Using the human xenograft and syngeneic mouse tumor models, we have made the following observations. Glucan derived from barley or oats can synergize with monoclonal antibodies in suppressing or eradicating tumors, while β-glucan or antibody alone has little anti-tumor effect. Anti-tumor response requires antibodies that activate complement, whether mouse IgM, mouse IgG3 or human IgG1. Glucans of high molecular weight 250K and viscosity (20 cSt) possess this special effect. Oral route is at least equally (if not more) effective than the intraperitoneal route. It is a dose-dependent phenomenon, where 400 ug per dose is required for maximal effect. Natural killer cells are not essential for this glucan phenomenon, although they contribute to the anti-tumor effect. Normal I-cells and B-cells are not required for the anti-tumor effect since immune-deficient mouse strains demonstrate the glucan effect, whether athymic, SCID or SCID-beige mice are used. In addition, normal I-cells and B-cells do not interfere with this glucan effect, as shown in the syngeneic C57Bl/6 mouse model. Most importantly, oral glucan is well-tolerated by all the mice tested so far, with no noticeable change in body weight, blood counts or organ histologies, even at doses as high as 4 mg per dose per day.

Our findings differ significantly from previous observations and predictions on the use of glucans in cancer treatment. In the past it was thought that the 1,3-1,6-βlinkage was absolutely required for the glucan anti-tumor effect.[17] This structure contains 1,3-β-D-glucopyranosyl units along which are randomly dispersed single β-D-glucopyranosyl units attached by 1,6- linkages, giving a comb-like structure (e.g. Lentinan, Schizophyllan, Laminarin, and glucan from Baker's yeast). In these models, it was believed that T-cells cells were activated and indeed required for the anti-tumor effect. In addition, it was believed that small molecular weight glucan should be more effective than high molecular weight glucan and that the most effective administration should be intravenous or intraperitoneal routes. Indeed, Betafectin (PGG) was derived from a genetically engineered *Saccharomyces cerevisiae* which makes 1,3-1,6-β-D glucans with weaker interchain associations.[24] It was manufactured fori.v-.injection to improve macrophage function in the hope of reducing infectious complications and improving wound healing. Barley glucan is a linear polymer with 1,3 and 1,4 linkages; however, it is not a comb like structure. We did not find any anti-tumor effect of barley glucan when given alone. However, when used in combinations with monoclonal antibodies, the synergistic effect was remarkable. In addition, glucans of high molecular weight and high viscosity appeared to be most effective, contrary to what one might expect for macromolecular transport. Although barley glucan activates granulocyte mediated ADCC in vitro (data not shown), the effects of glucan may be indirect. It is not clear if the absorption of glucan is necessary for its anti-tumor effect. The exact mechanism of how barley glucan enhances the anti-tumor effect of monoclonal antibodies in vivo is unknown.

One possible mechanism of action may relate to innate receptors for β-glucan, in a hard-wired information network on phagocytes and lymphoid cells; receptors that normally recognize death signals and microbial molecular patterns.[25] Monoclonal antibodies, either through Fc interaction or through CR3 interaction with iC3b, direct cytotoxicity to tumor cells, a process greatly enhanced by β-glucan activation of effector cells. This killing is immediate, nonclonal, and obligatory, a process often referred to as innate immunity. The consequence of this innate effector arm is the activation of costimulatory molecules and induction of cytokines and chemokines that will enhance adaptive immunity to the tumor cells. Thus, activation of immunity is based upon discrimination between dangerous and nondangerous antigens; and if cancer can be viewed as constant danger to the immune system,[26,27] memory T-cells will not become tolerized. β-glucan receptors belong to a family of pattern recognition receptors (PRRs) specific for pathogen-associated molecular patterns (PAMPs). They are biosensors for invading pathogens widely distributed in vertebrate and invertebrate animals,[28] a nonclonal host defense pathway with structural and functional homologies in phylogenetic lineages that diverged over a billion years ago. A limited set of conserved signaling modules such as Toll/IL-1R homology domain, the SIIK domain, the Rel homology domain and perhaps the leucine rich regions (LRR) domain, represent the original building blocks for PRRs. For example, insects respond to infection by rapid and transient synthesis of antimicrobial peptides by the fat body and hemocytes. In drosophila antibacterial peptides (cecropin, attacin and definsin) and anti-fungal peptide drosomycin are dependent on the Toll pathway; this PRR activates a proteolytic cascade to act on Spatzle, or 18-Wheeler (18W) to form the active ligand for Toll. Activation of the human Toll homologue results in induction of IL-1, IL-6, IL-8, B7.1 and B7.2. With B7, signaling through CD28 occurs; T-cell become activated followed by expression of surface molecules such as TNF-α and TNF-β, Fas ligand (L), CD40L, CD30L, and CD27L, as well as secretion of cytokines. Interestingly, for dendritic cells, when they express B7, they stop antigen uptake (i.e. becoming nonendocytic) and assume their antigen-presenting role. Certain activation motifs such as LRR are present in Toll and the endotoxin receptor CD14; they are also present intracellularly in plants, probably responsible for resistance to intracellular pathogens.[28]

Carbohydrate-rich antigens on bacteria or fungi can activate complement. Alternatively, specific antibodies can also deposit complement components on pathogens or cancer cells, such as the C3b fragment of C3, which is rapidly proteolyzed into iC3b fragment by serum factor I. These iC3b fragments can glue pathogens or tumor cells to the iC3b-receptors (CR3, CD11b/CD18) on phagocytic cells and NK cells, stimulating phagocytosis and/or cytotoxic degranulation. Thus, antibody and complement link innate and adaptive immunity by targeting antigens to different cells of the immune system, e.g. via CR3 and Fc for phagocytic cells, CR2 for B cells, and CR1, CR2, or CR3 for follicular dendritic cells.[29] For neutrophils, CR3-dependent phagocytosis requires ligation of two distinct binding sites, one for iC3b and a second site for β-glucan. Without β-glucan, iC3b-opsonized target cells are resistant to killing.[30] Microbes possess polysaccharides that can activate the lectin domain on CR3, leading to phagocytosis and cytotoxic degranulation. In contrast, human cells (including tumors) lack these CR3-binding polyscccharides, thus the inability of CR3 to mediate phagocytosis or extracellular cytotoxicity of tumor cells opsonized with iC3b. The lectin site of CR3 can also influence transmembrane signaling of endogenous neutrophil membrane GPI-anchored glycoproteins (CD14, CD16, CD59, CD87[uPAR]). In a mouse mammary tumor model, where there is naturally occurring IgM and IgG antibodies, injection of yeast soluble β-glucan could suppress tumor growth, an effect lost in C3-deficient or CD11b (CR3)-deficient mice.[31,32] Since iC3b bound to a primary protein antigen can also enhance recognition and specific antibody synthesis by antigen-specific B cells,[33] the presence of glucan plus complement activation may enhance B-cell response to pathogens or tumor cells.

If this syngergistic effect of β-glucan on antibodies is active in humans, our findings may have broad clinical implications. First the efficacy of monoclonal antibodies in cancer (e.g. Herceptin, Rituximab, Dacluzimab, anti-GD2 and anti-EGF-R MoAb) can be potentially enhanced.[34] Nevertheless, even though toxicity from glucan is expected to be minimal, the enhanced efficacy of MoAb may also increase MoAb-mediated toxicity. For example, the side effects of Herceptin on cardiac function, or anti-GD2 MoAb on neuropathic pain may be increased. Second, since the amount and quality of barley and oat glucan in daily food intake can vary, future interpretations of efficacy trials using MoAb may need to take this into account, for both preclinical and clinical studies. Indeed since glucan synergizes equally well with IgM antibody, the presence of natural IgM anti-tumor and anti-viral antibodies can be a confounding factor in interpreting in vivo tumor response, whether in preclinical models or in clinical trials, unless the po intake of glucan in mouse chow is standardized. Most importantly, since many carbohydrate tumor vaccines (e.g. GM2-KLH,[35] GD2-KLH, MUC-1,[36] and globo-H-hexasaccharide[37]) induce primarily specific IgM response, glucan may enhance their anti-tumor effects. If this glucan effect can be generalized to other antibody-mediated host defense mechanisms, its role in infectious disease may also be intriguing. Serotherapy of certain drug resistant bacteria,[38] or viral (e.g. CMV) and fungal (e.g. cryptococcus and candida[39]) infections using antibodies may be enhanced by concurrent intake of β-glucan. One can speculate if the function of pre-existing protective antibodies, e.g. towards tetanus or streptococcus, can be enhanced by oral β-glucan; indeed, if it can enhance the protective effects of common bacterial vaccines. The successful treatment of Alzheimer's disease using antibodies specific for amyloid β-peptide in the mouse model is a provocative finding[44]; it is likely that β-glucan may enhance the antibody effect. When one consider glucan-effect in the context of auto-immune disease, it is also plausible that tissue injury may be increased by oral glucan, leading to exacerbations of such diseases as rheumatoid arthritis. It is possible in those auto-immune diseases in which auto-antibodies cause tissue damage, clinical signs and symptoms may be modulated by oral intake of glucan. In view of these potential beneficial and adverse effects of barley glucan on human diseases, a better understanding of their immune effects seems highly worthwhile.

REFERENCES

1. DiMaggio J J, Scheinberg D A, Houghton A N: Monoclonal antibody therapy of cancer. In: Pinedo H M, Chabner B A, Longo D L, (eds.): Cancer Chemotherapy and Biological Response Modifiers, Annual 11, Elsevier Science Publishers B. V., (Biomedical Division), 1990, pp 177-203

2. Schlom J: Monoclonal Antibodies in cancer therapy: Basic principles. In: DeVita V T, Hellman S, Rosenberg S A, (eds.): Biologic therapy of cancer, 2nd ed. Philadelphia, J. B. Lippincott Co, 1995, pp 507-520

3. Koehler G, Milstein C: Continuous culture of fused cells secreting antibody of pre-defined specificity. Nature 256:495-496, 1975

4. Moffat R, Pinsky C M, Hammershaimb L, et al: Clinical utility of external immunoscintigraphy with the IMMU-4 technetium-99m Fab' antibody fragment in patients undergoing surgery for carcinoma of the colon and rectum:results of a pivotal, phase III trial. The Immunomedics Study Group. J Clin Oncol 14(8):2295-2305, 1996

5. Maloney D G, Grillo-Lopez A J, Bodkin D J, et al: IDEC-C2B8: Results of a phase I multiple-dose trial in patients with relapsed non-hodgkin's lymphoma. J Clin Oncol 15:3266-3274, 1997

6. Cobleigh M A, Vogel C L, Tripathy D, et al: Multinational study of the efficacy and safety of humanized anti-HER2 monoclonal antibody in women who have HER2-overexpressing metastatic breast cancer that has progressed after chemotherapy for metastatic disease. J Clin Oncol 17:2639-2648, 1999

7. Bigner D D, Brown M T, Friedman A H, et al: Iodine-131-labeled antitenascin monoclonal antibody 8106 treatment of patients with recurrent malignant gliomas:phase I trial results. Journal Clincal Oncology 16:2202-2212, 1998

8. Jurcic J G, Caron P C, Miller W H, et al: Sequential targeted therapy for acute promyelocytic leukemia with all-trans retinoic acid and anti-CD33 monoclonal antibody M195. Leuk 9:244-248, 1995

9. Meredith R F, Khazaeli M B, Plott W E: Phase II study of dual 131I-labeled monoclonal antibody therapy with interferon in patients with metastatic colorectal cancer. Clin Can Res 2:1811-1818, 1996

10. Yeh S D, Larson S M, Burch L, et al: Radioimmunodetection of neuroblastoma with iodine-131-3F8: Correlation with biopsy, iodine-131-Metaiodobenzylguanidine (MIBG) and standard diagnostic modalities. J Nucl Med 32:769-776, 1991

11. Cheung N K V, Kushner B H, Cheung I Y, et al: Anti-GD2 antibody treatment of minimal residual stage 4 neuroblastoma diagnosed at more than 1 year of age. J Clin Oncol 16:3053-3060, 1998

12. Lanzavecchia A, Abrignani S, Scheidegger D, et al: Antibodies as antigens. The use of mouse monoclonal antibodies to focus human T cells against selected targets. J Exp Med 167:345-352, 1988

13. Jerne N K: Toward a network theory of the immune system. Ann Immunol (Paris) 125C:373-389, 1974

14. Janeway C A: Presidential address to the american association of immunologist. J Immunol 161:539-544, 1998

15. Liszewski M K, Farries T C, Lublin D M, et al: Control of the complement System. Adv Immunol 61:201, 1996

16. Kim Y S, Ryu J, Han S, et al: Gram-negative bacteria binding protein, a pattern recognition receptor for lipopolysaccharide and beta-1,3-glucan, which mediates the signaling for the induction of innate immune genes in drosophilia melanogaster cells. J Bio Chem 2000

17. Bohn J A, BeMiller J N: (1-3) β-D-Glucans as biological response modifiers:a review of structure-functional activity relationships. Carbohydrate Polymers 28:3-14, 1995

18. Cheung N K, Saarinen U, Neely J, et al: Monoclonal antibodies to a glycolipid antigen on human neuroblastoma cells. Cancer Res 45:2642-2649, 1985

19. Modak S, Gultekin S H, Kramer K, et al: Novel tumor-associated surface antigen: broad distribution among neuro-ectodermal, mesenchymal and epithelial tumors, with restricted distribution in normal tissues. Proceedings of ASCO 17:449a, 1998

20. Nethery A, Raison R L, Easterbrook-Smith S B: Single-step purification of immunologlobin M on Clq-sepharose. J Immunol Methods 126:57-60, 1990

21. Cheung N K V, Walter E I, Smith-Mensah W H, et al: Decay-accelerating factor protects human tumor cells from complement-mediated cytotoxicity in vitro. J Clin Invest 81:1122-1128, 1988

22. Houghton A N, Mintzer D, Cordon-Cardo C, et al: Mouse monoclonal antibody detecting GD3 ganglioside: a phase I trial in patients with malignant melanoma. Proc Natl Acad Sci USA 82:1242-1246, 1985

23. Munn D H, Cheung N K: Interleukin-2 enhancement of monoclonal antibody-mediated cellular cytotoxicity (ADCC) against human melanoma. Cancer Res 47:6600-6605, 1987

24. Zimmerman J W, Lindermuth J, Fish P A, et al: A novel carbohydrate-glycosphingolipid interaction between a beta-(1-3)-glucan immunomodulator, PGG-glucan, and lactosyl-ceramide of human leukocytes. J Biol Chem 273:22014-22020, 1998

25. Matzinger P: Tolerance, danger and the extended family. Annu Rev Immunol 12:991-1045, 1994

26. Fuchs E J, Matzinger P: Is cancer dangerous to the immune system. Seminars in Immunology 8:271-280, 1996

27. Matzinger P: An innate sense of danger. Seminars in Immunology 10:399-415, 1998

28. Medzhitov R, Janeway C A: An ancient system of host defense. Curr Opin Immunol 10:12-15, 1998

29. Vivanco F, Munoz E, Vidarte L, Pastor C: The cavalent interaction of C3 with IgG immune complexes. Mol Immunol 36:843-852, 1999

30. Vetvicka V, Thornton B P, Ross G D: Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells. Journal of Clinical Investigations 98:50-61, 1996

31. Yan J, Vetvicka V, Xia Y, et al: B-glucan a "Specific" biologic response modifier that uses antibodies to target tumors for cytotoxic recognition by leukocyte complement receptor type 3 (CD11b/CD18). J Immunol 163:3045-3052, 1999

32. Xia Y, Vetvicka V, Yan J, et al: The beta-glucan-binding lectin site of mouse CR3 (CD11b/CD18) and its function in generating a primed state of the receptor that mediates cytotoxic activation in response to iC3b-opsonized target cells. J Immunol 162:2281-2290, 1999

33. Thornton B P, Vetvicka V, Ross G D: Function of C3 in a humoral response: iC3b/C3dg bound to an immune complex generated with natural antibody and a primary antigen promotes antigen uptake and the expression of co-stimulatory molecules by all B cells, but only stimulates immunoglobulin synthesis by antigen-specific B cells. Clin Exp Immunol 104: 531-537, 1996

34. Jurianz K, Maslak S, Garcia-Schuler H, et al: Neutralization of complement regulatory proteins augments lysis of breast carcinoma cells targeted with rhumAb anti-HER2. Immunopharmacology 42:209-218, 1999

35. Livingston P O, Wong G Y C, Adluri S, et al: Improved survival in stage III melanoma patients with GM2 antibodies: a randomized trial of adjuvant vaccination with GM2 ganglioside. J Clin Oncol 12:1036-1044, 1994

36. Kotera Y, Fontenot J D, Pecher G, et al: Humoral immunity against a tandem repeat epitope of human mucin MUC-1 in sera from breast, pancreatic, and colon cancer patients. Cancer Res 54:2856-60, 1994

37. Slovin S F, Ragupathi G, Adluri S, et al: Carbohydrate vaccines in cancer: Immunogenicity of a fully synthetic globo H hexasaccharide conjugate in man. Proc Natl Acad Sci USA 96:5710-5715, 1999

38. Casadevall A: Antibody-based therapies for emerging infectious diseases. Emerging Infectious Diseases 2: 1996

39. Han Y, Riesselman M H, Cutler J E: Protection against candidiasis by an immunoglobulin G3 (IgG3) monoclonal antibody specific for the same mannotriose as an IgM protective antibody. Inf Imm 68:1649-1654, 2000

40. Waksal H W: Role of an anti-epidermal growth factor receptor in treating cancer. Cancer and Metastatsis Reviews 18:427-436, 1999

41. Agus D B, Scher H I, Higgins B, et al: Response of prostate cancer to anti-her-2/neu antibody in androgen-dependent and independent human xenograft models. Advances in Brief 59:4761, 1999

42. Scott A M, Geleick D, Rubira M, et al: Construction, production, and characterization of humanized anti-lewis Y monoclonal antibody 3S193 for targeted immunotherapy of solid tumors. Cancer Res 60:3254-3261, 2000

43. Clarke K, Lee F, Brechbiel M W, et al: Therapeutic efficacy of anti-Lewis humanized 3S193 radioimmunotherapy in a breast cancer model: enhanced activity when combined with taxol chemotherapy. Clin Can Res 6:3621, 2000

44. Bard F, Cannon C, Barbour R, et al: Peripherally administered antibodies against amyloid B-peptide enter the central nervous system and reduce pathology in a mouse model of Alzheimer disease. Nature Medicine 6:916-919, 2000

Second Series of Experiments

Purpose: In vitro β-glucan can enhance tumor cytotoxicity through iC3b receptors on leukocytes. We test if (1→3), (1→4)-β-D-glucan (β-glucan) can synergize with anti-GD2 monoclonal antibody (MoAb) 3F8 (mouse IgG3) in therapy of human neuroblastoma xenografts.

Experimental Design: Athymic nude mice with established neuroblastoma xenografts were treated with daily intraperitoneal or oral β-glucan, in the presence/absence of intravenous MoAb twice a week, for 22-29 days. Serial tumor volumes and body weights were monitored.

Results: 3F8 plus β-glucan produced near-complete tumor regression/disease stabilization, while 3F8 or β-glucan alone did not significantly affect tumor growth. For NMB7 tumors, median survival of 3F8 plus β-glucan group was 5.5 fold that of control groups (p<0.001), and for LAN-1 the survival difference was 2.6 fold. 47% of the mice with NMB7 and 18% with LAN-1 remained progression-free in contrast to <3% of controls. Antitumor effect was seen at ∃40 ug glucan dose, i.v. or po, and in all human neuroblastoma cell lines tested. No toxicities were noted in mice treated with either β-glucan alone or 3F8 plus β-glucan (4 to 4000 ug per dose). In contrast to anti-GD2 MoAb 3G6 (IgM), 3F8 F(ab')$_2$ and MoAb 8H9 (IgG1) did not activate complement and had no synergy with β-glucan. Anti-tumor effect of 3F8 plus oral β-glucan persisted after anti-asialo-GM1 antibody treatment, as well as in NK-deficient host.

Conclusions: Oral 1,3-1,4-β-glucan synergized with antitumor IgG and IgM MoAb in vivo. Since β-glucan was well tolerated and inexpensive, its potential value in cancer therapy deserves further investigation.

Introduction

Monoclonal antibodies (MoAb) selective for tumors have therapeutic potential (1). The introduction of hybridoma technology by Kohler and Milstein in 1975 (2) and advances in molecular biologic techniques have greatly expanded the potential of MoAb in human cancers. Evidence of efficacy in clinical trials is increasingly evident: 17-1A in colon cancers (3), anti-CD20 in lymphoma (4, 5), anti-HER2 antibodies in breast cancer (6, 7), and M195 against CD33 in acute leukemia (8) are good examples. Our laboratory has developed the MoAb 3F8 which targets the ganglioside GD2 overexpressed on neuroblastoma. 3F8 has been shown to have high specificity and sensitivity in the radioimmunodetection of minimal residual disease in patients with NB (9), and a significant clinical impact when used as adjuvant therapy (10).

The immune basis of clinical tumor response to MoAb is at least two-fold, direct cytotoxicity and induced immunity. Antibody dependent cell-mediated cytotoxicity (ADCC) and complement mediated cytotoxicity (CMC) are responsible for the direct killing of tumor cells. On the other hand, through tumor opsonization (11) or idiotype network (12), tumor-specific immunity is induced. β-glucans are polymers of glucose extractable from cereals, mushrooms, seaweed and yeasts (13). They are (1→3)-β-D-glucopyranosyl polymers with randomly dispersed single β-D-glucopyranosyl units attached by (1→6)-linkages, giving a comb-like structure. The (1→3)-β backbone and the (1→6)-linked branches were thought to be important for their immune effects. Lentinan (from *Lentinus edodes*, *Basidiomycete* family) is a high molecular weight (MW) β-glucan with (1→6) branches off every three (1→3)-β-D-glucopyranosyl residues and it has been licensed in Japan for cancer treatment. Schizophyllan (from *Schizophyllum commune*, *Basidiomycete* family) and β-glucan from Baker's yeast (*Saccharomyces cerevisiae*) have similar structures. Laminarin (from seaweed), a small MW β-glucan, has (1→6)-β branches occurring at every ten (1→3)-β-D glucopyranosyl units. On the other hand, β-glucan from barley, oat or wheat has mixed (1→3) and (1→4)-β-linkage in the backbone, but no (1→6)-β branches and are generally of high MW. Although barley (1→3), (1→4)-β-D-glucan has been shown in vitro to bind to CR3 (14), activate ADCC mediated by natural killer cells (15-17), monocytes (18, 19), and neutrophils (17, 19), as well as stimulating tumor necrosis factor (TNFc) production by monocytes (20), their in vivo immunomodulatory effects in cancer models have yet to be investigated.

We now report our findings that oral (1→3), (1→4)-β-D-glucan derived from barley or oats can greatly enhance the activity of anti-tumor monoclonal antibodies in xenograft models. Because β-glucan is nontoxic, well tolerated and inexpensive, its role in cancer therapy deserves careful study.

Materials and Methods

Cell lines Human neuroblastoma cell lines LAN-1 were provided by Dr. Robert Seeger, Children's Hospital of Los Angeles, Los Angeles, Calif., and NMB7 by Dr. Shuen-Kuei Liao (McMaster University, Ontario, Canada). Neuroblastoma cell lines SK-N-JD, SK-N-ER, and SK-N-MM were established from patients with metastatic disease treated at Memorial Sloan-Kettering Cancer Center (MSKCC), New York, N.Y. Cell lines were cultured in 10% defined calf serum (Hyclone, Logan, Utah) in RPMI with 2 mM L-glutamine, 100 U/ml of penicillin (Sigma, St. Louis, Mo.), 100 ug/ml of streptomycin (Sigma), 5% $CO_2$ in a 37° C. humidified incubator. Normal human mononuclear cells were prepared from heparinized bone marrow samples by centrifugation across a Ficoll density separation gradient.

Antibodies Monoclonal antibodies 3F8 (mouse IgG3), 3G6 (mouse IgM), and 8H9 (mouse IgG1) reactive with neuroblastoma have been previously described (21, 22). They were produced as ascites and purified by affinity chromatography: protein A (Pharmacia, Piscataway, N.J.) for 3F8 (21), protein G (Pharmacia) for 8H9 (22), and C1q-sepharose (Pierce, Rockford, Ill.) for 3G6 (21, 23). These antibodies were >90% pure by SDS-PAGE. F(ab')$_2$ fragments were prepared by pepsin digestion as previously reported (24). TIB114 (N.S.7), a hybridoma secreting an IgG3 control antibody, was obtained from American Type Culture Collection (ATCC). Rabbit anti-asialo-GM1 antibody (Wako Pure Chemical Industries, Osaka, Japan) diluted to 1 mg/ml of protein was administered at 200 ul ip on days 0, 1, 2, 7, 14, 21.

Glucan (1→3), (1→4)-β-D-glucan derived from barley and (1→4)-β-D-mannan were purchased from Sigma. Sugar composition and linkage analysis were performed by the Complex Carbohydrate Research Center, University of Georgia, Athens, Ga., supported in part by the Department of Energy-funded Center for Plant and Microbial Complex Carbohydrates (DF-FG09-93ER-20097). Barley glucan was dissolved by boiling for 10 minutes in normal saline.

Mice and treatment Athymic Balb/c mice were purchased from NCI, Frederick, Md., and CB-17 SCID-Beige mice from Taconic (Germantown, N.Y.). Tumor cells were planted ($1-5\times10^6$ cells) in 100 ul of Matrigel (BD BioSciences, Bedford, Mass.) subcutaneously. Following implantation, tumor sizes (maximum width and lengths) were measured. Tumor size was calculated as product of the 2 perpendicular diameters. Treatment studies started in groups of 4-5 mice per cage when tumor diameter reached 0.7 to 0.8 cm, usually by 14-21 days of tumor implantation. Mice received antibody treatment intravenously (generally 200 ug per dose by retroorbital injection) twice weekly and β-glucan by intragastric gavage (generally 400 ug per dose) every day for 3 weeks (22-days of β-glucan and 6-doses of antibody). Mice were weighed once a week and tumor size measured twice a week. Mice were sacrificed when tumors reached sizes that interfered with their well-being.

Assays for soluble cytokines Sera from mice were obtained 1 h, 4 h, 8 h, 24 h, 48 h, and 72 h after oral β-glucan. They were assayed for soluble cytokine IL-12 (p70) and TNFα, all reagents from Endogen (Woburn, Mass.). Briefly, 96-well microtiter plates were coated with either monoclonal anti-mouse IL12 at 5 ug/ml or monoclonal anti-TNF=α at 0.8 ug/ml overnight at ambient temperature. The mouse IL12 standard ranged from 1000 pg/ml in 1:3 serial dilutions and the TNF=α standard ranged from 490 pg/ml in 1:2 serial dilution. Test samples (serum diluted 1:2) were added to the plates and incubated for 2 hours at ambient temperature. The detecting antibody, biotinylated anti-mouse IL12 monoclonal at 1:100 dilution for the IL12 assay, or biotinylated anti-mouse TNF=α monoclonal at (1:50) for the TNF=α ELISA was added. The plates were incubated at ambient temperature for one hour. After PBS wash, the secondary antibody, which was HRP-conjugated streptavidin at 1:400 for IL12, and 1:200 for TNF=α, was added to the plates for a 30 min incubation at ambient temperature. After another wash, tetramethylbenzidine was added as the substrate for the color reaction for 30 min, and absorbance was read at 450 nm using an ELISA plate reader. The limits of detection were 12 pg/ml for the mouse IL12 ELISA, and 10 pg/ml for the mouse TNF=α ELISA.

Immunostaining for tumor vasculature LAN-1 xenografts were removed 1 h, 4 h, 8 h, 16 h, 24 h, 48 h, 96 h and 216 h after treatment. Tumor vasculature was assayed by immunostaining with an anti-blood vessel antibody. Eight mm cryostat frozen tumor sections were fixed in acetone and washed in PBS. Endogenous peroxidases were blocked in 0.3% $H_2O_2$ in PBS. Sections were incubated in 3% bovine serum albumin containing 0.25% gelatin for 60 minutes, after the avid-biotin blocking step. Incubation with the biotinylated rat anti-murine PECAM IgG2a MoAb, MEC13.3 (1 mg/ml) (BD PharMingen, SanDiego, Calif.) was carried out at room temperature for 60 minutes followed by ABC complex (Vector Laboratories, Burlingame, Calif.). Color was developed with DAB peroxidase substrate kit (Vector). A 10% hematoxylin counterstain for 4 minutes was used.

Statistical analysis Average tumor size over time between groups was compared. The null hypothesis was no difference in size over time. To test the hypothesis, the square of size differences summed over time was used, which in effect compared the trajectories of the average tumor sizes between treatment groups.

$$SS\_DEV \stackrel{k}{\underset{i=1}{=}} 3(x_i - y_i)^2$$

where there were k time points and $x_i$ and $y_i$ were the average tumor sizes at time i for each treatment group.

Results

Synergy between barley β-glucan and anti-GD2 antibody 3F8 in eradicating human neuroblastoma. 3F8 is a murine IgG3 monoclonal antibody that activates mouse and human complement, and mediates effective ADCC against human neuroblastoma cells in vitro. β-glucan when administered orally at 400 ug per day had no appreciable effect on NMB7 tumor growth as did antibody 3F8 giveni.v.alone. However, when β-glucan and 3F8 were used in combination, tumor growth was near totally suppressed. In >47% of mice, tumors remained permanently suppressed following treatment. Similar observations were made with neuroblastoma cell lines derived from different sources: LAN-1 (FIG. 21a), NMB7 (FIG. 21b) SK-N-ER (FIG. 21c), SK-N-MM and SK-N-JD (data not shown). β-glucan was equally effective when administered orally or intraperitoneally. In contrast, for the GD2-negative rhabdomyosarcoma, HTB82, 3F8 plus β-glucan treatment was ineffective (data not shown). In addition, TIB114 (IgG3 control) plus barley β-glucan, or 3F8 plus mannan had no anti-tumor (data not shown). When 3F8 dose was decreased from 200 ug to 40 ug, the anti-tumor effect was lost (data not shown). There was no detectable serum IL-12 or TNF-α release following oral β-glucan administration (data not shown). There was no immunohistochemically detectable effect of β-glucan on tumor vessel formation (data not shown).

Dose response curve for ip β-glucan. When the dose of intraperitoneal β-glucan was decreased by 10-fold from 4000 ug, it was clear that 4 ug was no longer effective in synergizing with MoAb 3F8 in suppressing NMB7 growth. Interestingly, both ip and oral 1,3-1,4-β-glucan (at 400 ug per day) were effective (FIG. 22).

Oral β-glucan versus ip β-glucan. When oral β-glucan was studied in NMB7 tumors (FIG. 23), similar dose response was found. While an oral dose of 400 ug was curative for some tumors, breakthroughs were seen for lower dose levels, with those receiving 4 ug escaping sooner those receiving 40 ug. Using the LAN-1 tumor model, neither 4 nor 40 ug β-glucan were effective (data not shown). There was no significant body weight change in any of the treatment groups (after accounting for tumor weight), irrespective of β-glucan dose or co-administration with 3F8. At necropsy on day 22, there were no appreciable differences in the peripheral blood counts, cholesterol and blood chemistry between mice receiving different β-glucan doses. There was also no difference in the histologic appearances of organs in mice treated with β-glucan at any of the dose levels, when compared to control mice that received saline.

By the oral route, daily β-glucan schedule was necessary. A 5 day/week po β-glucan regimen was comparable to the daily regimen. In contrast, a once a week or twice a week schedule of β-glucan had no anti-tumor effect (data not shown).

Role of NK cells in β-glucan effect. Removal of NK cells by anti-Asialo GM1 antiserum eliminated a substantial amount, although not completely the anti-tumor activity of β-glucan (FIG. 24). Moreover, in SCID-beige mice which lack NK cells, β-glucan was still effective in synergizing with 3F8 (data not shown), suggesting that at least part of the anti-tumor activity was mediated by NK-independent cytotoxicity.

IgG3-F(ab')$_2$ or IgG1 antibodies did not have anti-tumor activity. The role of Fc in mediating the anti-tumor effect of β-glucan was apparent when Fc was removed by pepsin or when IgG1 isotype MoAb 8H9 was used (data not shown). Neither was able to activate complement or mediate efficient ADCC, and neither has significant anti-tumor effect when administered with 400 ug of oral β-glucan.

Synergy of β-Glucan with 3F8 in prolonging survival. Nude mice (n=22) with established neuroblastoma NMB7 xenografts (0.7-0.8 cm diameter tumor at the beginning of treatment) were treated with 3F8 (200 ug twice a week iv) and 400 ug of β-glucan po daily for a total of 3 weeks. Control mice received either saline alone (n=10), 3F8 alone (n=8), or β-glucan (n=16) alone. Median survival was 30 days in control groups and 166 days in the treatment (3F8 plus β-glucan, n=22) group (p<0.001). Long-term survival was estimated at 47% in the treatment group and 3% in the control group (saline alone, 3F8 alone, or β-glucan alone) (FIG. 25). Similar experiments were carried out in nude mice bearing established LAN-1 xenografts (also 0.7-0.8 cm diameter tumor at the beginning of treatment). Among control mice treated with either saline alone (n=31), 3F8 alone (n=16), or β-glucan (n=8) alone, tumor growth was rapid. Median survival was 21 days in control groups (n=55) and 54 days in the treatment (3F8 plus β-glucan) group (n=82) (p<0.001, FIG. 26). Long-term survival was estimated at 18% in the treatment group and 0% in the controls.

Discussion

Using the human xenograft models, we have made the following observations. β-Glucan derived from barley can synergize with monoclonal antibodies to suppress and/or eradicate tumors, while β-glucan or antibody alone has little anti-tumor effect. Anti-tumor response requires antibodies that activate complement, and both mouse IgM and mouse IgG3 were effective. Oral administration of β-glucan is at least equally (if not more) effective than the intraperitoneal route. It is a dose-dependent phenomenon, where ≥400 ug per dose is required for maximal effect. Natural killer cells are not essential for this β-glucan phenomenon, although they contribute to the anti-tumor effect. Normal I-cells and B-cells are not required for the anti-tumor effect since immune-deficient mouse strains demonstrate the β-glucan effect, in both athymic and SCID-beige mice. Most importantly, oral β-glucan is well-tolerated by all the mice tested so far, with no noticeable change in body weight, blood counts or organ histologies, even at doses as high as 4 mg per dose per day.

Our findings differ significantly from previous observations and predictions on the use of β-glucans in cancer treatment. In the past it was thought that the (1→3), (1→6)-β linkage was absolutely required for the β-glucan anti-tumor effect (13). This structure contains (1→3)-β-D-glucopyranosyl units along which are randomly dispersed single β-D-glucopyranosyl units attached by (1→6)-linkages, giving a comb-like structure (e.g. Lentinan, Schizophyllan, Laminarin, and glucan from Baker's yeast). In these models, it was believed that T-cells were activated and indeed required for the anti-tumor effect. In addition, it was believed that small molecular weight β-glucan should be more effective than high molecular weight β-glucan and that the most effective administration should be intravenous or intraperitoneal routes. Indeed, Betafectin was derived from a genetically engineered *Saccharomyces cerevisiae* which makes (1→3), (1→4)-β-D-glucans with weaker interchain associations (25). It was manufactured for i.v. injection to improve macrophage function in the hope of reducing infectious complications and improving wound healing. Barley β-glucan is a linear polymer with (1→3)-β and (1→4)-β linkages; however, it is not a comb like structure. We did not find any anti-tumor effect of barley β-glucan when given alone. However, when used in combinations with monoclonal antibodies, the synergistic effect was remarkable. Although β-glucan activates granulocyte mediated ADCC in vitro (data not shown), the effects of β-glucan may be indirect. It is not clear if the absorption of β-glucan is necessary for its anti-tumor effect. The exact mechanism of how β-glucan enhances the anti-tumor effect of monoclonal antibodies in vivo is unknown.

Monoclonal antibodies, either through Fc interaction or through CR3 interaction with iC3b, target cytotoxicity to tumor cells, a process greatly enhanced by β-glucan activation of effector cells. β-glucan activates leukocytes by binding to CR3 or to β-glucan receptors (26). After antibodies deposit complement components on pathogens or cancer cells, C3b is rapidly proteolyzed into iC3b fragment by serum factor I. These iC3b fragments then opsonize the pathogens or tumor cells for the iC3b-receptors (CR3, CD11b/CD18) on phagocytic cells and NK cells, stimulating phagocytosis and/or cytotoxic degranulation. Thus, antibody and complement link innate and adaptive immunity by targeting antigens to different cells of the immune system, e.g. via CR3 and Fc for phagocytic cells, CR2 for B cells, and CR1, CR2, or CR3 for follicular dendritic cells (27). For neutrophils, CR3-dependent phagocytosis requires ligation of two distinct binding sites, one for iC3b and a second site for β-glucan. Without β-glucan, iC3b-opsonized target cells are resistant to killing (17). Microbes possess polysaccharides that can activate the lectin domain on CR3, leading to phagocytosis and cytotoxic degranulation. In contrast, human cells (including tumors) lack these CR3-binding polysaccharides, thus the inability of CR3 to mediate phagocytosis or extracellular cytotoxicity of tumor cells opsonized with iC3b. The lectin site of CR3 can also influence transmembrane signaling of endogenous neutrophil membrane GPI-anchored glycoproteins (e.g. CD14, CD16, and CD59). In a mouse mammary tumor model, where there are naturally occurring IgM and IgG antibodies, injection of yeast soluble β-glucan could suppress tumor growth, an effect lost in C3-deficient or CD11b (CR3)-deficient mice (28, 29). Since iC3b bound to a primary protein antigen can also enhance recognition and specific antibody synthesis by antigen-specific B cells (30), the presence of β-glucan plus complement activation may enhance B-cell response to pathogens or tumor cells.

Another mechanism of action of β-glucan may relate to innate receptors for β-glucan, in a hard-wired information network on phagocytes and lymphoid cells; receptors that normally recognize death signals and microbial molecular patterns (31). These innate receptors are biosensors for invading pathogens widely distributed in vertebrate and invertebrate animals (32), a nonclonal host defense pathway with structural and functional homologies in phylogenetic lineages that diverged over a billion years ago. Following β-glucan activation of leukocytes, killing is immediate, nonclonal, and obligatory, a process often referred to as innate immunity. The consequence of this innate effector arm is the activation of costimulatory molecules and induction of cytokines and chemokines that will enhance adaptive immunity to the tumor cells. (33, 34). Thus, antibodies, complement, phagocytes, and "danger" receptors form core elements of innate immunity while antigen-presenting cells, T and B lymphocytes constitute essential players in acquired immunity.

Despite the availability of tumor-selective monoclonal antibodies and the ample supply of phagocytes/natural killers, shrinkage of established tumors following antibody treatment alone, and the acquisition of specific immunity, are not common in both preclinical models and cancer patients. The absence of a danger signal and the diminution of complement action by complement resistance proteins on tumor cells may explain the inefficiency of antibody mediated clinical responses (35). Lipopolysaccharide and β-glucan, being cell wall components of bacteria and fungus, respectively, are potent danger signals to the immune systems in all life-forms, from Drosophila to man (36). While LPS is too toxic for human use, β-glucan is relatively benign. If this synergistic effect of β-glucan on antibodies is active in humans, our findings may have broad clinical implications. First the efficacy of monoclonal antibodies in cancer (e.g. Herceptin, Rituximab, Dacluzimab, anti-GD2 and anti-EGF-R MoAb) can be potentially enhanced (37). Nevertheless, even though toxicity from β-glucan is expected to be minimal, the enhanced efficacy of MoAb may also increase MoAb-mediated toxicity. For example, the side effects of Herceptin on cardiac function, or anti-GD2 MoAb on neuropathic pain may be increased. Second, since the amount and quality of barley and oat glucan in daily food intake can vary, future interpretations of efficacy trials using MoAb may need to take this into account, for both preclinical and clinical studies. Indeed since glucan synergizes equally well with IgM antibody, the presence of natural IgM anti-tumor and anti-viral antibodies can be a confounding factor in the interpretation of in vivo tumor response, whether in preclinical models or in clinical trials, unless the oral intake of glucan in mouse chow is standardized. Most importantly, since many carbohydrate tumor vaccines (e.g. GM2-KLH (38), GD2-KLH, and globo-H-hexasaccharide (39)) primarily induce specific IgM response, glucan may enhance their anti-tumor effects. In view of these potential beneficial effects of barley glucan on cancer therapy, a better understanding of their immune effects seems highly worthwhile.

REFERENCES FOR THE SECOND SERIES OF EXPERIMENTS

1. Schlom, J.: Monoclonal Antibodies in cancer therapy: Basic principles. In: V. T., DeVita, S., Hellman, S. A., Rosenberg (eds.), Biologic therapy of cancer, 2nd ed., pp. 507-520. Philadelphia: J.B.Lippincott Co, 1995.

2. Koehler, G., Milstein, C. Continuous culture of fused cells secreting antibody of pre-defined specificity. Nature, 256:495-496, 1975.

3. Riethmuller, G., Holz, E., Schlimok, G., Schmiegel, W., Raab, R., Hoffken, K., Gruber, R., Funke, I., Pichlamaier, H., Hirche, H., Buggisch, P., Witte, J., Pichlmayr, R. Monoclonal Antibody Therapy for Resected Dukes' C Colorectal Cancer: Seven-Year Outcome of a Multicenter Randomized Trial. J Clin Oncol, 16:1788-1794, 1998.

4. Maloney, D. G., Grillo-Lopez, A. J., Bodkin, D. J., White, C. A., Liles, T.-M., Royston, I., Varns, C.,
Rosenberg, J., Levy, R. IDEC-C2B8: Results of a phase I multiple-dose trial in patients with relapsed non-hodgkin's lymphoma. J Clin Oncol, 15:3266-3274, 1997.

5. McLaughlin, P., Grillo-Lopez, A. J., Kink, B. K., Levy, R., Czuczman, M. S., Williams, M. E., Heyman, M. R., Bence-Bruckler, I., White, C. A., Cabanillas, F., Jain, V., Ho, A. D., Lister, J., Wey, K., Shen, D., Dallaire, B. K. Rituximab chimeric anti-CD20 monoclonal antibody therapy for relapsed indolent lymphoma: half of patients respond to four-dose treatment program. J Clin Oncol, 16:2825-2833, 1998.

6. Cobleigh, M. A., Vogel, C. L., Tripathy, D., Robert, N. J., Scholl, S., Fehrenbacher, L., Wolter, J. M., Paton, V., Shak, S., Lieberman, G., Slamon, D. J. Multinational study of the efficacy and safety of humanized anti-HER2 monoclonal antibody in women who have HER2-overexpressing metastatic breast cancer that has progressed after chemotherapy for metastatic disease. J Clin Oncol, 17:2639-2648, 1999.

7. Slamon, D. J., Leylan-Jones, B., Shak, S., Fuchs, H., Paton, V., Bajamonde, A., Fleming, T., Eiermann, W., Wolter, J., Pegram, M., Baselga, J., Norton, L. Use of chemotherapy plus a monoclonal antibody against HER2 for metastatic breast cancer that overexpress HER2. N Engl J Med, 344:783, 2001.

8. Jurcic, J. G., DeBflasio, T., Dumont, L., Yah, T. J., Scheinberg, D. A. Molecular remission induction with retinoic acid and anti-CD33 monoclonal antibody HuM195 in acute promyelocytic leukemia. Clin Cancer Res, 6:372-380, 2000.

9. Yeh, S. D., Larson, S. M., Burch, L., Kushner, B. H., LaQuaglia, M., Finn, R., Cheung, N. K. V. Radioimmunodetection of neuroblastoma with iodine-131-3F8: Correlation with biopsy, iodine-131-Metaiodobenzylguanidine (MIBG) and standard diagnostic modalities. J. Nucl. Med., 32:769-776, 1991.

10. Cheung, N. K. V., Kushner, B. H., Cheung, I. Y., Canete, A., Gerald, W., Liu, C., Finn, R., Yeh, S. J., Larson, S. M. Anti-GD2 antibody treatment of minimal residual stage 4 neuroblastoma diagnosed at more than 1 year of age. J Clin Oncol, 16:3053-3060, 1998.

11. Lanzavecchia, A., Abrignani, S., Scheidegger, D., Obrist, R., Dorken, B., Moldenhauer, G. Antibodies as antigens. The use of mouse monoclonal antibodies to focus human T cells against selected targets. J. Exp. Med., 167:345-352, 1988.

12. Jerne, N. K. Toward a network theory of the immune system. Ann. Immunol. (Paris), 125C:373-389, 1974.

13. Bohn, J. A., BeMiller, J. N. (1-3)-B-D-Glucans as biological response modifiers:a review of structure-functional activity relationships. Carbohydr Polymers, 28:3-14, 1995.

14. Xia, Y, Vetvicka, V., Yan, J., Hanikyrova, M., Mayadas, T., Ross, G. D. The beta-glucan-binding lectin site of mouse CR3 (CD11b/CD18) and its function in generating a primed state of the receptor that mediates cytotoxic activation in response to iC3b-opsonized target cells. J Immunol, 162: 2281-2290, 1999.

15. Di Renzo, L., Yefenof, E., Klein, E. The function of human NK cells is enhanced by beta-glucan, a ligand of CR3 (CD11b/CD18). Eur J Clin Nutr, 21:1755-1758, 1991.

16. Vetvicka, V., Thornton, B. P., Wieman, T. J., Ross, G. D. Targeting of natural killer cells to mammary carcinoma via naturally occurring tumor cell-bound iC3b adn beta-glucan-primed CR3 (CD11b/CD18). J Immunol, 159:599-605, 1997.

17. Vetvicka, V., Thornton, B. P., Ross, G. D. Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells. Journal of Clinical Investigations, 98:50-61, 1996.

18. Czop, J. K., Austen, K. F. Properties of glycans that activate the human alternative complement pathway and interact with the human monocyte beta-glucan receptor. J Immunol, 135:3388-3393, 1985.

19. Thornton, B. P., Vetvicka, V., Pitman, M., Goldman, R. C., Ross, G. D. Analysis of the sugar specificity and molecular location of the B-glucan-binding lectin site of complement receptor type 3 (CD11b/CD18). J Immunol, 156:1235-1246, 1996.

20. Roubroeks, J. P., Skjak-Braek, G., Ryan, L., Christensen, B. E. Molecular weight dependency on the production of the TNF stimulated by fractions of rye (1→3), (1→4)-beta-D-glucan. Scand J Immunol, 52:584-587, 2000.

21. Cheung, N. K., Saarinen, U., Neely, J., Landmeier, B., Donovan, D., Coccia, P. Monoclonal antibodies to a glycolipid antigen on human neuroblastoma cells. Cancer Res, 45:2642-2649, 1985.

22. Modak, S., Kramer, K., Humayun, G., Guo, H. F., Cheung, N. K. V. Monoclonal antibody 8H9 targets a novel cell surface antigen expressed by a wide spectrum of human solid tumors. Cancer Res, 61:4048-4054, 2001.

23. Nethery, A., Raison, R. L., Easterbrook-Smith, S. B. Single-step purification of immunologlobin M on Clq-sepharose. J Immunol Methods, 126:57-60, 1990.

24. Cheung, N. K. V., Walter, E. I., Smith-Mensah, W. H., Ratnoff, W. D., Tykocinski, M. L., Medof, M. E. Decay-accelerating factor protects human tumor cells from complement-mediated cytotoxicity in vitro. J Clin Invest, 81:1122-1128, 1988.

25. Zimmerman, J. W., Lindermuth, J., Fish, P. A., Palace, G. P., Stevenson, T. T., DeMong, D. E. A novel carbohydrate-glycosphingolipid interaction between a beta-(1-3)-glucan immunomodulator, PGG-glucan, and lactosylceramide of human leukocytes. J. Biol. Chem., 273:22014-22020, 1998.

26. Mueller, A., Raptis, J., Rice, P. J., Kalbfleisch, H., Stout, R. D., Ensley, H. E., Browder, W., Williams, D. L. The influence of glucan polymer structure and solution conformation on binding to (1→3)-B-D-glucan receptors in a human monocyte-like cell line. Glycobiology., 10(4):339-346, 2000.

27. Vivanco, F., Munoz, E., Vidarte, L., Pastor, C. The cavalent interaction of C3 with IgG immune complexes. Mol Immunol, 36:843-852, 1999.

28. Yan, J., Vetvicka, V., Xia, Y., Coxon, A., Carroll, M. C., Mayadas, T. N., Ross, G. D. B-glucan a "Specific" biologic response modifier that uses antibodies to target tumors for cytotoxic recognition by leukocyte complement receptor type 3 (CD11b/CD18). J Immunol, 163:3045-3052, 1999.

29. Xia, Y., Vetvicka, V., Yan, J., Hanikyrova, M., Mayadas, T., Ross, G. D. The beta-glucan-binding lectin site of mouse CR3 (CD11b/CD18) and its function in generating a primed state of the receptor that mediates cytotoxic activation in response to iC3b-opsonized target cells. J Immunol, 162:2281-2290, 1999.

30. Thornton, B. P., Vetvicka, V., Ross, G. D. Function of C3 in a humoral response: iC3b/C3dg bound to an immune complex generated with natural antibody and a primary antigen promotes antigen uptake and the expression of co-stimulatory molecules by all B cells, but only stimulates immunoglobulin synthesis by antigen-specific B cells. Clin Exp Immunol, 104:531-537, 1996.

31. Matzinger, P. Tolerance, danger adn the extended family. Annu Rev Immunol, 12:991-1045, 1994.

32. Medzhitov, R., Janeway, C. A. An ancient system of host defense. Curr Opin Immunol, 10:12-15, 1998.

33. Fuchs, E. J., Matzinger, P. Is cancer dangerous to the immune system. Seminars in Immunology, 8:271-280, 1996.

34. Matzinger, P. An innate sense of danger. Seminars in Immunology, 10:399-415, 1998.

35. Liszewski, M. K., Farries, T. C., Lublin, D. M., Rooney, I. A., Atkinson, J. P. Control of the complement System. Adv Immunol, 61:201, 1996.

36. Kim, Y. S., Ryu, J., Han, S., Choi, K., Nam, K., Jang, I., Lemaitre, B., Brey, P. T., Lee, W. Gram-negative bacteria binding protein, a pattern recognition receptor for lipopolysaccharide and beta-1,3-glucan, which mediates the signaling for the induction of innate immune genes in drosophilia melanogaster cells. J Biol Chem, 2000.

37. Jurianz, K., Maslak, S., Garcia-Schuler, H., Fishelson, Z., Kirschfink, M. Neutralization of complement regulatory proteins augments lysis of breast carcinoma cells targeted with rhumAb anti-HER2. Immunopharmacology, 42:209-218, 1999.

38. Livingston, P. O., Wong, G. Y. C., Adluri, S., Tao, Y., Padavan, M., Parente, R., Hanlon, C., Calves, M. J., Helling, F., Ritter, G., Oettgen, H. F., Old, L. J. Improved survival in stage III melanoma patients with GM2 antibodies: a randomized trial of adjuvant vaccination with GM2 ganglioside. J Clin Oncol, 12:1036-1044, 1994.

39. Slovin, S. F., Ragupathi, G., Adluri, S., Ungers, G., Terry, K., Kim, S., Spassova, M., Bornmann, W. G., et al. Carbohydrate vaccines in cancer: Immunogenicity of a fully synthetic globo H hexasaccharide conjugate in man. Proc. Natl. Acad. Sci. USA, 96:5710-5715, 1999.

Third Series of Experiments

Background: β-glucan primes leukocyte CR3 for enhanced cytotoxicity and synergizes with anti-tumor monoclonal antibodies (MoAb). We studied (1→3)-β-D-glucans in xenograft tumor models, and examined the relationship of its anti-tumor effect and physico-chemical properties.

Methods: Established subcutaneous human xenografts were treated with β-glucan daily and MoAb twice weekly by intragastric injection for 29 days. Control mice received either MoAb alone or β-glucan alone. Tumor sizes were monitored over time. β-glucans were studied by carbohydrate linkage analysis, and high performance size-exclusion chromatography with multiple angle laser scattering detection.

Results: Orally administered β-D-glucan greatly enhanced the anti-tumor effects of MoAb against established tumors in mice. This effect correlated with the molecular size of the (1→3), (1→4)-β-D-glucan. (1→3), (1→6)-β-D-glucans also synergized with MoAb, although the effect was generally less. We observed this β-glucan effect irrespective of antigen (GD2, GD3, CD20, epidermal growth factor-receptor, HER-2), human tumor type (neuroblastoma, melanoma, lymphoma, epidermoid carcinoma and breast carcinoma) or tumor sites (subcutaneous versus systemic).

Conclusion: Given the favorable efficacy and toxicity profile of oral β-D-glucan, its role in cancer treatment as an enhancer of the effect of MoAb therapy deserves careful study.

Introduction

Evidence of efficacy of monoclonal antibodies (MoAb) against human cancer in clinical trials is increasingly evident. However, induced or administered antibodies to human tumors have not realized their fullest therapeutic potential, even when they can activate complement-dependent cytotoxicity (CDC) and antibody-dependent cell-mediated cytotoxicity (ADCC). The deposition of C3b and iC3b on tumor cells fails to stimulate phagocytosis or extracellular cytotoxicity by C3-receptor-bearing neutrophils, macrophages, and NK cells, even though these same effector cells can efficiently kill C3b and iC3b opsonized microorganisms. The receptor for iC3b, CR3 (also called CD11b/CD18, Mac-1, or =αMβ2-integrin), is found in monocytes/macrophages, NK cells, and immune cytotoxic T-lymphocytes. CR3 activation requires the engagement of two sites on its a-subunit (CD11b): the iC3b-binding site within the I-domain at the N-terminus and a lectin site at the C-terminus (1,2). β-glucans are specific for the lectin site. When coated with iC3b, yeast cells (with their β-glucan-containing cell wall), engage both iC3b and lectin binding sites on leukocytes, triggering phagocytosis and respiratory burst (2,3). In contrast, tumor cells coated with iC3b cannot activate leukocytes because they lack the CR3-binding β-glucan (4-7). Soluble forms of β-glucans can bind to the lectin site (8,9) and prime both phagocytic and NK cells to kill iC3b coated tumor targets (4,9,10). In murine mammary tumor models in which iC3b was found, intravenous yeast β-glucan reduced tumor size by 70-95% (11). The loss of tumor response in the absence of complement-fixing IgM anti-tumor antibodies (SCID mice), or of C3 (C3 knockout mice), or of leukocyte CR3 (CR3 knockout mice) highlighted the critical components of this iC3b strategy (11).

Although (1→3)-β-D-glucans can be purified from yeast, seaweed and mushrooms, an inexpensive, convenient and safe source of pure (1→3), (1→4)-β-D-glucan is available from barley. Barley β-glucan has been shown to bind to CR3 in vitro (9), to activate ADCC mediated by NK cells (4,10,12), monocyte (8,13), and neutrophils (8,14), as well as to stimulate TNF production by monocytes(15). However, its in vivo immunomodulatory effects, especially when administered by the oral route, have not been tested. In this study we report an unusually strong synergism between anti-tumor antibodies and intragastric injection of β-glucan against a broad spectrum of human tumor xenografts. We also undertake a preliminary investigation of molecular size requirements for this anti-tumor synergy with MoAb.

Methods

Cell lines The cell lines Daudi, RMPI 6666, HS455, SKMel- and A431 were from American Type Culture Collection (ATCC), Rockville, Md. LAN-1 was provided by Dr. R. Seeger, Children's Hospital of Los Angeles, Los Angeles, Calif.; NMB7 by Dr. S.K. Liao (McMaster University, Ontario, Canada); human breast carcinoma cell line BT474 was kindly provided by Dr. David Solit of Memorial Sloan-Kettering Cancer Center (MSKCC), New York, N.Y.; SKNJD and SKNER were established at MSKCC. BT474 was cultured in Dulbecco's modified Eagle with Nutrient Mixture F12 (DMEM/F-12) (Life Technologies Inc. GIBCO-BRL, Rockville, Md.) in a 1:1 mixture fortified with 10% newborn calf serum (Hyclone, Logan, Utah), MEM non-essential amino acids (Gibco-BRL, Grand Island, N.Y.), 100 U/ml of penicillin (Sigma, St. Louis, Mo.), and 100 ug/ml of streptomycin (Sigma). All other cell lines were cultured in RPMI 1640 (Life Technologies Inc.) containing 10% defined calf serum (Hyclone) and 100 U/ml of penicillin, 100 ug/ml of streptomycin and 2 mM L-glutamine (Sigma).

Antibodies MoAb 3F8 (mouse IgG3) and 3G6 (mouse IgM) reactive against GD2 ganglioside expressed on neuroectodermal tumors, and MoAb 8H9 (mouse IgG1) reactive with a glycoprotein expressed on these same tumors have been previously described (16,17). They were purified to >90% purity by affinity chromatography: protein A (Pharmacia, Piscataway, N.J.) for 3F8, and protein G (Pharmacia) for 8H9. Anti-GD3 antibody (R24) (18) was provided by Dr. P. Chapman of MSKCC. Hybridomas producing the anti-epidermal growth factor receptor (EGF-R) antibodies 528 (IgG2a) and 455 (IgG1) were obtained from ATCC (19). Rituximab (anti-CD20) and Herceptin (anti-HER2) were purchased from Genentech, San Francisco, Calif.

β-Glucan Barley, oat and lichenan β-D-glucans were purchased from Sigma and Megazyme International Ireland Ltd., Wicklow, Ireland. Wheat β-glucan was kindly provided by Dr. P. Wood of Agriculture and Agri-Food Canada, West Guelph, Ontario. Betatrim (Quaker Oatrim, 5% β-glucan from oat) was provided by Rhodia Food, Cranbury, N.J. Laminarin was purchased from Sigma and from TCI America, Portland, Oreg. Lentinan (β-glucan extracted from the mushroom *Lentinus edodes*) was provided by the Drug Synthesis and Chemistry Branch, Developmental Therapeutics Program, Division of Cancer Treatment and Diagnosis, National Cancer Institute, Bethesda, Md. β-glucan was dissolved by boiling for 10 minutes in normal saline; Lentinan was dissolved first in DMSO before diluting in water. Digestion with lichenase (endo-1,3:1,4-β-D-glucanase) from *B. subtilis* (Megazyme), was carried out in sodium phosphate buffer (20 mM, pH 6.5) at 40° C. for 10 minutes. Sugar composition and linkage analysis by gas chromatography-mass spectrometry following methylation was performed by the Complex Carbohydrate Research Center, University of Georgia, Athens, Ga., supported in part by the Department of Energy-funded Center for Plant and Microbial Complex Carbohydrates (DF-FG09-93ER-20097) (20). The average ratio of (1→3) to (1→4)-β-linkage in (1→3), (1→4)-β-D-glucans derived from barley, oat and wheat was around 3:7. For molecular size and shape estimations, β-glucan was analyzed by size-exclusion chromatography plus multiple-angle laser light scattering (MALLS) as previously described (21,22). Besides measuring molecular size by MALLS, the slope derived from root mean square radius versus molar-mass plots gave an estimate of the molecular shape: a slope of 0.33 being the shape of a sphere, 0.5 being random coils and 1.0 being rigid rods. High MW β-glucans were found to be random coils in contrast to low MW species which were more sphere-like.

Mice and treatment Athymic nu/nu mice were purchased from the National Cancer Institute-Frederick Cancer Center (Bethesda, Md.) and ICR/SCID from Taconic (White Plains, N.Y.) and maintained in ventilated cages. Experiments were carried out under Institutional Animal Care and Use Committee (IACUC) approved protocols, and institutional guidelines for the proper and humane use of animals in research were followed. Tumor cells were planted ($1-5 \times 10^6$ cells) in 100 µl of Matrigel (Sigma) subcutaneously. Tumor dimensions were measured two to three times a week with vernier calipers, and tumor size was calculated as the product of the two largest perpendicular diameters. For breast carcinoma xenograft studies, 6-8 week old female nude mice (NCI) were initially implanted with 0.72 mg 90-day release 17β-estradiol pellet (Innovative Research of America, Sarasota, Fla.) subcutaneously into the right flank. Twenty-four hours later, $10^7$ BT474 cells were implanted subcutaneously into the left flank. All treatment studies started in groups of 4-5 mice when tumor diameters reached 0.7 to 0.8 cm. Mice received antibody treatment (40-200 ug per day) i.v. (by retroorbital injection) twice weekly and oral β-glucan (400 ug per day) by intragastric injection every day for a total 4 weeks. Mice were weighed once a week and sacrificed according to IACUC guidelines. In the SCID mouse systemic human lymphoma (Daudi) model, 5 million cells were administered i.v., and treatment started 10 days later.

Statistical analysis Because measurement times varied between experiments, and mice in control groups frequently were sacrificed [as required by IACUC for rapidly enlarging tumors] before the end of each experiment, tumor growth was calculated by fitting a regression slope for each individual mouse to log transformed values of tumor size. Slopes were compared between groups using linear regression with monoclonal antibody treatment, β-glucan treatment and combination treatment as covariates. In the study of melanoma tumor growth, β-glucan was given at two different doses. Thus, dose was added as a covariate for analysis. In the study of epidermoid tumor growth, monoclonal antibody was given at three different doses and antibody dose was added as a covariate. Trends for slope by molecular weight were tested by linear regression of slope scores. Survival analysis was conducted by Cox regression using the indicator variables: monoclonal antibody treatment, β-glucan treatment, and combination treatment; in the survival study of lymphoma, Rituximab was given at two different doses and so dose of antibody was added as a covariate for analysis. All analysis were conducted using STATA (Stata Corporation, College Station, Tex.).

Results

Synergy between MoAb and barley β-glucan. We chose the mouse model because of its relative inefficiency in CDC and ADCC (23), and MoAb alone were typically ineffective against established tumors. Oral administration of β-glucan (average MW 210 kD) from barley alone at 400 ug qd×29 days or antibody 3F8 i.v. alone had no appreciable effect on neuroblastoma LAN-1 tumor growth. The tumor growth rates for the β-glucan alone, 3F8 alone, and saline controls were virtually identical. In contrast, when we combined oral β-glucan with i.v. 3F8, significantly less tumor growth was observed in the 3F8 antibody alone group, 0.7% vs 5.4% increase in tumor size per day, respectively. In the regression model, only combination treatment significantly reduced tumor growth (4.9% per day, 95% CI 2.4%, 7.4%, p=0.001). Nude mice (n=22) with established NMB7 xenografts were treated with 3F8 (200 ug twice a week iv) and 400 ug of β-glucan po daily for a total of 4 weeks. Control mice received either saline alone, 3F8 alone, or β-glucan alone. Median survival was 30 days in control groups and 166 days in the treatment (3F8 plus β-glucan, n=22, FIG. 27). In the Cox model, combination β-glucan/antibody treatment was the only variable significantly associated with improved survival (hazard ratio treatment: 0.07, 95% CI 0.02, 0.27; p<0.0001). Ten (45%) mice in the combination group survived long term with a median follow-up of 248 days. Only one mouse in any of the control groups (<5%) remained alive during the experiment. This anti-tumor effect was evident against a panel of GD2-positive neuroblastoma lines: NMB7, SK-N-JD, and SK-N-ER. Barley β-glucan was effective when the route of administration was either intragastric or intraperitoneal. In contrast, if the tumor was antigen-negative (e.g. GD2-negative rhabdomyosarcoma HTB82), 3F8 plus β-glucan treatment was ineffective. When the dose of oral β-glucan was decreased by 10-folds from 4000 ug to 400 ug, 40 ug and 4 ug, the tumor growth rate were 4.3±2.2%, 3.8±0.9%, 8.1±0.8%, and 9.5±0.9%, respectively. These data suggest an optimal dose somewhere between 400 ug and 4000 ug. The animals did not suffer weight loss, or histopathologic changes in the major organs at necropsy in the treatment groups, irrespective of β-glucan dose. When the glucan was heated at 95° C. up to 3 hours, its in vivo effects remained intact. However, following digestion with endo-(1→3), (1→4)-β-D-glucanase, all its in vivo effect was destroyed. In addition, the anti-tumor effect of the antibodies was lost when the Fc of the antibody was removed by pepsin, or when an IgG1 isotype (Moab 8H9) was used.

Molecular size of (1→3), (1→4)-β-D-glucan and anti-tumor synergy with MoAb. Barley β-glucans of increasing molecular sizes were tested at an oral dose of 40 ug or 400 ug. Anti-tumor effect improved with increasing molecular size, with a 2.2% decrease in tumor growth rate per day for each increase of 100 kD in molecular weight; 95% confidence interval 3.0%, 1.4%; p<0.00001 (Table 1). However, since the shape of the β-glucan in aqueous solution correlated with average MW by MALLS analysis, potency could be a function of molecular shape rather than molecular size.

Source of β-D-glucan and anti-tumor synergy with MoAb. A (1→3), (1→4)-β-D-glucan of average MW of 210 kD derived from barley was chosen as our standard. Using the neuroblastoma xenograft model, equivalent ug doses of β-glucans derived from various plant sources were compared in their anti-tumor activity when administered by intragastric injection plus intravenous MoAb 3F8 (Table 1). As expected, since the chemical composition (1→3), (1→4)-β-D-glucan derived from barely, oat and wheat were similar, comparable levels of synergy with MoAb was found, and high MW also appeared to be more effective. When glucans with (1→6)-β-linkages were tested, high MW species (e.g. Lentinan 1,500 kD) was not as effective compared to the standard. On the other hand, low MW (1→3), (1→6) preparations (e.g. Laminarin 5 kD), though not as effective as standard, was more potent than low MW (1→3), (1→4)-β-D-glucan.

β-glucan effect in a wide spectrum of MoAbs and human tumor models. Using the standard β-glucan from barley (210 kD), a series of MoAb were screened against a panel of human tumor xenografts in various mouse strains. The combination of oral β-glucan with complement activating MoAb suppressed tumor growth significantly in contrast to MoAb or β-glucan alone. This was shown for anti-GD3 MoAb (R24) against melanoma (FIG. 28A), anti-EGF-R (528) MoAb against epidermoid carcinoma A431 (FIG. 28B), and anti-HER2 (Herceptin) against human breast carcinoma BT474 xenografts in nude mice (FIG. 28C). Again, MoAb 455, an IgG1 anti-EGF-R was ineffective against epidermoid carcinoma in contrast to the IgG2a 528 (FIG. 28B). In metastatic lymphoma model, Daudi cells injected i.v.established widespread tumors in brain, spinal cord, kidneys and ovaries of SCID mice (data not shown). In the Cox model, only combination treatment and dose of Rituximab were associated with survival. Median survival was 59 days in animals receiving either Rituximab alone, β-glucan alone or no treatment. Median survival in the group treated with Rituximab plus β-glucan was 97 days (hazard ratio 0.09; 95% CI 0.03, 0.27; p<0.001).

Discussion

We have shown that β-glucans greatly enhanced the anti-tumor effects of MoAb against established tumors in mice. We observed this effect irrespective of route of β-glucan administration (intragastric or intraperitoneal), antigen (GD2, GD3, CD20, EGFR, HER2), human tumor type (NB, melanoma, epidermoid carcinoma, lymphoma, breast cancer), mouse strain (athymic nu/nu, severe combined immune deficiency mice), or tumor site (subcutaneous versus systemic). β-glucan was heat-stable, its anti-tumor effect was dose- and schedule-dependent, requiring antibody-Fc, but not cytophilicity of the antibody. Neither antibody nor β-glucan alone was effective. We detected no toxicities even at β-glucan doses of 4000 ug/day for 4 weeks. This synergy of (1→3), (1→4)-β-D-glucan with MoAb increased with β-glucan MW.

β-glucans have been tested for tumor therapy in mice for nearly 40 years (24,25). Several forms of mushroom-derived β-glucans are used clinically in Japan to treat cancer, including polysaccharide Kureha (PSK, from *Coriolus versicolor*), Lentinan and Schizophyllan. In randomized trials in Japan, PSK and Schizophyllan have moderately improved survival rates in some cancer trials (26-30), and less encouraging in others(31,32). While β-glucans are not used by western oncologists, β-glucan containing botanical medicines such as Ling-Zhi, maitake and green barley are widely used by cancer patients in the US as alternative/complementary cancer therapies, often with poor clinical validation or quality control.

Given the biology of iC3b targeted cytotoxicity, β-glucan should have clinical potential. However, limitations with existing β-glucan strategies are several fold. They are generally expensive and inconvenient to administer: e.g. Lentinan and Schizophyllan are given i.v. daily over long periods of time. Besides being insoluble, they contain proteins and non-β-glucan carbohydrates, which confound mechanistic studies and complicate the manufacturing and control process. Because of protein contaminants they are potentially allergenic. The spontaneous cross-linking of CR3 by β-glucan of high MW can cause neutrophil degranulation and cytokine release from macrophages, resulting in undesirable clinical toxicities. For low MW β-glucan, besides their low affinity for CR3, they have rapid renal clearance. Without anti-tumor antibodies to activate human complement, β-glucan is largely ineffective. Here we addressed these limitations by (1) using pure (1→3), (1→4)-β-D-glucan from barley, (2) administering β-glucan orally instead of intravenously, and (3) coadministration of tumor-specific antibodies to ensure complement activation.

Previous studies have demonstrated that oral β-glucans activate splenic and peritoneal macrophages for tumor-cytotoxicity. In a study of $^{14}$C-labeled oral β-glucan, sequestration in the liver was observed (33), suggesting that oral β-glucan entered the blood and behaved pharmacokinetically similar to intravenously administered low MW β-glucan (34-36). These studies also suggested that processing by the gastrointestinal tract produced β-glucan with high activity for CR3. Besides this model of intravasation of processed barley β-glucan, leukocytes could also be activated directly in the gut before homing to the tumor. It is of interest that unpurified β-glucan (Betratrim) has low biologic activity in our model. Despite the abundance of β-glucan (3% of the dry weight) in grains, its bioavailability from cereals is limited since high MW β-glucans requires high temperature (>60° C.) extraction and final gelling. It is therefore not surprising that high-fiber (13.5 g/day) wheat-bran supplement did not have anti-tumor effects in recent human trials (37).

Our findings using (1→3), (1→4)-β-D-glucans from barley were unexpected. In previous studies, the comb-like branch structure of (1→3), (1→6)-β-linkage (e.g. lentinan, schizophyllan, laminarin, and β-glucan from Baker's yeast) was deemed requisite for its anti-tumor effect (38). In those models, however, I-cells were essential. In our studies, (1→3), (1→4)-β-glucan could reproducibly enhance the anti-tumor effect of MoAb in immunodeficient mice, clearly demonstrating that neither T nor B cells were needed. Although the absolute proof of complement and CR3 requirement would have to await experiments with knock-out mice, preliminary evidence from studying MoAb isotypes and subclasses did suggest that complement activation was required. Since most cancers express mCRP (CD46, CD55, CD59) on their cell surface (39-46), complement mediated tumor lysis is typically inefficient. Nevertheless, despite these inhibitory proteins, iC3b has been detected on tumor cells isolated from fresh human breast tumors, and enough levels could be deposited by MoAb (e.g. Herceptin) in vitro to opsonize tumor cells for phagocytes and NK cells in vitro (47). It is possible that sublethal levels of complement activation deposited enough iC3b to optimize tumor killing, a strategy that deserves clinical investigation.

REFERENCES FOR THE THIRD SERIES OF EXPERIMENTS

1. Ross G D, Cain J A, Lachmann P J. Membrane complement receptor type three (CR3) has lectin-like properties analogous to bovine conglutinin and functions as a receptor for zymosan and rabbit erythrocytes as well as a receptor for iC3b. J Immunol 1985; 134:3307-15.
2. Ross G D, Cain J A, Myones B L, Newman S L, Lachmann P J. Specificity of membrane complement receptor type three (CR3) for beta-glucans. Complement Inflamm 1987; 4:61-74.
3. Cain J A, Newman S L, Ross G D. Role of complement receptor type three and serum opsonins in the neutrophil response to yeast. Complement Inflamm 1987; 4:75-86.
4. Vetvicka V, Thornton B P, Wieman T J, Ross G D. Targeting of natural killer cells to mammary carcinoma via naturally occurring tumor cell-bound iC3b adn beta-glucan-primed CR3 (CD11b/CD18). J Immunol 1997; 159:599-605.
5. Irie K, Irie R F, Morton D L. Evidence for in vivo reaction of antibody and complement to surface antigens of human cancer cells. Science 1974; 186:454-6.
6. Seegal B C, Hsu K C, Lattimer J K, Habif D V, Tannenbaum M. Immunoglobulins, complement and foreign antigens in human tumor cells. Int Arch Allergy Immunol 1976; 52:205-11.
7. McCoy J P, Hofheinz D E, Ng A B, Nordqvist S, Haines H G. Tumor-bound immunoglobulin in human gynecologic cancers. J. Natl. Cancer Inst. 1979; 63:279-83.
8. Thornton B P, Vetvicka V, Pitman M, Goldman R C, Ross G D. Analysis of the sugar specificity and molecular location of the B-glucan-binding lectin site of complement receptor type 3 (CD11b/CD18). J Immunol 1996; 156:1235-46.
9. Xia Y, Vetvicka V, Yan J, al. e. The beta-glucan-binding lectin site of mouse CR3 (CD11b/CD18) and its function in generating a primed state of the receptor that mediates cytotoxic activation in response in iC3b-opsonized target cells. J Immunol 1999; 162:2281-90.
10. Vetvicka V, Thornton B P, Ross G D. Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells. Journal of Clinical Investigations 1996; 98:50-61.
11. Yan J, Vetvicka V, Xia Y, Coxon A, Carroll M C, Mayadas T N, et al. B-glucan a "Specific" biologic response modifier that uses antibodies to target tumors for cytotoxic recognition by leukocyte complement receptor type 3 (CD11b/CD18). J Immunol 1999; 163:3045-52.
12. Di Renzo L, Yefenof E, Klein E. The function of human NK cells is enhanced by beta-glucan, a ligand of CR3 (CD11b/CD18). Eur J Clin Nutr 1991; 21:1755-8.
13. Czop J K, Austen K F. Properties of glycans that activate the human alternative complement pathway and interact with the human monocyte beta-glucan receptor. J Immunol 1985; 135:3388-93.
14. Thornton B P, Vetvicka V, Ross G D. Function of C3 in a humoral response: iC3b/C3dg bound to an immune complex generated with natural antibody and a primary antigen promotes antigen uptake and the expression of co-stimulatory molecules by all B cells, but only stimulates immunoglobulin synthesis by antigen-specific B cells. Clinical Experimental Immunology 1996; 104:531-7.
15. Roubroeks J P, Skjak-Braek G, Ryan L, Christensen B E. Molecular weight dependency on the production of the TNF stimulated by fractions of rye (1→3), (1→4)-beta-D-glucan. Scand J Immunol 2000; 52:584-7.
16. Cheung N K, Saarinen U, Neely J, Landmeier B, Donovan D, Coccia P. Monoclonal antibodies to a glycolipid antigen on human neuroblastoma cells. Cancer Research 1985; 45:2642-9.
17. Modak S, Kramer K, Humayun G, Guo H F, Cheung N K V. Monoclonal antibody 8H9 targets a novel cell surface antigen expressed by a wide spectrum of human solid tumors. Cancer Research 2001; 61:4048-54.
18. Houghton A N, Mintzer D, Cordon-Cardo C, Welt S, Fliegel B, Vadhans S, et al. Mouse monoclonal antibody detecting GD3 ganglioside: a phase I trial in patients with malignant melanoma. Proc. Natl Acad Sci, USA 1985; 82:1242-6.

19. Masui H, Moroyama T, Mendelsohn J. Mechanism of antitumor activity in mice for anti-epidermal growth factor receptor monoclonal antibodies with different isotypes. Cancer Res 1986; 46:5592-8.

20. Ciucanu I, Kerek F. A simple and rapid method for the permethylation of carbohydrates. Carbohydrate Res 1984; 131:209-17.

21. Wyatt P. Light scattering and the absolute characterization of macromolecules. Analytical Chimica Acta 1993; 272: 1-40.

22. Knuckles B E, Yokohama W H, Chiu M M. Molecular characterization of barley b-glucans by size-exclusion chromatography with multiple-angle laser-light scattering and other detectors. Cereal Chemistry 1997; 74:599-604.

23. Bergman I, Basse P H, Barmada M A, Griffin J A, Cheung N K V. Comparison of in vitro antibody-targeted cytoxicity using mouse, rat and human effectors. Cancer Immunol. Immunother. 2000; 49:259-66.

24. Diller I C, Mankowski Z T, Fisher M E. The effect of yeast polysaccharides on mouse tumors. Cancer Res 1963; 23:201-8.

25. Sveinbjornsson B, Rushfeldt C, Seljelid R, Smedsrod B. Inhibition of establishment and growth of mouse liver metastases after treatment with interferon gamma and beta-1,3-D-Glucan. Hepatology 1998; 27(5):1241-8.

26. Niimoto M, Hattori T, Tamada R, Sugimachi K, Inokuchi K, Ogawa N. Postoperative adjuvant immunochemotherapy with mitomycin C, futraful, and PSK for gastric cancer. An analysis of data on 579 patients followed for five years. Japanese Journal of Surgery 1988; 18:681-6.

27. Mitomi T, Tsuchiya S, Iijima N, Aso K, Suzuki K, Nishiyama K, et al. Randomized, controlled study on adjuvant immunochemotherapy with PSK in curatively resected colorectal cancer. The cooperative study group of surgical adjuvant immunochemotherapy for cancer of colon and rectum (Kanagawa). Dis Colon Rectum 1992; 35:123-30.

28. Ogoshi K, Satou H, Isono K, Mitomi T, Endoh M, Sugita M. Immunotherapy for esophageal cancer. A randomized trial in combination with radiotherapy and radiochemotherapy. Cooperative study group for esophageal cancer in Japan. American Journal of Clinical Oncology 1995; 18:216-22.

29. Fujimoto S, Furue H, Kimura T, Kondo T, Orita K, Taguchi T, et al. Clinical outcome of postoperative adjuvant immunochemotherapy with sizofiran for patients with resectable gastric cancer: a randomised controlled study. Eur J Cancer 1991; 27:1114-8.

30. Okamura K, Suzuki M, Chihara T, Fujiwara A, Fukada T, Goto S, et al. Clinical evaluation of sizofiran conbined with irradiation in patients with cervical cancer. A randomized controlled study; a five-year survival rate. Biotherapy 1989; 1:103-7.

31. Toi M, Hattori T, Akagi M, Inokuchi K, Orita K, Sugimachi K, et al. Randomized adjuvant trial to evaluate the addition of tamoxifen and PSK to chemotherapy in patients with primary breast cancer. 5-year results from the Nishi-Nippon group of the adjuvant chemoendocrine therapy for breast cancer organization. Cancer 1992; 70:2475-83.

32. Ohno R, Yamada K, Masaoka T, al. e. A randomized trial of chemoimmunotherapy of acute nonlymphocytic leukemia in adults using a protein-bound polysaccharide preparation. Cancer Immunol. Immunother. 1984; 18:149-54.

33. Ikuzawa M, Matsunaga K, Nishiyama S, Nakajima S, Kobayashi Y, Andoh T, et al. Fate and distributionof an antitumor protein-bound polysaccharide PSK (Krestin). Int. J. Immunopharmacol. 1988; 10:415-23.

34. Yan J, Vetvicka V, Xia Y, Hanikyrova M, Mayadas T N, Ross G D. Critical role of kupffer cell CR3 (CD11b/CD18) in the clearance of IgM-opsonized erythrocytes or soluble beta-glucan. Immunopharmacology 2000; 46:39-54.

35. Smedsrod B, Seljelid R. Fate of intravenously injected aminated beta(1→3) polyglucose derivatized with 125I-tyraminyl cellobiose. Immunopharmacology 1991; 21:149-58.

36. Suda M, Ohno N, Adachi Y, Yadomae T. Relationship between the tissue distribution and antitumor activity of highly branched (1→3)-beta-D-glucan, SSG. Biol. Pharm. Bull. 1994; 17:131-5.

37. Alberts DSea. Lack of effects of a high-fiber cereal supplement on the recurrence of colorectal adenomas. N Engl J Med 2000; 342:1156-62.

38. Bohn J A, BeMiller J N. (1-3)-B-D-Glucans as biological response modifiers:a review of structure-functional activity relationships. Carbohydr Polymers 1995; 28:3-14.

39. Koretz K, Bruderlein S, Henne C, Moller P. Expression of CD59, a complement regulator protein and a second ligand of the CD2 molecule,and CD46 in normal and neoplastic colorectal epithelium. Br J Cancer 1993; 68:926-31.

40. Juhl H, Helmig F, Baltzer K, Kalthoff H, Henne-Bruns D, Kremer B. Frequent Expression of Complement Resistance Factors CD46,CD55,and CD55 on Gastrointestinal Cancer Cells Limits the Therapeutic Potential of Monoclonal Antibody 17-1A. Journals of Surgical Oncology 1997; 64:222-30.

41. Brasoveanu L I, Altomonte M, Gloghini A, Fonsatti E, Coral S, Gasparollo A, et al. Expression of protectib (CD59) in human melanoma and its functional role in cell- and complement-cytotoxicity. Int J Cancer 1995; 61:548-56.

42. Hara T, Kojiama A, Fukuda H, Masaoka T, Fukumori Y, Matsumoto M, et al. Levels of complement regulator protein, CD35(CR1),CD46(MCP) and CD55(DAF) in human haematological malignancies. British Journal of Haemotolgy 1992; 82:368-73.

43. Marquart H V, Gronbaek K, Christensen B E, Svehag S-E, Lesli RGQ. Complement activation by malignant B-cells from patients with chronic lymphcytic leukemia. Clinical Experimental Immunology 1995; 102:575-81.

44. Bjorge L, Hakulinen J, Wahlstrom T, Matre R, Meri S. Complement-regulatory proteins on ovarian malignancies. Int J Cancer 1997; 70:14-25.

45. Jurianz K, Maslak S, Garcia-Schuler H, Fishelson Z, Kirschfink M. Neutralization of complement regulatory proteins augments lysis of breast carcinoma cells targeted with rhumAb anti-HER2. Immunopharmacology 1999; 42:209-18.

46. Jurianz K, Ziegler S, Garcia-Schuler H, Kraus S, Bohana-Kashtan O, Fishelson Z, et al. Complement resistance of tumor cells: basal and induced mechanisms. Mol Immunol 1999; 36:929-39.

47. Klein E, DiRenzo L, Yefenof E. Contribution of C3,CD11b/CD18 to cytolysis by human NK cells. Mol Immunol 1990; 27:1343-7.

TABLE 1

Neuroblastoma growth rate (%/day) when treated with i.v. 3F8 and oral β-glucan derived from various plant sources.

| Glucans | Description | MW (kD) | 400 ug**** % tumor growth relative to standard | 40 ug**** |
|---|---|---|---|---|
| (1→3),(1→4)-β-D-glucan* | | | | |
| Standard barley glucan | | 210 | 100 | 100 |
| Antibody alone Control | | — | 287 | — |
| Saline control | | — | 307 | — |
| Barley | MW standard | 337 | 79 | 59 |
|  | MW standard | 237 | 100 | 100 |
|  | MW standard | 178 | 117 | 520 |
|  | MW standard | 131 | 163 | 481 |
|  | MW standard | 48 | 180 | 516 |
|  | BBG111 | 266 | 60 | 242 |
|  | BBG126 | 90 | 146 | — |
| Oat | BBG128 | 262 | 88 | — |
|  | BBG127 | 201 | 104 | — |
| Wheat | BBG117 | 138 | — | 190 |
| Betatrim | Unpurified | — | 325 | — |
| Lichenan | BBG113 | 132 | 189 | — |
| (163),(166)-β-D-glucan | | | | |
| Laminarin** | BBG108 | 5 | 177 | |
| Laminarin*** | BBG109 | 32 | 326 | |
| Lentinan | BBG114 | 1491 | 123 | |

*(163)β-linkage was ~30% for all the (163),(164)-β-D-glucans
**(163)β-linkage was 92%
***(163)β-linkage was 53%
****Either 400 or 40 ug of (163)-β-D-glucans was administered orally qd x 29 days plus intravenous MoAb 3F8 twice a week (M,Th) x 8 doses in groups of 4-5 mice each. Tumor size was measured periodically over the entire treatment period. Tumor growth curve and potency were calculated as detailed in Materials and Methods.

Fourth Series of Experiments

Phase I study of oral β-glucan and intravenous anti-GD2 monoclonal antibody 3F8 among patients with metastatic neuroblastoma The main findings are as follows:

The clinical response data for the first eight patient shows that β-glucan has been extremely well-tolerated. There have been no dose-limiting toxicities. There is a somewhat bitter flavor, but this can be easily masked by chewing gum.

The in vitro correlates suggests that biologic activity of β-glucan with antibody-dependent cell cytotoxicity has been enhanced by treatment.

The patients are all children or adolescents with relapsed or refractory stage 4 neuroblastoma metastatic to bone, marrow or distant lymph nodes, some with large soft tissue masses. Even though these patients have been treated with only 1-2 cycles of antibody+glucan at the lowest dose, we have seen 6/8 patients demonstrating radiographic or histologic response.

Results and Discussion
Toxicities:

| Glucan | Dose level: | #patients DLT |
|---|---|---|
| I | 6 | 0 |
| II | 2 | 0 |

In vitro biologic correlates:

Some initial data are available from the in vitro cytotoxicity studies. Though the number of patients is very small, some interesting trends are apparent. In particular, granulocyte mediated antibody-dependent cellular cytotoxicity (ADCC) directed at complement sensitized tumor targets approximately doubled from baseline values after just 3 days of β-glucan therapy (p=0.01 by Wilcoxon signed-rank test). Although there are insufficient data for inferential comparisons, we can compare these results with those from a previous trial at MSKCC in which GM-CSF was used concurrently with 3F8. Increases in ADCC averaged ~40% in these patients, suggesting that β-glucan enhanced ADCC more consistently.

Clinical tumor response after cycle #1

| Dose level | Patient | Bone marrow | MIBG | CT | Tumor markers |
|---|---|---|---|---|---|
| I | 1 | NE | Improved | Improved | NE |
|  | 2 | SD | SD | PD | PD |
|  | 3 | CR | Improved | PD | CR |
|  | 4 | SD | Improved | SD | Improved |
|  | 5 | PR | Improved | NE | CR |
|  | 6 | SD | Improved | Improved | SD |
| II | 1 | SD | SD | SD | SD |
|  | 2 | — | — | PD | — |

CR = complete remission,
NE = not evaluable (no evaluable disease),
PD = progressive disease,
PR = partial remission, from diffuse involvement to a single focus of tumor on biopsy,
SD = stable disease These clinical responses are highly promising given that they are demonstrated after 1-2 cycles of antibody+glucan in a Phase I trial. (FIG. 29A) shows extensive osseous metastasis in the femora, fibulae, pelvis, rib, left scapula, right clavicle, humeri, skull and spine. Heart, liver, stomach and colon uptakes are physiologic. (FIG. 29B) shows a significant improvement of the patient 5 two months after a single cycle of therapy. This is uncommon in our 13 years of experience using 3F8 in patients with refractory or relapsed metastatic stage 4 neuroblastoma.

Fifth Series of Experiments

Rituximab activates complement-mediated and antibody-dependent cell-mediated cytotoxicities, and is effective against B-cell lymphomas. β-glucans are naturally occurring glucose polymers that bind to the lectin domain of CR3, a receptor widely expressed among leukocytes, priming it for binding to iC3b activated by antibodies. Barley-derived (1→3), (1→4)-β-D-glucan (BG), when administered orally (400 μg per day×29 days), strongly synergized with subtherapeutic doses of intravenous rituximab (200 μg twice/week×8 doses) in the therapy of CD20-positive human lymphomas. Growth of established subcutaneous non-Hodgkin's lymphoma (NHL) (Daudi and EBV-derived B-NHL) or Hodgkin's disease (Hs445 or RPMI6666) xenografted in SCID mice was significantly suppressed, when compared to mice treated with rituximab or BG alone. Survival of mice with disseminated lymphoma (Daudi and Hs445) was significantly increased. There was no weight loss or clinical toxicity in treated animals. This therapeutic efficacy and lack of toxicity of BG plus rituximab supports further investigation into its clinical utility.

Introduction

The chimeric anti-CD20 antibody rituximab is being evaluated in an increasing number of disorders. After clinical efficacy was initially demonstrated against relapsed and refractory follicular/low grade non-Hodgkin's lymphoma[1], responses to rituximab have been reported in other malignant and non-malignant B-cell disorders[2]. Several mechanisms of action have been proposed including activation of apoptotic pathways[3], elaboration of cytokines[4], and elicitation of host complement-dependent cytotoxicity (CDC) and antibody-dependent cell-mediated cytotoxicity (ADCC)[5]. Although many patients with B-cell disorders respond to rituximab, remissions are often transient[6]. More than 50% of lymphomas recurrent after rituximab treatment failed to respond the second time[7]. Mechanisms of resistance to rituximab are as yet unclear, and may include paucity or loss of target antigen[8], pharmacokinetic variations among individual patients, FcR polymorphism[9], resistance to complement activity[10], or inherent gene expression of the lymphoma[11].

β-glucans are complex polymers of glucose with affinity for the lectin site of the CR3 receptor on leucocytes[12]. With bound β-glucan, CR3 (CD11b) is primed to engage iC3b fragments deposited on cells by complement-activating antibodies. This receptor mediates the diapedesis of leukocytes through the endothelium and stimulates phagocytosis, degranulation and tumor cytotoxicity. Many fungi present β-glucan or β-glucan-like CR3 binding ligands on their cell surface. Hence, when iC3b deposition occurs, both CD11b and lectin sites become engaged, and phagocytosis and respiratory burst is triggered[13]. In contrast, tumor cells lack such molecules, and even when coated with iC3b do not generally activate CR3 and cannot activate leucocytes. Soluble forms of β-glucan bind to lectin sites and prime both phagocytic and NK cells to kill iC3b-coated tumor targets[14].

(1→3), (1→4)-D-β-glucan (BG), a soluble, barley-derived β-glucan has advantages over previously studied (1→3), (1→6)-β-glucans, particularly efficacy when administered orally and a good safety profile[15]. In vivo synergism between BG and the complement-fixing antibody 3F8 against human neuroblastoma xenografts[15,16] was recently demonstrated. The synergism between BG and rituximab against lymphoma is now reported.

Study Design
Cell Lines:
Human Burkitt's lymphoma cell line, Daudi, and Hodgkin's disease (HD) cell lines Hs445 and RPMI 6666 were purchased from American Type Culture Collection (Rockville, Md.). Human EBV-BLCL were established using previously described methods[17].

Mice:
Fox Chase ICR SCID mice (Taconic, White Plains, N.Y.) were maintained under institutionally approved guidelines and protocols.

Tumor Models:
Subcutaneous tumors were established by injecting 5×10[6] cells suspended in 0.1 ml of Matrigel (Becton-Dickinson, Franklin Lakes, N.J.) into mice flanks. Tumor dimensions were measured two to three times a week and tumor size was calculated as the product of the two largest diameters. Mice were sacrificed when maximum tumor dimension exceeded 20 mm. A disseminated tumor model was established in SCID mice as previously described[18]. Briefly, 5×10[6] Daudi or Hs445 cells in 100 µl normal saline were injected intravenously into SCID mice. Tumors grew systemically and mice became paralyzed when tumor cells infiltrated the spinal cord, resulting in hind-leg paralysis. Mice were sacrificed at onset of paralysis or when animals lost 10% of their body weight.

Treatment Regimens:
For mice with subcutaneous tumors, therapy was initiated after tumors were established (7-8 mm diameter). For the disseminated tumor model, therapy was initiated ten days after injection of tumor cells. Groups of at least five mice per treatment regimen received either rituximab, BG, neither or both. 200 µg rituximab (Genentech, San Francisco, Calif.) was injected intravenously twice weekly for a total of eight injections and 400 µg BG (Sigma, St. Louis, Mo.) administered orally via intragastric gavage daily for 29 days. Animals were weighed weekly and observed clinically at least once daily.

Statistical Analysis:
Tumor growth was calculated by fitting a regression slope for each individual mouse to log transformed values of tumor size. Slopes were compared between groups using t-tests using a previously described method for censored observations[19]. Survival in mice with disseminated disease was compared using Kaplan-Meier analysis and proportion of deaths was compared by Fisher's exact $\chi 2$ test. Analyses were conducted using STATA 7 (Stata Corporation, College Station, Tex.).

Results and Discussion
In all subcutaneous xenograft models, significant reduction in tumor growth was noted in mice treated with a combination of rituximab and BG. Mice treated with rituximab alone showed a modest reduction in tumor growth, while those treated with BG alone or left untreated had unabated tumor growth (FIG. 30A, 30B, 30C). All tumors except for those treated with combination therapy grew beyond 20 mm size and mice had to be sacrificed. Mice on combination treatment had persistent tumor suppression even after treatment was stopped. In a multivariable linear model of tumor growth rate, using dummy variables for treatment, the interaction between BG and rituximab was positive and significant, demonstrating synergism.

For disseminated xenografts, there was a significant difference in survival between the combination and control groups for both NHL and HD models (p<0.005, by log-rank) (FIGS. 31A and 31B). 5/38 mice and 2/8 mice with disseminated Daudi and Hs445 tumors respectively treated with combination BG and rituximab were surviving>12 months after therapy was discontinued suggesting complete eradication of disease. In contrast, 0/29 and 0/8 mice receiving rituximab alone in respective groups survived (15% vs 0% survival; $\chi 2=0.01$). There was no significant weight loss or other clinically apparent adverse effects. That BG is absorbed can be inferred from the fact that it could be detected intracellularly within fixed and permeabilized peripheral blood leucocytes by immunofluorescence (data not shown).

In these studies, synergism between BG and rituximab was highly significant irrespective of the type of CD20-positive lymphoma. Improved responses in Daudi xenografts as compared to Hs445 may be attributable to higher CD20 expression in the former (Mean geometric fluorescence channel for Daudi 241 compared to 184 for Hs445). When tumors that progressed were examined for CD20 expression by immunofluorescence studies of single cell suspensions or indirect immunohistochemistry of frozen sections, no significant difference was noted between groups treated with rituximab, BG alone or rituximab+BG (data not shown), indicating that treatment with rituximab+BG was not associated with loss of CD20.

Synergism between other complement-activating monoclonal antibodies and BG[15,16] were previously demonstrated. The current data extend this observation to rituximab. CDC is considered an important mechanism for rituximab cytotoxicity. Rodent complement is not inhibited efficiently by human complement regulatory proteins (mCRP). Therefore CDC can be an effective anti-tumor mechanism in xenograft models. However in our study, at sub-therapeutic doses of antibody, rituximab-mediated ADCC and CDC were not sufficient to effect tumor cell killing. Since BG has no direct effect on ADCC[20], this synergy is most likely a result of iC3b-mediated tumor cytotoxicity. Lymphoma cells express mCRP including CD46, CD55, and CD59[19,21]. However, iC3b-mediated cytotoxicity is unaffected by the presence of CD59 which affects only MAC-mediated complement cytotoxicity[22]. Furthermore, in human breast carcinoma tumors, deposition of iC3b has been demonstrated despite the presence of mCRP[23] indicating that unlike their inhibitory effect on MAC, effect on iC3b-mediated tumor cytotoxicity is not absolute.

If this synergistic effect can be safely reproduced in humans, iC3b-mediated cytotoxicity may be a potential strategy to overcome rituximab resistance in patients with B-cell malignancies. Since neither T nor B cells are required for this synergistic effect, BG may have a potential role even in immunocompromised lymphoma patients. Furthermore, in patients with autoimmune disorders, B-cell depletion may be enhanced with this non-toxic oral therapy. Conversely, β-glucans can enhance release of cytokines such as TNF-α and IL-6[24], and because the acute toxicities of rituximab are also related to cytokine release secondary to complement activation[25], there is a potential of increased toxicity when BG and rituximab are used in combination. Carefully designed phase I studies are necessary in order to define the safety and efficacy in developing BG as an adjunct to rituximab therapy in the treatment of B-cell disorders and in antibody-based therapies of other cancers.

REFERENCES FOR THE FIFTH SERIES OF EXPERIMENTS

1. Maloney D G, Liles T M, Czerwinski D K, Waldichuk C, Rosenberg J, Grillo-Lopez A, Levy R. Phase I clinical trial using escalating single-dose infusion of chimeric anti-CD20 monoclonal antibody (IDEC-C2B8) in patients with recurrent B-cell lymphoma. Blood. 1994; 84:2457-2466

2. Cheson B D. Rituximab: clinical development and future directions. Expert Opin Biol Ther. 2002; 2:97-110

3. Alas S, Emmanouilides C, Bonavida B. Inhibition of interleukin 10 by Rituximab results in Down-regulation of Bcl-2 and sensitization of B-cell Non-Hodgkin's lymphoma to apoptosis. Clin Cancer Res. 2001; 7:709-723

4. Chow K U, Sommerlad W D, Boehrer S, Schneider B, Seipelt G, Rummel M J, Hoelzer D, Mitrou P S, Weidmann E. Anti-CD20 antibody (IDEC-C2B8, rituximab) enhances efficacy of cytotoxic drugs on neoplastic lymphocytes in vitro: role of cytokines, complement, and caspases. Haematologica. 2002; 87:33-43

5. Reff M E, Carner K, Chambers K S, Chinn P C, Leonard J E, Raab R, Newman R A, Hanna N, Anderson D R. Depletion of B cells in vivo by a chimeric mouse human monoclonal antibody to CD20. Blood. 1994; 83:435-445

6. McLaughlin P, Grillo-Lopez A J, Kink B K, Levy R, Czuczman M S, Williams M E, Heyman M R, Bence-Bruckler I, White C A, Cabanillas F, Jain V, Ho A D, Lister J, Wey K, Shen D, Dallaire B K. Rituximab chimeric anti-CD20 monoclonal antibody therapy for relapsed indolent lymphoma: half of patients respond to four-dose treatment program. J Clin Oncol. 1998; 16:2825-2833

7. Davis T A, Grillo-Lopez A J, White C A, McLaughlin P, Czuczman M S, Link B K, Maloney D G, Weaver R L, Rosenberg J, Levy R. Rituximab anti-CD20 monoclonal antibody therapy in non-Hodgkin's lymphoma: safety and efficacy of re-treatment. J Clin Oncol. 2000; 18:3135-3143

8. Davis T A, Czerwinski D K, Levy R. Therapy of B-cell lymphoma with anti-CD20 antibodies can result in the loss of CD20 antigen expression. Clin Cancer Res. 1999; 5:611-615

9. Cartron G, Dacheux L, Salles G, Solal-Celigny P, Bardos P, Colombat P, Watier H. Therapeutic activity of humanized anti-CD20 monoclonal antibody and polymorphism in IgG Fc receptor FcgammaRllla gene. Blood. 2002; 99:754-758

10. Golay J, Zaffaroni L, Vaccari T, Lazzari M, Borleri G M, Bernasconi S, Tedesco F, Rambaldi A, Introna M. Biologic response of B lymphoma cells to anti-CD20 monoclonal antibody rituximab in vitro: CD55 and CD59 regulate complement-mediated cell lysis. Blood. 2000; 95:3900-3908

11. Bohen S P, Troyanskaya O G, Alter O, Warnke R, Botstein D, Brown P O, Levy R. Variation in gene expression patterns in follicular lymphoma and the response to rituximab. Proc Natl Acad Sci U S A. 2003; 100:1926-1930

12. Bohn J A, BeMiller J N. (1-3)-B-D-Glucans as biological response modifiers:a review of structure-functional activity relationships. Carbohydr Polymers. 1995; 28:3-14

13. Ross G D, Cain J A, Myones B L, Newman S L, Lachmann P J. Specificity of membrane complement receptor type three (CR3) for beta-glucans. Complement Inflamm. 1987; 4:61-74

14. Xia Y, Vetvicka V, Yan J, Hanikyrova M, Mayadas T, Ross GD. The beta-glucan-binding lectin site of mouse CR3 (CD11b/CD18) and its function in generating a primed state of the receptor that mediates cytotoxic activation in response to iC3b-opsonized target cells. J Immunol. 1999; 162:2281-2290

15. Cheung N, Modak S. Oral (1-3, (1-4)-beta-glucan synergizes with anti-ganglioside GD2 monoclonal antibody 3F8 in the therapy of neuroblastoma. Clin Cancer Res. 2002; 8:1217-1223

16. Cheung N K, Modak S, Vickers A, Knuckles B. Orally administered beta-glucans enhance anti-tumor effects of monoclonal antibodies. Cancer Immunol Immunother. 2002; 51:557-564

17. Koehne G, Gallardo H F, Sadelain M, O'Reilly R J. Rapid selection of antigen-specific T lymphocytes by retroviral transduction. Blood. 2000; 96:109-117

18. Wei B R, Ghetie M A, Vitetta E S. The combined use of an immunotoxin and a radioimmunoconjugate to treat disseminated human B-cell lymphoma in immunodeficient mice. Clin Cancer Res. 2000; 6:631-642

19. Vardi Y, Ying Z, Zhang C-H. Two-sample tests for growth curves under dependent right censoring. Biometrika. 2001; 88:949-960

20. Yan J, Vetvicka V, Xia Y, Coxon A, Carroll M C, Mayadas T N, Ross GD. B-glucan a "Specific" biologic response modifier that uses antibodies to target tumors for cytotoxic recognition by leukocyte complement receptor type 3 (CD11b/CD18). J Immunol. 1999; 163:3045-3052

21. Treon S P, Mitsiades C, Mitsiades N, Young G, Doss D, Schlossman R, Anderson K C. Tumor cell expression of CD59 is associated with resistance to CD20 serotherapy in patients with B-cell malignancies. J Immunother. 2001; 24:263-271

22. Jurianz K, Ziegler S, Garcia-Schuler H, Kraus S, Bohana-Kashtan O, Fishelson Z, Kirschfink M. Complement resistance of tumor cells: basal and induced mechanisms. Mol Immunol. 1999; 36:929-939

23. Vetvicka V, Thornton B P, Wieman T J, Ross G D. Targeting of natural killer cells to mammary carcinoma via naturally occurring tumor cell-bound iC3b and beta-glucan-primed CR3 (CD11b/CD18). J Immunol. 1997; 159:599-605

24. Adachi Y, Okazaki M, Ohno N, Yadomae T. Enhancement of cytokine production by macrophages stimulated with (1→3)-beta-D-glucan, grifolan (GRN), isolated from Grifola frondosa. Biol Pharm Bull. 1994; 17:1554-1560

25. van der Kolk L E, Grillo-Lopez A J, Baars J W, Hack C E, van Oers MH. Complement activation plays a key role in the side-effects of rituximab treatment. Br J Haematol. 2001; 115:807-811

What is claimed is:

1. A method of enhancing the anti-tumor effect of a complement-activating antibody administered to a subject, comprising orally administering a β-(1,3)-(1,4)-glucan, sequentially or concurrently with said antibody, in an amount effective to enhance the anti-tumor effect of the antibody,
wherein the complement-activating antibody binds to cancer cells expressing an antigen selected from a group consisting of CD20, GD2, GD3, EGFR and HER2, and wherein said antibody is administered intravenously, intramuscularly, intraperitoneally, orally or intradermally.

2. The method of claim 1, wherein said complement-activating antibody is a monoclonal antibody.

3. The method of claim 1, wherein said complement-activating antibody is capable of activating antibody-dependent cell-mediated cytotoxicity.

4. The method of claim 1, wherein the cancer cells expressing CD20 are those of non-Hodgkins's lymphoma, Hodgkins's lymphoma or Epstein-Barr related lymphoma.

5. The method of claim 1, wherein the cancer cells expressing GD2 are those of neuroblastoma.

6. The method of claim 1, wherein the cancer cells expressing GD3 are those of melanoma.

7. The method of claim 1, wherein the cancer cells expressing EGFR are those of epidermoid carcinoma.

8. The method of claim 1, wherein the cancer cells expressing HER2 are those of breast cancer.

9. The method of claim 1, wherein the β-glucan is derived from moss, wheat or oat.

10. The method of claim 1, wherein the subject is a mammal or human.

11. The method of claim 1, wherein the β-glucan is administered at a dose of about 25 mg/kg/day to about 140 mg/kg/day, five days a week for 2-4 weeks.

12. A method of enhancing the anti-tumor effect of a complement-activating antibody administered to a subject, comprising orally administering a β-(1,3)-(1,4)-glucan, sequentially or concurrently with said antibody, in an amount effective to enhance the anti-tumor effect of the antibody,
wherein said complement-activating antibody binds to cancer cells of neuroblastoma, melanoma, lymphoma, epidermoid carcinoma or breast cancer, and wherein said antibody is administered intravenously, intramuscularly, intraperitoneally, orally or intradermally.

13. The method of claim 12, wherein said complement-activating antibody is a monoclonal antibody.

14. The method of claim 12, wherein said complement-activating antibody is capable of activating antibody-dependent cell-mediated cytotoxicity.

15. The method of claim 12, wherein the lymphoma cells express the antigen CD20.

16. The method of claim 12, wherein the neuroblastoma cells express the antigen GD2.

17. The method of claim 12, wherein the melanoma cells express the antigen GD3.

18. The method of claim 12, wherein the epidermoid carcinoma cells express EGFR.

19. The method of claim 12, wherein the breast cancer cells express HER2.

20. The method of claim 12, wherein the subject is a mammal or human.

21. The method of claim 12, wherein the lymphoma is selected from a group consisting of non-Hodgkin's lymphoma, Hodgkin's lymphoma and Epstein-Barr related lymphoma.

22. The method of claim 12, wherein the β-glucan is administered at a dose of about 25 mg/kg/day to about 140 mg/kg/day, five days a week for 2-4 weeks.

23. The method of claim 12, wherein the β-glucan is derived from moss, wheat or oat.

* * * * *